(12) United States Patent
Izutsu et al.

(10) Patent No.: US 6,489,122 B1
(45) Date of Patent: Dec. 3, 2002

(54) **METHOD OF DETECTING ANTI-*CHLAMYDIA PNEUMONIAE* ANTIBODY USING *CHLAMYDIA PNEUMONIAE*-SPECIFIC ANTIGENS**

(75) Inventors: Hiroshi Izutsu, Ibaraki (JP); Kazuhiko Obara, Ibaraki (JP); Akira Matsumoto, Okayama (JP)

(73) Assignee: Hitachi Chemical Company, Ltd., Tokyo (JP)

( * ) Notice: Subject to any disclaimer, the term of this patent is extended or adjusted under 35 U.S.C. 154(b) by 0 days.

(21) Appl. No.: 09/689,913

(22) Filed: Oct. 12, 2000

Related U.S. Application Data

(62) Division of application No. 08/809,326, filed as application No. PCT/JP99/01896 on Sep. 20, 1995, now Pat. No. 6,165,478.

(30) Foreign Application Priority Data

| Sep. 20, 1994 | (JP) | 6-224711 |
| Apr. 28, 1995 | (JP) | 7-106006 |
| Apr. 28, 1995 | (JP) | 7-106008 |
| Apr. 28, 1995 | (JP) | 7-106009 |
| Apr. 28, 1995 | (JP) | 7-106010 |
| Apr. 28, 1995 | (JP) | 7-106011 |

(51) Int. Cl.[7] .............................................. G01N 33/53
(52) U.S. Cl. .................. 435/7.1; 424/263.1; 435/4; 435/7.2; 435/7.32; 435/252.3; 435/320.1
(58) Field of Search .................. 424/263.1, 234.1; 435/6, 7.36, 69.1, 69.5, 252.3, 320.1, 7.1, 7.2, 7.32, 4; 530/350; 536/23.1, 23.4

(56) References Cited

PUBLICATIONS

Horlow et al. Antibodies: A laboratory manual. Cold Spring Harbor Laboratories Publications, Cold Spring Harbor, NY ed. Harlow et al., p. 76.*

Paul Fundamental Immunology, Raven Press, New York, NY; 1993, 3rd Edition, p.249–251.*

Iwakura et al. Dihydrofolate reductase as a new "affinity handle". Journal of Biochemistry (1992) Val. 111, No. 1, pp. 37–45.*

Roberts et al., ASM 101st General Meeting, Session No. 242/C, Session No. 242/C, Abstract C–356, (2001).

* cited by examiner

*Primary Examiner*—Jeffrey Stucker
*Assistant Examiner*—Ulrike Winkler
(74) *Attorney, Agent, or Firm*—Birch, Stewart, Kolasch & Birch, LLP

(57) ABSTRACT

*Chlamydia pneumoniae* antigenic polypeptides, which comprise polypeptide A containing a sequence of at least 5 consecutive amino acids in the polypeptide of SEQ ID NO: 1, DNAs encoding the antigenic polypeptides, or DNAs complementary thereto; a method for detection and/or measurement of an anti-*Chlamydia pneumoniae* antibody, wherein the antigenic polypeptide is used as an antigen; reagents for detection and/or measurement of an anti-*Chlamydia pneumoniae* antibody, which comprise the antigenic polypeptide as an antigen; agents for diagnosis of *Chlamydia pneumoniae* infections, which comprise the antigenic polypeptide as an active ingredient; fused proteins of an antigenic polypeptide of *Chlamydia pneumoniae* with dihydrotolate reductase, in which polypeptide A containing a sequence of at least 5 consecutive amino acids in the polypeptide of SEQ ID NO: 1 is bound to the polypeptide of SEQ ID NO: 14 either directly or via an intervening amino acid or amino acid sequence; DNAs encoding the fused proteins, or DNAs complementary thereto.

24 Claims, No Drawings

METHOD OF DETECTING ANTI-*CHLAMYDIA PNEUMONIAE* ANTIBODY USING *CHLAMYDIA PNEUMONIAE*-SPECIFIC ANTIGENS

This application is a division of application Ser. No. 08/809,326, filed Mar. 19, 1997, now U.S. Pat. No. 6,165,478, which is a U.S. national phase application under U.S.C. 0371 of the international application PCT/JP95/01896 filed Sep. 20, 1995 which is incorporated by reference herein in its entirety.

FIELD OF THE INVENTION

The invention relates to *Chlamydia pneumoniae* antigenic polypeptides, fused proteins containing the polypeptides, DNAs coding therefor, recombinant vectors carrying the DNAs, transformants containing the recombinant vectors, a method for production of antibody, a method and reagents for detection and/or measurement of antibody, a method and agents for diagnosis of *Chlamydia pneumoniae* infections, probes and primers for detection and/or measurement of *Chlamydia pneumoniae* gene, and a method and reagents for detection and/or measurement of *Chlamydia pneumoniae* gene. The invention can be effectively used in the pharmaceutical industry, particularly in the preparation of agents for diagnosis of *Chlamydia pneumoniae* infections.

BACKGROUND ART

Several kinds of species are known in Chlamydia, that is, *Chlamydia trachomatis, Chlamydia psittaci, Chlamydia pecorum, Chlamydia pneumoniae* and the like. *Chlamydia trachomatis* causes trachoma, venereal lymphogranuloma, urogenital infections, inclusion conjunctivitis, neonatal pneumonia and the like. *Chlamydia psittaci* causes psittocosis and the like. *Chlamydia pneumoniae* causes respiratory infections, atypical pneumonia and the like.

Since the symptoms of infections in the respiratory apparatus which are caused by *Chlamydia pneumoniae* are similar to those of infections caused by *Mycoplasma pneumoniae* or Influenza virus, physicians often make a wrong diagnosis. Hence, there is a need for the development of a simple method for diagnosing the infections caused by *Chlamydia pneumoniae*.

In general, an infection can reliably be diagnosed by detecting the causative bacterium in the infected site or by detecting an antibody against the causative bacterium in body fluids such as a sera and the like. The former method is called an antigen test and the latter is called an antibody test. Both of them are clinically important. As for *Chlamydia pneumoniae*, there is known an antibody test which is carried out by a method in which an antibody is detected by using an elementary body of *Chlamydia pneumoniae*.

However, this method has the disadvantage that the elementary body of *Chlamydia pneumoniae* reacts not only with an antibody against *Chlamydia pneumoniae* but also with antibodies against other species of Chlamydia, thus being fairly unspecific. This is because the elementary body of *Chlamydia pneumoniae* contains an antigen which is also present in other species of geneus Chlamydia than *Chlamydia pneumoniae*, that is, *Chlamydia trachomatis* and *Chlamydia psittaci*.

As a plasmid which can be used for the expression of a large amount of a protein in *E. coli*, pBBK10MM is known (Japanese Unexamined Patent Publication No. Hei 4-117284). This plasmid can be used for the expression of a fused protein of an anti-allergic peptide with DHFR. The expressed fused protein also maintains the enzymatic activity of DHFR and can therefore be purified easily by utilizing the characteristic properties and activities of DHFR.

Genetic screening has been carried out to diagnose infections. In this screening, the presence of the gene of a microorganism to be detected in a sample is examined using nucleic acid probes and the like.

As for *Chlamydia pneumoniae*, there is known a genetic screening method which is carried out as disclosed in Japanese Unexamined Patent Publication No. Sho 64-500083, U.S. Pat. No. 5,281,518 and WO94/04549.

However, Japanese Unexamined Patent Publication No. Sho 64-500083 and U.S. Pat. No. 5,281,518 only disclose that a chromosomal DNA of *Chlamydia pneumoniae* or a DNA fragment which is obtained by cleaving the chromosomal DNA with a restriction enzyme or the like is used as a probe. The base sequences of these DNA molecules are not determined and the specificity of these probes are therefore unclear. In addition, it is difficult to determine the reaction conditions.

Although WO94/04549 discloses a method using a probe which is hybridized to ribosome RNA or DNA corresponding thereto, the specificity of these probes is not reliable because the homology of ribosomal RNA is relatively high in all organisms.

DISCLOSURE OF THE INVENTION

It is an object of the invention to provide antigenic polypeptides that do not react with antibodies against species of geneus Chlamydia other than *Chlamydia pneumoniae*, such as *Chlamydia trachomatis*, *Chlamydia psittaci* and the like and which react only with a *Chlamydia pneumoniae*-specific antibody and can thereby detect the *Chlamydia pneumoniae*-specific antibody.

Another object of the invention is to provide a method for synthesizing large amounts of the antigenic polypeptides by using gene recombination techniques.

A further object of the invention is to provide a method for production of an anti-*Chlamydia pneumoniae*-specific antibody, a method and reagents for detection and/or measurement of the anti-*Chlamydia pneumoniae*-specific antibody, and agents for diagnosis of *Chlamydia pneumoniae* infections, all by using said antigenic polypeptides.

A still further object of the invention is to provide probes and primers for detecting and/or measuring specifically *Chlamydia pneumoniae* gene, a method and reagents for detection and/or measurement of *Chlamydia pneumoniae* gene and agents for diagnosis of *Chlamydia pneumoniae* infections, all by using the probes or primers.

An even further object of the invention is to provide antigenic polypeptides for detection of an antibody which reacts with geneus Chlamydia including *Chlamydia pneumoniae, Chlamydia trachomatis, Chlamydia psittaci* and the like.

SUMMARY OF THE INVENTION

The subject matters of the invention are as follows:

(1) A *Chlamydia pneumoniae* antigenic polypeptide, which comprises polypeptide containing a sequence of at least 5 consecutive amino acids in the polypeptide of SEQ ID NO: 1 (hereinafter referred to as "polypeptide A").

(2) The antigenic polypeptide of (1), wherein said polypeptide A is a polypeptide in which at least one amino acid is deleted from the polypeptide of SEQ ID NO: 1.

(3) The antigenic polypeptide of (1), wherein said polypeptide A is a polypeptide in which at least one amino acid in the polypeptide of SEQ ID NO: 1 is replaced with other amino acid or a polypeptide in which at least one amino acid is added in the polypeptide of SEQ ID NO: 1.
(4) The antigenic polypeptide of (1), wherein said polypeptide A is a polypeptide in which an amino acid or a peptide sequence is bound to a sequence of at least 5 consecutive amino acids in the polypeptide of SEQ ID NO: 1.
(5) The antigenic polypeptide of (1), wherein said polypeptide A is a polypeptide containing the amino acid sequence of SEQ ID NO: 1.
(6) The antigenic polypeptide of (1), wherein said polypeptide A is a polypeptide containing the amino acid sequence of SEQ ID NO: 2.
(7) The antigenic polypeptide of (1), wherein said polypeptide A is a polypeptide containing the amino acid sequence of SEQ ID NO: 5.
(8) A DNA encoding the antigenic polypeptide of any one of (1)–(7), or a DNA complementary thereto.
(9) The DNA of (8), which contains the base sequence of SEQ ID NO: 3.
(10) The DNA of (8), which contains the base sequence of SEQ ID NO: 4.
(11) The DNA of (8), which contains the base sequence of SEQ ID NO: 7.
(12) A recombinant vector carrying the DNA of any one of (8)–(11).
(13) The recombinant vector of (12), which is plasmid pCPN533 α containing the base sequence of SEQ ID NO: 10.
(14) A transformant containing the recombinant vector of (12) or (13).
(15) A method for production of an anti-*Chlamydia pneumoniae* antibody,
wherein the antigenic polypeptide of any one of (1)–(7) is used as an antigen.
(16) A method for detection and/or measurement of an anti-*Chlamydia pneumoniae* antibody, wherein the antigenic polypeptide of any one of (1)–(7) is used as an antigen.
(17) A reagent for detection and/or measurement of an anti-*Chlamydia pneumoniae* antibody, which comprises the antigenic polypeptide of any one of (1)–(7) as an antigen.
(18) A reagent for diagnosis of a *Chlamydia pneumoniae* infection, which comprises the antigenic-polypeptide of any one of (1)–(7) as an active ingredient.
(19) A fused protein of a *Chlamydia pneumoniae* antigenic polypeptide with dihydrofolate reductase, in which polypeptide containing a sequence of at least 5 consecutive amino acids in the polypeptide of SEQ ID NO: 1 is bound to the polypeptide of SEQ ID NO: 14 (hereinafter referred to as "polypeptide B") either directly or via an intervening amino acid or amino acid sequence.
(20) The fused protein of (19), wherein said polypeptide B is a polypeptide in which at least one amino acid is deleted from the polypeptide of SEQ ID NO: 1.
(21) The fused protein of (19), wherein said polypeptide B is a polypeptide in which at least one amino acid in the polypeptide of SEQ ID NO: 1 is replaced with other amino acids or a polypeptide in which at least one amino acid is added in the polypeptide of SEQ ID NO: 1.
(22) The fused protein of (19), which is a polypeptide containing the amino acid sequence of SEQ ID NO: 15.
(23) The fused protein of (19), which is a polypeptide containing the amino acid sequence of SEQ ID NO: 16.
(24) A DNA encoding the fused protein of any one of (19)–(23), or a DNA complementary thereto.
(25) The DNA of (24), which contains the base sequence of SEQ ID NO: 17.
(26) The DNA of (24), which contains the base sequence of SEQ ID NO: 18.
(27) A recombinant vector carrying the DNA of any one of (24)–(26).
(28) The recombinant vector of (27), which is plasmid pCPN533T.
(29) A transformant containing the recombinant vector of (27) or (28).
(30) A method for production of an anti-*Chlamydia pneumoniae* antibody, wherein the fused protein of any one of (19)–(23) is used as an antigen.
(31) A method for detection and/or measurement of an anti-*Chlamydia pneumoniae* antibody, wherein the fused protein of any one of (19)–(23) is used as an antigen.
(32) A reagent for detection and/or measurement of an anti-*Chlamydia pneumoniae* antibody, which comprises the fused protein of any one of (19)–(23), as an antigen.
(33) A reagent for diagnosis of a *Chlamydia pneumoniae* infection, which comprises the fused protein of any one of (19)–(23) as an active ingredient.
(34) A probe for detection and/or measurement of *Chlamydia pneumoniae* gene, which comprises any one of
  (a) a DNA containing a sequence of at least 10 consecutive bases in the DNA of SEQ ID NO: 3,
  (b) a DNA complementary to DNA (a), or
  (c) a DNA having at least 90% homology to DNA (a) or (b).
(35) The probe of (34), which contains the base sequence of SEQ ID NO: 19.
(36) The probe of (34), which contains the base sequence of SEQ ID NO: 20.
(37) A method for detection and/or measurement of *Chlamydia pneumoniae* gene, characterized in that the probe of any one of (34)–(36) is used.
(38) A reagent for detection and/or measurement of *Chlamydia pneumoniae* gene, which comprises the probe of any one of (34)–(36).
(39) An agent for diagnosis of a *Chlamydia pneumoniae* infection, which comprises the probe of any one of (34)–(36) as an active ingredient.
(40) A primer for detection and/or measurement of *Chlamydia pneumoniae* gene, which comprises any one of
  (a) a DNA containing a sequence of at least 10 consecutive bases in the DNA of SEQ ID NO: 3,
  (b) a DNA complementary to DNA (a), or
  (c) a DNA having at least 90% homology to DNA (a) or (b).
(41) The primer of (40), which contains the base sequence of SEQ ID NO: 19.
(42) The primer of (40), which contains the base sequence of SEQ ID NO: 20.
(43) A method for detection and/or measurement of *Chlamydia pneumoniae* gene, wherein the primer of any one of (40)–(42) is used.
(44) A reagent for detection and/or measurement of *Chlamydia pneumoniae* gene, which comprises the primer of any one of (40)–(42).
(45) A reagent for diagnosis of a *Chlamydia pneumoniae* infection, which comprises the primer of any one of (40)–(42) as an active ingredient.
(46) A *Chlamydia pneumoniae* antigenic polypeptide, which is selected from the group consisting of (a) the polypeptide of SEQ ID NO: 5, (b) a polypeptide in which at least one amino acid is deleted from the polypeptide of SEQ ID NO: 5, (c) a polypeptide in which at least one amino acid in the polypeptide of SEQ ID NO: 5 is replaced with another amino acid, and (d) a fused polypeptide of any one of (a)–(c) with another amino acid or peptide.

(47) A *Chlamydia pneumoniae* antigenic polypeptide, which is selected from the group consisting of (a) the polypeptide of SEQ ID NO: 6, (b) a polypeptide in which at least one amino acid is deleted from the polypeptide of SEQ ID NO: 6, (c) a polypeptide in which at least one amino acid in the polypeptide of SEQ ID NO: 6 is replaced with another amino acid, and (d) a fused polypeptide of any one of (a)–(c) with another amino acid or peptide.

(48) A DNA encoding the polypeptide of (46), or a DNA complementary thereto.

(49) A DNA encoding the polypeptide of (47), or a DNA complementary thereto.

(50) The DNA of (48), wherein said DNA encoding the polypeptide of (46) is the DNA of SEQ ID NO: 7.

(51) The DNA of (49), wherein said DNA encoding the polypeptide of (47) is the DNA of SEQ ID NO: 8.

(52) A recombinant vector carrying the DNA of any one of (48)–(51).

DETAILED DESCRIPTION OF THE INVENTION

In the specification, deoxynucleotides having only one base are referred to as "monodeoxynucleotides" and deoxynucleotides having at least two bases are referred to as "DNAS", unless otherwise indicated.

The invention will now be explained in detail.

Antigen Polypeptide

The antigen polypeptide of the present invention is formed of polypeptides containing at least five continued amino acid sequences in a polypeptide of SEQ ID No. 1 (hereinafter referred to as "Polypeptide A") from the viewpoint of the minimum size in which a peptide is allowed to possess antigenicity.

Since the antigen-antibody reaction can be expected to gain in sensitivity in proportion as the length of amino acid sequence increases, the polypeptide A is appropriately formed of not less than 20, preferably not less than 100, and more preferably not less than 250 amino acids.

So long as the polypeptide A possesses the antigenicity inherent in *Chlamydia pneumoniae*, it tolerates the loss of amino acids (1–250 amino acids, for example) from the polypeptide of SEQ ID No. 1. If the number of missing amino acids is unduly large, the polypeptide A will tend to suffer the antigenicity inherent in *Chlamydia pnuemoniae* to be impaired.

When the number of missing amino acids is large (five or more, for example), the polypeptide A prefers such missing amino acids (five or more, for example) to occur in a continued series for the sake of retaining the antigenicity of *Chlamydia pneumoniae*.

So long as the polypeptide A possesses the antigenicity inherent in *Chlamydia pneumoniae*, it tolerates the substitution of part of the amino acids (1–100 amino acids, for example) by other amino acids or the insertion of amino acids (1–100 amino acids, for example) in the polypeptide of SEQ ID No. 1. If the number of amino acids involved in the substitution or insertion is unduly large, the polypeptide A will tend to suffer the antigenicity inherent in *Chlamydia pnuemoniae* to be impaired. When the number of amino acids involved in the substitution or insertion is large (five or more, for example), the polypeptide A prefers the amino acids (five or more, for example) to occur in a continued series for the sake of retaining the antigenicity of *Chlamydia pneumoniae*. The amino acids to be involved in the substitution are preferred to possess such similar qualities as are observed in the substitution between glycine and alanine, for example.

So long as the polypeptide A possesses the antigenicity inherent in *Chlamydia pneumoniae*, it may be a polypeptide having amino acids or peptides ligated directly or through the medium of an intervening amino acid sequence to at least five continued amino acid sequences in the polypeptide of SEQ ID No. 1.

The peptides for the ligation are appropriately formed of not more than 1000 amino acid sequences, preferably not more than 500 amino acid sequences, and more preferably not more than 200 amino acid sequences for the sake of retaining the antigenicity inherent in *Chlamydia pneumoniae*.

As concrete examples of such amino acids or peptides, leucine, leucine-methionine, dihydrofolic acid reductase (DHFR), and β-galactosidase may be cited.

As concrete examples of the polypeptide A using DHFR or β-galactosidase as a peptide, DHFR-*Chlamydia pneumoniae* antigen polypeptide-fused protein and β-galactosidase-*Chlamydia pneumoniae* antigen polypeptide-fused protein may be cited. DHFR or β-galactosidase may be ligated either directly or through the medium of an intervening amino acid sequence with *Chlamydia pneumoniae* antigen polypeptide.

As concrete examples of the polypeptide A, the polypeptides of SEQ ID No. 1, SEQ ID No. 2, and Sequence No. 5 may be cited.

Though the intervening amino acid sequence is not defined particularly, the amino acid sequences of leucine and leucine-methionine are examples.

As concrete examples of the fused protein of the present invention, the polypeptide formed of amino acid sequences of SEQ ID No. 15 and the polypeptide formed of amino acid sequences of SEQ ID No. 16 may be cited.

Among the fused proteins cited above, the polypeptide formed of the amino acid sequences of SEQ ID No. 15 including the whole antigen polypeptide of 53 kDa of *Chlamydia pneumoniae* proves particularly advantageous.

The method of chemical synthesis and the method of gene recombination are available for the production of the antigen polypeptide of this invention.

The polypeptide of SEQ ID No. 1 of this invention is an antigen polypeptide formed of 488 amino acid residues as shown in the table of sequences.

The polypeptide of SEQ ID No. 2 of this invention is an antigen polypeptide formed of 271 amino acid residues as shown in the table of sequences. * The polypeptide of SEQ ID No. 5 of this invention is an antigen polypeptide formed of 259 amino acid residues as shown in the table of sequences.

Among other antigen polypeptides mentioned above, the polypeptide of SEQ ID No. 1 containing the whole antigen polypeptide of 53 kDa of *Chlamydia pnuemoniae* proves particularly advantageous.

Method for Production of Antigen Polypeptide

The method of chemical synthesis and the method of gene recombination are available for the production of the antigen polypeptide of this invention.

Among the methods of chemical synthesis is counted the MAP (multiple antigen peptide) method, for example. The MAP method befits the synthesis of a peptide formed of not more than 30 amino acid sequences. This synthesis can be implemented by the use of a commercially available peptide synthesizing device.

Among the methods of gene recombination is counted a method which comprises inserting a DNA coding for the antigen polypeptide of this invention in a vector thereby constructing a recombinant vector, inserting the recombinant vector in a host thereby producing a transformant, and isolating the peptide aimed at from the transformant.

The DNA coding for the antigen polypeptide of this invention will be described afterward.

The vector may be plasmid, phage, etc.

As concrete examples of the host, Escherichia coli, Bacillus subtilis, yeast, etc. may be cited.

Now, the method for forming the transformant and the method for refining the peptide aimed at by the use of the transformant will be described in detail below.

Preparation of Recombinant Vector Carrying the DNA Encoding the Antigenic Polypeptide and Transformants Containing the Same The $\lambda$ phage obtained by screening (see infra) is already a kind of recombinant vector carrying the DNA of the invention. Additional recombinant vectors can be prepared by inserting in a known plasmid vector or phage vector the DNA encoding the *Chlamydia pneumoniae* antigenic polypeptide (see infra) in a conventional procedure. In this case, a linker may be used if necessary. As the known plasmid vector, pBR322, pUC18, pUC19, pBBK10MM or the like can be used. Plasmids pBR322, pUC18 and pUC19 are commercially available and pBBK10MM is described in detail in Japanse Unexamined Patent Publication No. Hei 4-117284. As the phage vector, $\lambda$gt11 phage, $\lambda$gt10 phage or the like can be used. In any case, recombinant vectors corresponding to the parent vectors used can be obtained.

The recombinant vectors carrying the DNA of the invention include plasmid pCPN533 $\alpha$, 53-3S $\lambda$ phage and the like (see infra).

The obtained recombinant vector is introduced into a host to prepare a transformant. If an *E. coli*-derived plasmid or $\lambda$ phage is used, an *E. coli* strain such as HB 101 can be used as a host. The host is treated to become a competent cell. A competent cell obtained by treating *E. coli* strain HB101 is commercially available from Takara Shuzo Co., Ltd. A method of introducing the recombinant vector into a host to prepare a transformant is described in "Molecular Cloning".

The obtained transformant is cultured to form colonies. Plasmid DNAs are obtained from each of the colonies and cleaved with an appropriate restriction enzyme. A transformant having a desired recombinant plasmid is selected according to the results of agarose gel electrophoretic analysis of the cleaved plasmid DNA. The plasmid vectors thus prepared include plasmid pCPN533 $\alpha$.

Examples of the transformant thus prepared include *E. coli* strain HB101 containing the recombinant vector pCPN533 $\alpha$.

Preparation of Recombinant Vectors Carrying the DNA Encoding Fused Protein of the *Chlamydia pneumoniae* Antigenic Polypeptide with DHFR and Transformants Containing the Same The DNA molecule encoding the *Chlamydia pneumoniae* antigenic polypeptide (see infra) is ligated to the DNA molecule encoding DHFR (see infra) by means of a commercially available kit. In the ligation, a linker may be used if necessary. A DNA ligation kit (Takara Shuzo Co., Ltd) can be used as a commercially available kit. If the DNA obtained by the ligation does not have a replication origin and does not therefore function as a plasmid, the DNA is inserted in a separate plasmid vector, which may be pBR322, pUC18 or the like.

The ligated DNA is introduced into a host to prepare a transformant. If an *E. coli*-derived plasmid is used, an *E. coli* strain such as HB 101 can be used as a host. The host is treated to become a competent cell. A competent cell obtained by treating *E. coli* strain HB101 is commercially available from Takara Shuzo Co., Ltd. The method of introducing the ligated DNA into a host to prepare a transformant is described in "Molecular Cloning".

The obtained transformant is cultured to form colonies. Plasmid DNAs are obtained from each of the colonies and cleaved with an appropriate restriction enzyme. A transformant having a desired recombinant plasmid is selected according to the results of agarose gel electrophoretic analysis. An example of the plasmid vector thus prepared is plasmid pCPN533T.

An example of the transformant thus prepared is *E. coli* strain h HB101 containing the recombinant vector pCPN533T.

The transformant is cultured by shaking an incubator containing the transformant at an appropriate temperature in a medium that allows the transformant to grow until a sufficient amount of the desired antigenic polypeptide is accumulated in the transformant. If *E. coli* strain HB101 containing the recombinant vectors pCPN533 $\alpha$ or PCPN533T are used as a transformant, the cell is cultured while shaking in ampicillin-containing LB medium at 37° C. overnight. Subsequently, the culture is inoculated in ampicillin-containing TB medium and further cultured while shaking at 37° C. an overnight. A method for preparing the TB medium is described in "Molecular Cloning".

The cultured transformant is harvested by centrifugation and suspended in a buffer. The transformant is disrupted by sonication of the suspension. If the transformant is *E. coli*, the cell may be lysed by successively adding lysozyme and an SDS-containing buffer to the suspension.

When the polypeptide aimed at is secretory in quality, the culture broth is centrifuged to obtain the supernatant.

After the disruption of the transformant, the cell residue is removed by centrifugation, thereby obtaining the supernatant. Streptomycin sulfate is added to the supernatant. The mixture is stirred for a certain period of time and centrifuged to precipitate nucleic acids, thereby obtaining the supernatant.

This supernatant is precipitated with ammonium sulfate and centrifuged. Generally, the precipitate is recovered as the product. Since the supernatant possibly contains the peptide aimed at, the practice of sampling and analyzing the supernatant thereby confirming the presence or absence of the peptide proves advantageous.

Either the solution of the precipitate in a small amount of buffer solution or the supernatant is fractionated by liquid chromatography. The proteins contained in the fractions are blotted by the Western blotting method using a *Chlamydia pneumoniae*-specific monoclonal antibody to obtain the fractions containing antigen polypeptide. When the polypeptide A is a protein fused with DHFR, a Methotrexate column can be used as the column for the liquid chromatography. Specific procedures of the removal of residues such as a cell membrane and the like, the removal of DNA by addition of streptomycin sulfate, the recovery of proteins by addition of ammonium sulfate and a Western blotting method are described in "Molecular Cloning".

DNAs Encoding the Antigenic Polypeptides

In the invention, the DNA encoding the polypeptide of SEQ ID NO: 1 means DNAs selected from the group of DNAs which are obtained by translating the amino acids of the polypeptide of SEQ ID NO: 1 to triplets in accordance with the genetic code (each amino acid is assigned 1–6 sets of nucleotide sequences). This group of DNAs includes the DNA of SEQ ID NO: 3.

The DNA encoding the antigenic polypeptide A means DNAs encoding the polypeptide A. These DNAs are selected from the group of DNAs which are obtained by translating the amino acid sequence for the polypeptide A to triplets in accordance with the genetic code.

As the polypeptide A, those polypeptides which have been described under the item "Antigenic Polypeptides" above may be given. As the DNA encoding the polypeptide A, nucleotides sequences which correspond to the amino acid sequences for those polypeptides may be given.

Similarly, the DNA encoding the polypeptide of SEQ ID NO: 2 means DNAs selected from the group of DNAs which are obtained by translating the amino acids of the polypeptide of SEQ ID NO: 2 to triplets in accordance with the genetic code. This group of DNAs includes the DNA of SEQ ID NO: 4.

Additionally, the DNA encoding the polypeptide of SEQ ID NO: 5 means DNAs selected from the group of DNAs which are obtained by translating the amino acids of the polypeptide of SEQ ID NO: 5 to triplets in accordance with the genetic code. This group of DNAs includes the DNA of SEQ ID NO: 7.

Moreover, the DNA encoding the polypeptide of SEQ ID NO: 6 means DNAs selected from the group of DNAs which are obtained by translating the amino acids of the polypeptide of SEQ ID NO: 6 to triplets in accordance with the genetic code. This group of DNAs includes the DNA of SEQ ID NO: 8.

DNAs encoding the fused proteins comprise codons corresponding to the amino acid sequence of the fused protein. The DNAs include but are not limited to the DNAs of SEQ ID NOs: 17 and 18.

The base sequence of SEQ ID No. 17 is the base sequence of the DNA coding for the fused protein of DHFR and the whole antigen polypeptide of 53 kDa of *Chlamydia pneumoniae* and the base sequence of SEQ ID No. 18 is the base sequence of the DNA coding for the fused protein of DHFR and (part of) the antigen polypeptide of 53 kDa of *Chlamydia pneumoniae*.

These DNA's can be manufactured by the method of chemical synthesis or the method of gene recombination.

Among the methods of chemical synthesis is counted the phosphoamidite method which fits the synthesis of a DNA formed in a length of not more than 100 base sequences. This chemical synthesis can be attained by a commercially available DNA synthesizing device.

Among the methods of gene recombination are counted a method for cloning the DNA from the elementary body of *Chlamydia pneumoniae* in the manner already described and the PCR method utilizing the already acquired DNA as a template and using a primer manufactured by adopting the base sequence at a position arbitrarily selected in that DNA. The method of gene recombination is capable of manufacturing a long DNA of more than 100 bases.

Now, the method for cloning the DNA coding for the antigen polypeptide from the elementary body of *Chlamydia pneumoniae* will be described in detail below.

Culture of *Chlamydia pneumoniae*

A suspension of cells is prepared from cultured HL cells. The supernatant of the culture is removed and the suspension of *Chlamydia pneumoniae* is then added to the resulting cell sheet. After incubation, *Chlamydia pneuminiae*-infected HL cells are obtained by centrifugation. As *Chlamydia pneumoniae*, strain YK41 (Y. Kanamoto et al., Micro biol. Immunol., Vol. 37, p.495–498, 1993) can be used.

Purification of Elementary Body of *Chlamydia pneumoniae*

The *Chlamydia pneuminiae*-infected HL cells are disrupted and centrifuged, thereby recovering the supernatant. The obtained supernatant is layered onto a continuous density gradient solution containing urografin (schering) is centrifuged.

The yellowish white band was recovered because in the preliminary experiment, it was confirmed to contain the elementary body of *Chlamydia pneumoniae* with the aid of an electron microscope.

Preparation of Genomic DNA of *Chlamydia pneumoniae*

The elementary body of *Chlamydia pneumoniae* is suspended in 10 mM Tris-HCl buffer (pH 8.0) containing 1 mM ethylene diaminetetra acetate (EDTA) (hereinafter referred to as "TE buffer"). To the resulting suspension are added a 1% aqueous solution of sodium dodecyl sulfate (SDS) and an aqueous solution of Proteinase K (1 mg/ml) and the elementary body is lysed while incubating. To the resulting solution is added phenol saturated with 0.1 M Tris-HCl buffer (pH 8.0). The mixture is stirred and centrifuged to recover an aqueous layer. The obtained aqueous layer is treated successively with RNase and phenol/chloroform/isoamyl alcohol, followed by ethanol precipitation. As a result, genomic DNA of *Chlamydia pneunomiae* is obtained.

Preparation of Genomic DNA Expression Library

The genomic DNA is digested with restriction enzymes AccI, HaeIII and AluI. The digest is treated with phenol/chloroform/isoamyl alcohol and subjected to ethanol precipitation to yield partially digested DNAs. To the partially digested DNAs are added a linker, adenosine 5'-triphosphate (hereinafter abbreviated to "ATP") and T4 ligase, thereby ligating the linker to the partially digested DNAs.

The linker-ligated partially digested DNAs are applied to a Chroma spin 6000 column in which the mobile phase is 10 mM Tris-HCl buffer containing 0.1 M NaCl and 1 mM EDTA. The eluate is collected and fractions containing 1–7 kbp DNA fragments are recovered. To the resulting fractions are added ATP and T4 polynucleotide kinase and a reaction is conducted to phosphorylate the 5' end of the DNA fragments. The reaction solution is treated with phenol/chloroform/isoamyl alcohol and subjected to ethanol precipitation to yield 5'-end-phosphorylated DNA fragments.

To the resulting DNA fragments are added λgt11 DNA preliminarily digested with restriction enzyme EcoRI, ATP and T4 ligase and a reaction is conducted. The resulting recombinant λgt11 DNA is packaged with a commercially available packaging kit to prepare a gemonic DNA expression library.

Cloning of DNA Encoding Antigenic Polypeptide

Cultured cells of *E. coli* strain Y1090r– are infected with the gemonic DNA expression library and incubated in an agar medium. A protein produced in the cells by the expression of the inserted DNA is transferred to a nitrocellulose filter immersed in an aqueous solution of isopropylthio-β-D-galactoside (IPTG). The filter is blocked with a bovine serum albumin and washed. The filter is then reacted with a *Chlamydia pneumoniae*-specific monoclonal antibody. As the *Chlamydia pneumoniae*-specific monoclonal antibody, AY6E2E8 and SCP53 can be used. A hybridoma cell line forming AY6E2E8 has been deposited with the National Institute of Bioscience and Human-Technology, the Agency of Industrial Science and Technology (1–3, Higashi 1 chome Tsukuba-shi Ibaraki-ken 305, Japan) as FERM BP-5154 under the terms of the Budapest Treaty. A hybridoma cell line forming SCP53 is disclosed in J. Clin. Microbil., Vol.132, p.583–588, 1994. After the reaction, the filter is washed and reacted with an anti-mouse IgG antibody labeled with an enzyme such as peroxidase or the like. After the reaction, the filter is washed and reacted with a color-developing substrate solution. As the color-developing substrate solution, a mixture of an aqueous solution of hydrogen peroxide and a solution of 4-chloro-1-naphthol in methanol can be used. After the reaction, the filter is washed and dried in air.

Plaques corresponding to the color-developing spots on the filter are identified and λ phage contained in the plaques is obtained. The above procedure is repeated until all the plaques react with the aforementioned monoclonal antibody. As a result, the DNA encoding an antigenic polypeptide is cloned and λ phage expressing the *Chlamydia pneumoniae*-specific antigenic polypeptide having reactivity with the *Chlamydia pneumoniae*-specific monochonal antibody is obtained.

Production of DNA Encoding the *Chlamydia pneumoniae*-Specific Antigenic Polypeptide

*E. coli* strain Y1090r− is infected with the obtained λ phage and cultured to yield a large amount of λ phage. DNA molecules are obtained and purified from the λ phage using a commercially available kit. To the obtained DNA molecules are added a primer, Taq polymerase and deoxynucleotides. The steps of heating, cooling and incubating are repeated, thereby amplifying the DNA molecule inserted in λgt11. λgt11 forward primer and λgt11 reverse primer (Takara Shuzo Co. Ltd.) can be used as primers and AmpliTaq DNA polymerase can be used as a Taq polymerase. A general procedure of DNA amplification is known as the PCR method, which is described in detail in J. Sambrook et al., Molecular Cloning, 2nd ed., Cold Spring Harbor Laboratory Press (1989) (hereinafter referred to as "Molecular Cloning").

The amplified DNA is obtained and its base sequence is determined and analyzed. The amplified DNA can be obtained with a commercially available kit such as Wizard PCR Prep kit (Promega). The base sequence can be determined by fluorescence-labeled terminator cycle sequencing using Taq polymerase. This sequencing can be performed with a kit commercially available from Perkin-Elmer Japan. For analysis of the base sequence, a commercially available apparatus such as Model 373A DNA Sequencer (Applied Biosystems) can be used.

Following the determination of the base sequence, the base sequence of the DNA is analyzed using a DNA sequencing software package such as DNASIS (Hitachi Software Engineering) to estimate an editing, junctional and amino acid-translational regions.

If it is found that a full-length gene has not been obtained, DNA molecules upstream and downstream of the available DNA are obtained by genome walking. The genome walking can be performed with a kit commercially available from Takara Shuzo Co., Ltd.

Preparation of DNA Encoding DHFR

DNA encoding DHFR is obtained by digesting the DNA with a restriction enzyme from a plasmid vector containing the DNA or by amplifying the DNA by PCR using a template plasmid DNA or genomic DNA containing the DNA with an appropriate primer.

In the former method, plasmid vector PBBK10MM and recombinant vector pCPN533T of the invention can be used as the plasmid vector containing DNA encoding DHFR. *E. coli* containing pCPN533T and *E. coli* containing pBBK10MM have been deposited with the National Institute of Bioscience and Human-Technology, the Agency of Industrial Science and Technology as FERM BP-5222 and FERM BP-2374, respectively. Plasmid pCPN533T can be obtained from the deposited *E. coli* by a conventional method for obtaining plasmid DNA, which is described in "Molecular Cloning". When plasmid pBBK10MM is used, a DNA fragment having a length of about 4.8 kbp may be excised with restriction enzymes BamHI and XhoI.

In the latter method, pBBK10MM and pCPN533T (see supra) can be used as a plasmid DNA and genomic DNA of *Bacillus subtilis* can be used as a genomic DNA. Genomic DNA can be obtained by a conventional method for obtaining gemonic DNA, which is described in "Molecular Cloning".

The primer to be used in the latter method can be designed and synthesized in consideration of base sequences at the 5' and 3' ends of DNA encoding DHFR. For example, an oligonucleotide having the 1–20 sequence in the base sequence of SEQ ID NO: 17 and one having a sequence complementary to the 461–480 sequence in the base sequence of SEQ ID NO: 5 can be used. These oligonucleotides can be synthesized chemically with a commercially available DNA synthesizer.

In the antigen polypeptides mentioned above, the polypeptide of SEQ ID NO. 1 containing the whole antigen polypeptide of 53 kDa of *Chlamydia pneumoniae* is particularly preferred.

Method of Production of Anti-*Chlamydia pneumoniae* Antibody by Using the Antigenic Polypeptide as Antigen An anti-*Chlamydia pneumoniae* antibody can be produced by immunizing a mouse with the antigenic polypeptide of the invention as an antigen, separating a spleen cell from the immunized mouse, fusing the spleen cell with a myeloma cell line to produce hybridomas, selecting a hybridoma recognizing the *Chlamydia pneumoniae* 53 kDa antigenic polypeptide from the produced hybridomas and culturing the selected hydridoma.

Exemplary myeloma cell lines include P3X63Ag8.653 (ATCC CRL-1580) and P3/NSI/1-Ag4-1 (ATCC TIB-18).

The anti-*Chlamydia pneumoniae* antibody is produced by a known general procedure for obtaining antibodies by immunization of mouse, except that the antigenic polypeptide of the invention is used as an antigen.

Method and Reagents for Detection and/or Measurement of Anti-*Chlamydia pneumoniae* Antibody Using the Antigenic Polypeptide as Antigen, and Agents for Diagnosis of *Chlamydia pneumoniae* Infections Comprising the Antigenic Polypeptide as Active Ingredient A method for detection and/or measurement of an anti-*Chlamydia pneumoniae* antibody comprises, for example, the steps of immobilizing the antigenic polypeptide on a support, applying a sample, washing, adding a labeled secondary antibody, washing and detecting and/or measuring the label either directly or indirectly.

Examples of the support include latex particles, cellulose threads, plastic assay plates and particles and the like.

The antigenic polypeptide may be immobilized on the support through covalent bonding or physical adsorption.

Examples of the sample include human sera and the like. It is preferred to block the surface of the support with bovine serum albumin or the like before the addition of a sample so as to insure that other antibodies in the sample will not bind to the support unspecifically.

The support is washed with a surfactant-containing phosphate buffer or the like.

An example of the labeled secondary antibody is a labeled anti-human monoclonal antibody. Useful labels include various kinds of enzymes such as alkaline phosphatase, luciferase, peroxidase, β-galactosidase and the like, various fluorescent compounds such as fluorescein and the like. A chemical compound such as biotin, avidin, streptoavidin, digoxigenin or the like may be inserted between the antibody and the label.

When the label is an enzyme, it may be detected and/or measured by adding a substrate and detecting and/or measuring the light emission or color development which occurs due to the catalytic action of the enzyme or by measuring the change in light absorbance. When the label is a fulorescent compound, it may be detected and/or measured by irradiating the reaction system with UV light and detecting and/or measuring the emitted fluorescence. A sensitizer may be used if necessary.

Reagents for detection and/or measurement of the anti-*Chlamydia pneumoniae* antibody using the antigenic polypeptide of interest as an antigen include the antigenic polypeptides which are immobilized on a support and those with which the necessary amounts of the secondary antibody and the substrate are enclosed.

The aforementioned reagents can be used as agents for diagnosis of *Chlamydia pneumoniae* infections.

Probes and Primers for Detection and/or Measurement of *Chlamydia pneumoniae* Gene DNA encoding the *Chlamydia pneumoniae* 53 kDa antigenic polypeptide has the base sequence of SEQ ID NO: 3.

The probes and primers of the invention comprise DNA containing any one of (a) a DNA containing a sequence of at least 10 consecutive bases in the DNA of SEQ ID NO: 3, (b) a DNA complementary to DNA (a), or (c) a DNA having at least 90% homology to DNA (a) or (b).

The length of the base sequence of the probes and primers is preferably 10–50 bp, more preferably 15–20 bp.

Specific examples of the probes and primers of the invention include a DNA comprising the base sequence of SEQ ID NO: 19 and a DNA comprising the base,sequence of SEQ ID NO: 20.

The probes and primers of the invention can be synthesized easily with a commercially available DNA synthesizer. DNA synthesizers are commercially available from Applied Biosystems and the like. Alternatively, the probes and primers of the invention can be prepared by chemically synthesizing a short DNA fragment and synthesizing a long DNA fragment by PCR using the short DNA as a primer.

The probes and primers of the invention include those prepared by labeling such DNAs.

Exemplary labels include chemical compounds such as biotin, avidin, streptoavidin, digoxigenin and the like; enzymes such as alkaline phosphatase, luciferase, peroxidase, β-galactosidase and the like; and fluorescent compounds such as fluorescein and the like. Biotin may be bound to the probes by, for example, adding biotinated deoxyuridine 5'-triphosphate to the probes in the presence of a terminal transferase. A kit containing a terminal transferase and biotinated deoxyuridine 5'-triphosphate can be purchased from Boehringer Mannheim. In the case where a label other than biotin is to be bound, a commercially available kit can also be used. Such a kit can be purchased from Takara Shuzo Co., Ltd and TOYOBO CO., LTD. Alternatively, the label may be bound by a method described in "Molecular Cloning".

If desired, radioactive isotopes can be used as labels. In this case, $(\gamma^{-32}P)dATP$ is added to the probes and primers in the presence of T4 polynucleotide kinase. A general procedure of labeling with a radioactive isotope is described in "Molecular Cloning". T4 polynucleotide kinase can be purchased from TOYOBO CO., LTD. and $(\gamma^{-32}P)dATP$ from Amersham.

RNAs corresponding to the base sequences of the probes and primers of the invention, that is, nucleic acids in which thymine is replaced with uracil in the base moiety and in which deoxyriboses are replaced with riboses in the sugar chain, can be used as the probes and primers of the invention instead of the aforementioned probes and primer comprising DNAs as structural units. These probes and primers comprising RNAS as structural units can be used in the method and reagents for detection and/or measurement of the invention.

Method for Detection and/or Measurement of *Chlamydia pneumoniae* Gene

*Chlamydia pneumoniae* gene is detected and/or measured by, for example, separating DNA in a sample on the basis of the difference in molecular weight by elecrophoresis, transferring the obtained DNA to a nitrocellulose filter, nylon membrane filter or the like for its identification, adding the labeled probe of the invention, and detecting and/or measuring the label. This method is called the Southern blotting technique and its general procedure is described in "Molecular Cloning".

*Chlamydia pneumoniae* gene is detected and/or measured with the primer of the invention by, for example, the PCR method which was described above. The method for detecting and/or measuring *Chlamydia pneumoniae* gene by PCR using the primer of the invention comprises the following steps.

(i) A buffer containing the primer of the invention, DNA polymerase, dATP, dCTP, dGTP and dTTP is added to a sample containing DNA and the mixture is heated.

(ii) The reaction solution is cooled, held at a constant temperature and heated.

(iii) Step (ii) is repeated.

(iv) The DNA contained in the reaction solution is detected and/or measured.

The DNA-containing sample to be used in step (i) may be nucleic acids as extracted from tunica mucosa pharyngsis of a patient.

The DNA polymerase to be used in step (i) may be a Taq polymerase, which can be purchased from TOYOBO CO., LTD.

In step (i), the mixture is heated by, for example, leaving it to stand at 90–100° C. for 0.5–10 minutes.

In step (ii), the reaction solution is cooled by, for example, leaving it to stand at 45–65° C. for 0.5–5 minutes, held at a constant temperature by, for example, at 70–80° C. for 1–10 minutes, heated by, for example, leaving it to stand at 90–100° C. for 0.5–5 minutes.

The heating in step (i), and cooling, holding at a constant temperature and heating in step (ii) can be carried out by using a DNA thermal cycler® (Perkin-Elmer Cetus).

Step (iii) may be repeated any number of times, preferably about 30 times.

The DNA contained in the reaction solution is detected and/or measured in step (iv) by, for example, electrophoresing the reaction solution with an agarose gel containing ethidium bromide, and thereby separating the DNA in the reaction solution on the basis of the difference in molecular weight and irradiating the agarose gel with UV light. If the primer of the invention is a labeled one, DNA is detected and/or measured with the aid of the label.

In another embodiment of the invention, after steps (i)–(iii), the primer of the invention may be replaced with one having another base sequence and steps (i)–(iii) are repeated, followed by step (iv).

Reagents for Detection and/or Measurement of *Chlamydia pneumoniae* Gene

An exemplary reagent for detection and/or measurement of *Chlamydia pneumoniae* gene according to the invention is an aqueous solution of the probe or primer of the invention which is packed frozen in a plastic container.

BEST MODE FOR CARRYING OUT THE INVENTION

Now, this invention will be described in detail below with reference to examples. It is to be distinctly understood that the invention is not limited in any sense to these examples.

Now, the component steps of the process from the culture of host cells of *Chlamydia pneumoniae* through the determination of gene DNA sequence/amino acid sequence of the antigenic poly-peptide of *Chlamydia pneumoniae* will be described below in the order of their occurrence.

EXAMPLE 1

Preparation of DNA Coding for 53K Antigenic Polypeptide Specific to *Chlamydia pneumoniae*

(A) Culture of Host Cells (HL Cells)

The HL cells cultured in advance confluently on the bottom surface of a plastic culture flask (75 $cm^2$) were washed with 5 ml of a magnesium-free (–) solution of a phosphate buffer physiological saline solution (hereinafter referred to as "PBS"), coated throughout on the entire surface thereof with 5 ml of a PBS containing 0.1% (w/v) trypsin, deprived of the excess solution, kept warmed at 37° C. for 10 minutes, and made to add 5 ml of a Dulbecco MEM culture medium containing 10% (v/v) bovine fetal serum. The HL cells adhering to the flask interior were removed by pipetting to obtain a cell suspension.

The culture in a plastic culture flask (75 $cm^2$) was implemented by charging the culture flask with 1 ml of the cell suspension mentioned above and 5 to 20 ml of the Dulbecco MEM culture medium containing 10% (v/v) bovine fetal serum and the culture in a 6-well plastic culture vessel was effected by placing in each of the six wells 4 ml of a mixed solution consisting of 8 ml of the cell suspension mentioned above and 292 ml of the Dulbecco MEM culture medium containing 10% bovine fetal serum and performing culture under an ambience containing 5% (v/v) carbon dioxide gas.

(B) Culture of *Chlamydia pneumoniae* YK41

From the culture solution of the HL cells propagated in a 6-well plastic culture vessel (on the bottom surface thereof), the supernatant was removed with a pipet. The residual cell sheet in the culture vessel, after adding 2 ml per well of the suspension of the YK41 strain of *Chlamydia pneumoniae* (Kanamoto et al., Microbiol. Immunol., Vol. 37, p.495–498, 1993) [the supernatant obtained by diluting a preserved solution of *Chlamydia pneumoniae* YK41 to 12 to 24 times the original volume with an aqueous solution containing 75 g of sucrose, 0.52 g of monopotassium phosphate, 1.22 g of dipotassium phosphate, and 0.72 g of glutamic acid liter (hereinafter referred to as "SPG"), treating the diluted solution with a supersonic wave for one minute, and subjecting the resultant diluted solution to centrifugal separation at 2,000 rpm for three minutes], was subjected to centrifugal adsorption at 2,000 rpm for one hour. After the centrifugal adsorption, the *Chlamydia pneumoniae* suspension was removed from the resultant cell sheet. The residual cell sheet, after adding 4 ml per well of a Dulbecco MEM culture medium containing 1 μg of cyclo-heximide per ml and 10% (v/v) of bovine fetal serum, was cultured at 36° C. for three days under an ambience containing 5% (v/v) carbon dioxide gas. After this culture, the cells adhering to the culture vessel were separated with a sterilized silicone blade and recovered. The cells were centrifuged at 8,000 rpm for 30 minutes. The sediment obtained consequently was resuspended in SPG and the resultant suspension was put to storage at –70° C.

(C) Purification of Elementary Body of *Chlamydia pneumoniae* YK41

The frozen suspension of HL cells infected with the *Chlamydia pneumoniae* YK41 preserved at –70° C. was melted and homogenized by the use of a homogenizer. The homogenate was centrifugally separated at 2,500 rpm for 10 minutes and the supernatant consequently formed was recovered. The sediment was again suspended in SPG and treated in the same manner as described above to recover a new supernatant. This procedure was repeated twice more. The successive supernatants were joined into one volume.

Separately, in a centrifuging tube, a 0.03M tris-hydrochloride buffer (pH 7.4) containing 50% (w/v) sucrose was placed, then a mixed solution of 3 parts by volume of urografin 76% (produced by Schering Corporation) with 7 parts by volume of 0.03M tris hydrochloride buffer (pH 7.4) was superposed, and subsequently the supernatant recovered as described above was attentively superposed on the layer of the mixed solution. The superposed layers in the centrifuging tube were centrifuged at 8,000 rpm for one hour. The layer of the 0.03M tris hydrochloride buffer (pH 7.4) containing 50% (w/v) sucrose and the sediment were recovered from the tube. The recovered solution and SPG added thereto in an equal volume were subjected to centrifugation at 10,000 rpm for 30 minutes. From the resultant separated phases, the supernatant was discarded and the sediment was suspended in SPG. In the centrifuging tubes, continuous density-gradient solutions consisting 35% to 50% of Urografin 76% (produced by Schering Corporation) in 0.03M tris hydrochloride buffer (pH 7.4) (ratios by volume of the former component to the total volume of solution) were placed and the suspension mentioned above was superposed thereon. The superposed layers in the tubes were centrifuged at 8,000 rpm for one hour. When a small amount of the yellowish white band was sampled and observed under an electron microscope, it was found to contain the elementary body of *Chlamydia pneumoniae*. So, this band was recovered and diluted with SPG to twice the original volume, and centrifuged at 10,000 rpm for 30 minutes. The sediment obtained in consequence of the centrifugation was suspended in SPG, assayed for protein concentration (with the aid of a protein analysis kit produced by Biorad Corp, with bovine serum albumin as a standard), and put to storage at –70° C.

(D) Preparation of Genome DNA of *Chlamydia pneumoniae* YK-41 Strain

Three hundred (300) μl of a suspension of the elementary body of the purified *Chlamydia pneumoniae* YK-41 strain mentioned above (protein concentration: 1.37 mg/ml) was centrifuged at 4° C. at 12,000 rpm for five minutes. The resultant sediment was suspended in 500 μl of 10 mM tris buffer (pH 8.0) containing 1 mm EDTA (hereinafter referred to as "TE buffer"). The same centrifugation was repeated and the resultant sediment was suspended in 300 μl of TE buffer. The produced suspension and 30 μl of an aqueous 2% SDS solution and 30 μl of an aqueous solution of 1 mg/ml proteinase K added thereto were incubated at 56° C. for 30 minutes to effect solution of the elementary body. The incubated solution and 350 µl of phenol-saturated 0.1M tris hydrochloride buffer (pH 8.0) added thereto were thoroughly stirred with a vortex mixer. The resultant mixture was centrifuged at 4° C. at 12,000 rpm for five minutes. From the separated layers, the aqueous layer was recovered (for extraction of DNA). This procedure of extraction was repeated once more. The aqueous layer and 2 µl of a 10 mg/ml RNase solution added thereto were incubated at 37° C. for two hours to effect decomposition of RNA. The incubated solution and 300 g µl of a mixed solution consisting of a phenol-saturated 0.1M tris-hydrochloride buffer (pH 8.0), chloroform, and isoamyl alcohol at a volumetric ratio of 25:24:1 (hereinafter referred to as "PCId") were thoroughly stirred with a vortex mixer. The resultant mixture was centrifuged at 4° C. at 12,000 rpm for five minutes. From the separated layers, the aqueous layer was recovered. This procedure was repeated until a fifth time.

One part by volume of the resultant solution and 1/10 part by volume of an aqueous 10M ammonium acetate solution and two parts by volume of ethanol added thereto were left standing for five minutes to effect precipitation of DNA. The resultant mixed solution was centrifuged at 4° C. at 12,000 rpm for five minutes. The sediment plus 600 µl of an aqueous 70% ethanol solution was thoroughly stirred and centrifuged at 4° C., at 12,000 rpm for five minutes to effect purification. This procedure was repeated twice more. The contents of the centrifuging tubes were left standing for 15 minutes with the lids of the tubes kept open to dry the sediment. The dry sediment was dissolved with 200 µl of TE and the resultant solution was put to storage at −20° C.

(E) Preparation of Genome DNA Expression Library

One hundred (100) µl of a genome DNA solution and 10 µl of a restriction endonuclease grade M-buffer and 10 µl of a restriction endonuclease mixed solution (obtained by mixing 0.4 µl each of AccI, Hae III, and 1/50 dilution AluI with 20 µl of TE) added thereto were left reacting at 37° C. for 20 minutes. The reaction time of 20 minutes mentioned above was a duration necessary for DNA to be decomposed into partially digested DNA fractions of sizes ranging from 1 kbp through 7 kbp. It was empirically found in advance by using a small amount of genome DNA. The resultant reaction solution and 100 µl of PCI added thereto were thoroughly stirred with a vortex mixer and the produced mixture was centrifuged at 4° C. at 12,000 rpm for five minutes. The aqueous phase was recovered from the separated layers consequently obtained. The recovered aqueous layer and 10 µl of an aqueous 3M sodium acetate solution and 220 µl of ethanol added thereto were left standing at −80° C. for 15 minutes to effect precipitation of partially digested DNA. The produced mixed solution was centrifuged at 4° C. at 12,000 rpm for five minutes. From the separated layers, the supernatant was discarded. The sediment was mixed with 600 µl of an aqueous 70% ethanol solution and the produced mixture was again centrifuged at 12,000 rpm for five minutes. The supernatant was discarded and the sediment was dried under a reduced pressure.

The partially digested DNA consequently obtained was dissolved in 20 µl of purified water. The amount 19 µl of the DNA solution and 14 µl of a linker (20 pmole/µl) represented by the following base sequence, 4.5 µl of 10 mM ATP, 4.5 µl of a 0.2M tris-hydrochloride buffer (pH 7.6; hereinafter referred to as "tenfold concentration ligation grade buffer") containing 50 mM MgCl$_2$, 50 mM dithiothreitol, and 500 µg/ml bovine serum albumin, 2 µl of purified water, and 1 µl of T4 ligase added thereto were left reacting at 160° C. for four hours to effect addition of the linker.

| 5'-AATTCGAACCCCTTCG-3' | (SEQ ID NO 32) |
| 3'-GCTTGGGGAAGCp-5' | (SEQ ID NO 33) |

The partially digested DNA adding the linker as described above was treated with a column (Chroma Spin 6000) using a 10 mM tris-hydrochloride buffer containing 0.1M NaCl and 1 mM EDTA as a migration phase. From the eluate, fractions each of two drops were separated. Each fraction was partly analyzed by 0.8% agarose gel electrophoresis to recover a fraction containing DNA segments of sizes from 1 kbp through 7 kbp. The amount 144 µl of the produced fraction and 13 µl of purified water, 20 µl of 10 mM ATP, 20 µl of a 0.5M tris-hydrochloride buffer (pH 7.6 maximum; hereinafter referred to as "tenfold concentration phosphorization grade buffer") containing 0.1M MgCl$_2$, 50 mM dithiothreitol, 1 mM spermidine hydrochloride, and 1 mM EDTA, and 3 µl of T4 polynucleotide kinase added thereto were left reacting at 37° C. for 30 minutes to effect phosphorization of the 5' terminal of the DNA fragment. The resultant reaction solution and 200 µl of PCI added thereto were thoroughly mixed by shaking. The produced mixture was centrifuged at 4° C. at 12,000 rpm for five minutes. From the separated layers, the aqueous layer was recovered. The aqueous phase was made to precipitate nucleotide by addition of 1 µl of an aqueous 20 mg/ml glycogen solution, 20 µl of an aqueous 3M sodium acetate solution, and 400 µl of ethanol. The produced solution was centrifuged at 4° C. at 12,000 rpm for 10 minutes. The supernatant was discarded. The sediment was mixed with 200 µl of 70% ethanol and again centrifuged. From the separated layers, the supernatant was discarded. The sediment was air dried and then dissolved in, 1 µl of purified water.

The amount 0.6 µl of the resultant aqueous solution and 1 µl of λgt11 DNA (1 µg/µl, produced by Stratagene Corp.) cleaved in advance with a restriction endonuclease EcoRI, 0.5 µl of a tenfold concentration ligation grade buffer, 0.5 µl of 10 mM ATP, 0.4 µl of T4 ligase, and 2 µl of purified water added thereto were left reacting overnight at 4° C. Then, the recombinant λgt11 DNA consequently obtained was packaged by the use of a packaging kit (produced by Stratagene Corp. and marketed under trademark designation of Gigapack II Gold").

(F) Production of *Chlamydia pneumoniae*-specific Monoclonal Antibody

Cultivation and Transfer of the Myeloma Cell Strain

The myeloma cell strain used for the production of the monoclonal antibody was P3/NSI/1-Ag 4-1 (ATCC TIB-18). It was incubated and subjected to successive transfer culture in the RPMI 1640 culture medium containing 10% (v/v) bovine fetal serum. Two weeks prior to the cell fusion, the strain was incubated for one week in the RPMI 1640 culture medium containing 0.13 mM of 8-azaguanine, 0.5 µg/ml of a mycoplasma expellant (produced by Dainippon Pharmaceutical Co., Ltd. and marketed under product code of "MC-210"), and 10% (v/v) bovine fetal serum and then it was incubated in a standard culture medium for one week.

Immunization of Mouse

Two hundred (200) µl of the suspension of the aforementioned elementary body having a protein concentration of 270 µg/ml was centrifuged at 12000 rpm for 10 minutes. The precipitate and 200 µl of PBS added thereto were together suspended. The suspension was emulsified by the addition of 100 µl of Freund'sadjuvant. A portion, 150 µl in volume, of the emulsion was hypodermally injected into the back of a mouse (0'th day of experiment). On the 14th, 34th, and 49th day, the suspension of the purified elementary body having a protein concentration of 270 µg/ml was intra-abdominally injected in a fixed dose of 100 µl into the mouse. Further, 50 µl of the suspension of the purified elementary body having a protein concentration of 800 µg/ml was intra-abdominally injected into the mouse on the 69th day and 100 μl of the same suspension was similarly injected into the mouse on the 92nd day. On the 95th day, the mouse was sacrificed to extract the spleen, which was put to use in the cell fusion.

Cell Fusion

In a round bottom glass tube, $10^8$ spleen cells obtained from the spleen of the immunized mouse and $10^7$ myeloma cells were thoroughly mixed and centrifuged at 1400 rpm for five minutes. The supernatant was removed and the remaining cells were further mixed thoroughly. The cells and 0.4 ml of the RPMI 1640 culture medium containing 30% (w/v) polyethylene glycol and kept in advance at 37° C. were together left standing at rest for 30 seconds. The resultant mixture was centrifuged at 700 rpm for six minutes. The glass tube containing this mixture and 10 ml of the RPMI 1640 culture medium added anew thereto was slowly rotated to ensure thorough dispersion of polyethylene glycol and centrifuged at 1400 rpm for five minutes. The supernatant was completely removed. The precipitate and 5 ml of the HAT culture medium added thereto were together left standing at rest for five minutes. The resultant mixture and 10–20 ml of the HAT culture medium added thereto were together left standing at rest for 30 minutes and then diluted by the addition of the HAT culture medium until the myeloma cell concentration reached $3.3\times10^5$/ml to suspend the cells. The suspension was dispensed two drops each to the wells of a 96-well plastic incubation vessel by the use of a Pasteur's pipet. The suspension was incubated in the atmosphere of 5% (v/v) carbon dioxide gas at 36° C. After one day, 7 days, and 14 days following the start of the incubation, the HAT culture medium was added one to two drops each to the wells.

Screening of Antibody-producing Cells

The purified elementary body of the Chlamydia pneumoniae YK 41 strain was solubilized with 1% (w/v) SDS, dialyzed against a 0.05M sodium bicarbonate buffer solution (pH 9.6) containing 0.02% of sodium azide, diluted until the protein concentration reached a level in the range of 1–10 μg/ml, dispensed 50 μl each to the wells of a 96-well EIA grade plate made of vinyl chloride, and left standing at rest overnight at 40° C. to induce adsorption of the antigen. The supernatant was removed. 150 μl of the PBS containing 0.02% (w/v) Tween 20 was added to the wells and the plate was left standing at rest for three minutes. The wells were deprived of the PBS and cleaned. After the wells were given a cleaning treatment once more, 100 μl of the PBS containing 1% (v/v) bovine serum albumin was added to the wells and left standing at rest overnight at 4° C. to effect blocking. The wells were deprived of the PBS containing the bovine serum albumin, cleaned twice in the same manner as above with the PBS containing 0.02% (w/v) Tween 20 and, after adding 50 μl of the culture supernatant of the fused cells, left at rest at room temperature for two hours. The wells were cleaned three times in the same manner as above with the PBS containing 0.02% (w/v) Tween 20 and, after adding 50 μl of the goat anti-mouse IgG antibody (25 ng/ml) labeled with peroxidase, left standing at rest at room temperature for two hours. The wells were cleaned three times in the same manner as above with the PBS containing 0.02% (w/v) Tween 20 and, after adding 50 μl of the ABTS solution (produced by KPL Corp.), left standing at rest at room temperature for 15 minutes—one hour to induce a coloring reaction. The contents of the wells were tested for absorbance at 405 nm by the use of a 96-well EIA plate grade photometer.

As a result, positive wells were detected and the supernatants of culture broth in these wells were found to contain an antibody capable of reacting the elementary body. The cells in these wells were recovered severally with the Pasteur's pipet, transferred to a 24-well plastic incubation vessel and, after adding 1–2 ml of the HAT culture medium, incubated in the same manner as above.

Cloning by Limiting Dilution Method

The fused cells propagated in the 24-well plastic incubation vessel were tested for cell concentration and diluted with the HT culture medium to adjust the number of cells to 20/ml. Separately, the thymocytes of 4- to 6-week old mice suspended in the HT culture medium were dispensed to a 96-well plastic culture vessel at a rate of $2\times10^5$/well and, after adding the aforementioned fused cells (cell concentration 20/ml) at a rate of 50 μl/well, incubated in an atmosphere of 5% (v/v) carbon dioxide gas at 36° C. After 1 day, 7 days, and 14 days following the start of the incubation, the HT culture medium was added to the culture vessel at a rate of 1 to two drops/well. From the wells observed to have propagated cells, the supernatant of the culture broth was recovered in a fixed volume of 50 μl per well and then analyzed in the same manner as above to confirm the production of an antibody.

From the wells in which only one cell colony was present, cells producing an antibody able to react with the elementary body and showing quick propagation were recovered and allowed to continue propagation in a 24-well plastic culture vessel. The same cloning procedure was repeated until a hybridoma AY6E2E8 was ultimately obtained.

Production of Monoclonal Antibody

The hybridoma AY6E2E8 was cultured in a 75 $cm^2$ plastic cell culture flask holding therein 20 ml of the RPMI 1640 culture medium containing 10% (v/v) bovine fetal serum. From the culture broth formed in the flask, a sample, 16–18 ml in volume, was extracted at intervals of three to four days. The residual culture broth was meanwhile replenished to a total volume of 20 ml with a fresh supply of the RPMI 1640 culture medium containing 10% (v/v) bovine fetal serum. Thus, the subculture of the hybridoma was continued. The samples extracted from the culture broth were centrifuged at 1200 rpm for five minutes to recover the supernatant (the culture supernatant containing the monoclonal antibody).

To a Balb/c mouse which had received intra-abdominal injection of 0.5 ml of pristane two weeks in advance of the experiment, the hybridoma strain suspended in the PBS at a concentration of $1–5\times10^6$/ml was intra-abdominally injected in a volume of 1 ml. After three weeks thence, the ascites was recovered from the Balb/c mouse and centrifuged at 1200 rpm for five minutes to recover the supernatant (ascites containing the monoclonal antibody).

Identification of Subclass of Monoclonal Antibody

The subclass of the monoclonal antibody was identified with the ISOTYPE Ab-STAT (produced by Sang Stat Medical Corp.). As a result, the subclass of the monoclonal antibody produced by the hybridoma AY6E2E8 was identified to be IgG2b.

Purification of Monoclonal Antibody

The monoclonal antibody produced by the hybridoma AY6E2E8 was purified as follows. A mixture of 1 part by volume of the monoclonal antibody-containing ascites obtained by injecting the hybridoma AY6E2E8 intra-abdominally to the mouse with 3 parts by volume of PBS was centrifuged at 3000 rpm for ten minutes. The resultant supernatant was passed through a filter, 0.22 μm in pore size. The filtrate was purified by the HPLC using Chromatop Superprotein A Column (4.6 mm Diam.×100 mm, produced by NGK Insulators Ltd. This column was equilibrated with the PBS in advance of the treatment.

A sample, 1 ml in volume, of the filtrate emanating from the 0.22 μm filter was injected into the column. The column was washed by passing the PBS first at a flow rate of 1 ml/min for three minutes and then at a flow rate of 5 ml/min for four minutes. The monoclonal antibody adsorbed on the column was eluted by passing a solution of 8.77 g of NaCl, 16.7 g of citric acid (monohydrate), and 14.72 g of Na2HPO4.12H2O in 1 liter of purified water through the interior of the column at a flow rate of 2 ml/min for five minutes. The fractions of the desorbed monoclonal antibody were gathered and diluted with a TTBS solution.

The elementary body of *Chlamydia pnuemoniae* was dissolved to obtain the peptide contained in the elementary body. The peptide and the monoclonal antibody mentioned above were subjected to the Western blotting to determine the specificity of the acquired monoclonal antibody.

As a result, the acquired monoclonal antibody was found to be capable of recognizing the *Chlamydia pneumoniae* 53 kDa antigen polypeptide.

A hybridoma 70 was acquired in the same manner as the hybridoma AY6E2E8. When the monoclonal antibody producing the hybridoma 70 was tested for specificity by following the procedure described above, it was found that this monoclonal antibody was capable of recognizing the *Chlamydia pneumoniae* 73 kDa antigen polypeptide.

When the monoclonal antibody produced by the hybridoma 70 was examined in the same manner as above by way of identification of subclass, the subclass of this antibody was found to be IgG.

(G) Cloning of DNA Coding for Antigenic Polypeptide

One platinum loop full of the Y1090r-strain of *Escherichia coli* was inoculated to an LB (containing 5 g of NaCl, 10 g of polypeptone, and 5 g of yeast extract per liter of water) culture medium containing 0.2% maltose and 50 μg/ml of ampicillin and shaken cultured at 37° C. overnight. The resultant culture solution was centrifuged at 2,000 rpm for 10 minutes. The sediment (*Escherichia coli*) was mixed with 9 ml of an aqueous 10 mM MgSO 4 solution. The amount 0.35 ml of the *Escherichia coli* suspension and 0.1 to 10 μl of the λgt11 (DNA library) suspension added thereto were incubated at 37° C. for 20 minutes to infect the *Escherichia coli* with λgt11. The λgt11-infected *Escherichia coli* mentioned above was added to 2.5 ml of a liquid LB agar culture medium kept warmed in advance at 47° C. and the resultant mixture was scattered on an LB agar culture medium. After the upper-layer culture medium was solidified, the entire culture medium was cultured at 42° C. for three to four hours. At the time that a plaque was observed, a nitrocellulose filter (containing perforations 82 mm in diameter) immersed in advance in an aqueous 10 mM IPTG solution was mounted in the upper-layer agar culture medium. Then, the whole culture medium was cultured at 37° C. for 12 hours. With a syringe having the tip of the nozzle thereof smeared with black ink, the filter was pierced at three asymmetrical points selected as marks on the filter. Then, the filter now bearing the marks of the black ink was extracted from the agar culture medium and washed three times with a 20 mM tris-hydrochloride buffer (pH 7.5) containing 150 mM NaCl and 0.1% Tween 20 (hereinafter referred to as "TTBS buffer"). The residual agar culture medium was put to storage in a refrigerator.

The filter was immersed in a 0.1% bovine serum albumin-containing solution of a 20 mM tris-hydrochloride buffer (pH 7.5) containing 150 mM NaCl (hereinafter referred to as "TBS buffer") and shaken at 37° C. for one hour to effect a blocking reaction thereon. Then, the filter was washed twice with the TTBS buffer, immersed in the 10 μg/ml TTBS solution of a monoclonal antibody specific to *Chlamydia pneumoniae*, and shaken at 37° C. for one hour. The filter was washed three times with the TTBS buffer and then shaken in a peroxidase-labelled anti-mouse IgG antibody solution (TTBS buffer, 50 ng/ml) at 37° C. for one hour. The filter was washed three times with the TTBS buffer and three times with the TBS buffer, then immersed in a color ground substance solution (prepared by adding 60 μl of an aqueous 30% hydrogen peroxide solution and 20 ml of a methanolic 0.3% 4-chloro-1-naphthol solution to 100 ml of the TBS buffer), and left standing therein at room temperature for about 30 minutes. At the time that the filter was thoroughly colored, this filter was extracted from the solution, washed with purified water, and air-dried.

The plaques formed on the agar culture medium at the positions corresponding to the colored spots on the filter were searched out and identified. The relevant portions of the agar were pierced with a Pasteur pipet to recover the plaques. Each recovered plaque was placed in a 50 mM tris-hydrochloride buffer (pH 7.5) containing 0.1 M NaCl, 8 mM magnesium sulfate, and 0.01% gelatin (hereinafter referred to as "SM buffer") and one drop of chloroform, and left standing therein at 4° C. overnight to effect extraction of the λ phage from the plaque. The procedure just described was repeated until the plaque wholly reacted with the monoclonal antibody mentioned above to obtain a clone of the DNA coding for the antigen polypeptide.

As a result, the λ phage which expressed a *Chlamydia pneumoniae*-specific antigen polypeptide reactive with a *Chlamydia pneumoniae*-specific monoclonal antibody was obtained and designated as 53-3S λ phage.

(H) Culture of 53-3S λ Phage and Purification of DNA

Plaques were formed by following the procedure described in (F) above. One of the plaques was recovered, placed in 100 μl of the SM buffer, and left standing therein at 4° C. overnight to effect extraction of the λ phage. In the LB culture medium in which 250 μl of the Y1090r– strain of *Escherichia coli* was cultured overnight, 5 to 10 μl of the λ phage solution was placed and left standing therein at 37° C. for 20 minutes to effect infection of the *Escherichia coli* with the λ phage. The infected *Escherichia coli* was inoculated to 50 ml of the LB culture medium containing 10 mM magnesium sulfate and kept warm in advance at 37° C. and shaken cultured therein at 37° C. for five to seven hours until the bacteriolysis of the *Escherichia coli* by the λ phage occurred. The resultant culture solution, after adding 250 μl of chloroform, was centrifuged at 3,000 rpm for 10 minutes to effect removal of the residual cells of *Escherichia coli* and obtain a suspension of the λ phage. The λ phage DNA was purified by the use of a special device (produced by Promega Corp. and marketed under trademark designation of "Wizard λ Preps Kit").

(I) Amplification of DNA Coding for *Chlamydia pneumoniae* Antigenic Polypeptide A 600 μl grade microtube was charged with 61.5 μl of purified water, 10 μl of a tenfold concentration of reaction buffer (a tris-hydrochloride buffer, pH 8.3, containing 500 mM KCl, 15 mM MgCl$_2$, and 0.01% gelatin), 1 μl of 20 mM dNTP, 0.1 μl of 53-3S λ phage DNA solution, 1 μl of 20 nM λgt11 forward primer (produced by Takara Shuzo Co., Ltd.), 1 μl of 20 nM λgt11 reverse primer (produced by Takara Shuzo Co., Ltd.), and 0.5 μl of AmpliTaq DNA Polymerase, with two or three drops of mineral oil placed to form a top layer. The contents of the microtube were subjected to 30 circles of incubation, each consisting of 30 seconds' standing at 94° C., 30 seconds' standing at 55° C., and two minutes' standing at 73° C. to effect amplification of the DNA. After the reaction, the reaction solution was subjected to 1.2% low-melting temperature agarose gel electrophoresis to excise the amplified DNA. This amplified DNA was purified by the use of "Wizard PCR Prep Kit" (produced by Promega Corp.).

(J) Analysis for DNA Base Sequence

The analysis of the DNA for base sequence was effected by subjecting a sample to a sequence reaction in accordance with the fluorescence-labelled terminator cycle sequence method using a Taq DNA polymerase with a PCR-amplified DNA as a template and analyzing the reaction product by a DNA sequencer (produced by Applied Biosystems Corp. and marketed under product code of "Model 373A"). The DNA base sequence consequently obtained was examined by the gene sequence analysis soft (produced by Hitachi Software Engineering Co., Ltd. and marketed under trademark designation of "DNASIS") to estimate agglutination, ligation, and amino acid translation region. Consequently, the sequence was identified as SEQ ID No: 9.

The results of the analysis of the sequence of SEQ ID No: 9 show that about 60% of the amino acid sequence of the 53 KDa antigenic polypeptide from the N terminal thereof toward the C terminal was elucidated.

The DNA which codes for the *Chlamydia pneumoniae* antigen polypeptide is specific to *Chlamydia pneumoniae* and it has been cloned by utilizing a monoclonal antibody recognizing the 53 Kda antigen polypeptide. Thus, this DNA apparently encodes the 53 kDa antigen polypeptide.

The search for homology of both the base sequence and the amino acid sequence of SEQ ID No: 9 was carried out in accordance with the GenBank data base confirmed absence of a known series exhibiting high homology.

EXAMPLE 2

Preparation of Recombinant Vector Containing DNA Coding for Polypeptide Containing Part of Antigenic Polypeptide of *Chlamydia pneumoniae*, and Preparation of Transformant Carrying the Vector.

Though the acquired DNA evidently coded for the 53 KDa antigen polypeptide as mentioned above, it was expressed as shown below to determine whether or not it would react with the antibody mentioned above by way of precaution.

A plasmid pBBK10MM was severed with restriction enzymes of BamHI and XhoI and subjected to 1.2% low melting temperature solution agarose gel electrophoresis to excise about 4.6 Kbp of DNA fragment. This fragment was purified. The synthetic DNA's of SEQ ID No: 11 and SEQ ID No: 12 were added each in an amount of 1 ng to 100 ng of the DNA fragment and they were ligated by the use of a DNA ligation kit (produced by Takara Shuzo Co., Ltd.) The resultant reaction product was placed in an *Escherichia coli* HB101 strain-competent cell (produced by Takara Shuzo Co., Ltd.) to prepare a transformant and acquire a plasmid, which was designated as pADA431. This plasmid was severed with a restriction enzyme MunI and then subjected to an alkali phosphatase reaction to effect removal of the 5' phosphoric acid base.

Separately, the 53-3S λ phage DNA was severed with a restriction enzyme EcoRI. One hundred (100) ng of the pADA431 plasmid DNA severed with the restriction enzyme MunI mentioned above was added to 50 ng of the DNA fragment and they were ligated in the same manner as described above to prepare a transformant and acquire a plasmid incorporating therein the restriction enzyme EcoRI fragment of 53-3S λ phage DNA, which was designated as pCPN533 α. This plasmid was a DNA of a length of about 5.7 kbp possessing a base sequence of SEQ ID No: 10 and was capable of expressing the polypeptide containing part of 53K antigenic polypeptide with a host *Escherichia coli*. The base sequence of the DNA coding for the polypeptide containing part of the 53K antigenic polypeptide was shown by SEQ ID No: 4. The amino acid sequence deduced from this base sequence was shown by SEQ ID No: 2. An *Escherichia coli* carrying the plasmid pCPN533a was subjected to culture, electrophoresis, transfer to a nitrocellulose membrane, and detection with a monoclonal antibody in the same manner as described above. As a result, the occurrence of a colored band corresponding to the polypeptide mentioned above was visually conformed. This fact indicates that the *Escherichia coli* carrying the plasmid pCPN533a expressed the 53K antigenic polypeptide capable of reacting with a monoclonal antibody specifically reactive with *Chlamydia pneumoniae.*

EXAMPLE 3

Acquisition of DNA Coding for the Entire 53 KDa Antigenic Polypeptide of *Chlamydia pneumoniae*

A DNA possessing base sequences of SEQ ID Nos. 26 and 27 was synthesized based on the base sequence of SEQ ID No. 9 by the use of a DNA synthesizing device.

Ten (10) μl of the aqueous solution of genome DNA of the *Chlamydia pneumoniae* YK 41 strain (DNA content: about 1 μg) obtained in Example 1 and 5 μl of a K buffer concentrated to 1/10 times the original volume, 35 μl of purified water, and 5 μl of a limiting enzyme Hind III (19 U/μl) added thereto were kept together at 37° C. for three hours.

The resultant reaction solution was extracted from phenol. The extract and ethanol added thereto were together centrifuged to obtain a precipitate. This precipitate and 5 μl of the Hind III cassette DNA (20 ng/μl) in the PCR in vitro Cloning Kit (proprietary designation of Takara Shuzo Co., Ltd.) and 15 μl of ligation solution added thereto were kept together at 16° C. for 30 minutes.

The resultant reaction solution was extracted from phenol. The extract and ethanol added thereto are centrifuged together to acquire a precipitate. This precipitate was dissolved in 10 μl of purified water.

The resultant solution and 78.5 μl of purified water, 10 μl of a PCR grade buffer concentrated to 1/10 times the original volume, 8 μl of 2.5 mM dNTP, and 0.5 μl (5 U/μl) of Taq polymerase added thereto and 1 μl of a DNA possessing the base sequence of SEQ ID No. 26 (20 pmol/μl) and 1 μl of a DNA possessing the base sequence of SED ID No. 28 (20 pmol/μl) (enclosed as Primer Cl in the aforementioned kit) further added thereto as primer DNA's were placed together in a microtube, 0.6 ml in volume, with two drops of mineral oil superposed on the resultant mixture in the microtube. The mixture was subjected to 30 temperature cycles each consisting of 30 seconds at 94° C., 2 minutes at 55° C., and 3 minutes at 72° C. This procedure will be referred to hereinafter as "PCR process."

One (1) μl of the reaction solution resulting from the PCR process and 1 μl of a DNA possessing the base sequence of SEQ ID No. 27 (20 pmol/μl) and 1 μl of a DNA possessing the base sequence of SED ID No. 29 (20 pmol/μl) (enclosed as Primer C2 in the aforementioned kit) added thereto as primer DNA's were subjected to the PCR process.

The reaction solution resulting from the second PCR process was subjected to electrophoresis with 1.2% low melting agarose gel to separate an agarose gel containing a DNA, about 1.4 kbp in size. The Wizard PCR Prep kit (Promega Corp) was used for the purification of the DNA. The separated agarose gel and the buffer solution enclosed in the kit were together heated to dissolve the agarose gel. The purifying resin enclosed in the kit was added to the resultant solution to adsorb the DNA. The resultant mixture was centrifuged to obtain the purifying resin as a precipitate. The precipitate was washed with propanol and centrifuged again to obtain a precipitate. Purifying water was added to the precipitate to dissolve the DNA out of the purifying resin. The resultant mixture was centrifuged to obtain a supernatant (aqueous DNA solution). The process described above will be referred to herein below as "DNA purifying process."

The acquired aqueous DNA solution was caused to undergo a sequence reaction by the fluorescence-labeled terminator sequence method using the Taq DNA polymerase templated by the contained DNA and was analyzed for the base sequence of DNA with a DNA sequencer, Model 373A, (Applied Biosystems Corp.). The DNA base sequence consequently obtained was compiled and ligated by the software for gene sequence analysis (produced by Hitachi Software Engineering Co., Ltd. and marketed under trademark designation of "DNASIS") to estimate the amino acid translation region. The process just described will be referred to herein below as "base sequence analyzing process."

When the acquired DNA was analyzed for base sequence, it was found that this DNA possessed about 50 bp of base sequences on the 3' terminal side of the DNA encoding the antigen polypeptide of *Chlamydia pneumoniae* acquired in Example 1. It was further found that about 0.7 kb of coding region containing a stop codon existed on the downstream side of the base sequence.

A DNA possessing the base sequence of SEQ ID No. 30 was synthesized as a primer corresponding to the upstream part of the DNA encoding the antigen polypeptide of *Chlamydia pneumoniae* based on the base sequence of SEQ ID No. 9 and a DNA possessing the base sequence of SEQ ID No. 31 was synthesized as a primer corresponding to the downstream part of the DNA encoding the antigen polypeptide of *Chlamydia pneumoniae* based on the base sequence containing the aforementioned about 0.7 kb of code zone severally by the use of the DNA synthesizer.

The PCR process was performed on 1 µl of the DNA possessing the base sequence of SEQ ID No. 30 DNA and 1 µl of the DNA possessing the base sequence of SEQ ID No. 31 as a primer DNA by using 1 µl of the aqueous solution of the genome DNA of the *Chlamydia pneumoniae* YK 41 strain obtained in Example 1.

The DNA purifying process mentioned above was carried out on the reaction solution resulting from the third round of the PCR process to obtain about 1.5 kbp of DNA.

The base sequence analyzing process mentioned above was carried out on the acquired aqueous solution of DNA.

When the base sequence of the acquired DNA was analyzed, it was found that this DNA possessed the base sequence of SEQ ID No. 3 and encoded the amino acid sequence of SEQ ID No. 1.

DNA coding for the entire 53 KDa antigenic polypeptide of *Chlamydia pneumoniae* was obtained by effecting a genome walking by the use of the plasmid pCPN533a and the DNA library of λgt11.

EXAMPLE 4

Preparation of Recombinant Vector Containing DNA Coding for Entire 53 KDa Antigenic Polypeptide of *Chlamydia pneumoniae* and Preparation of Transformant Carrying the Vector The recombination vector containing the DNA coding for the whole *Chlamydia pneumoniae* 53 kDa antigen polypeptide and the transformant containing the vector can be manufactured as follows.

A recombinant vector containing a DNA coding for the entire 53 KDa antigenic polypeptide of *Chlamydia pneumoniae* and a transformant carrying the vector are prepared by following the procedure of Example 2 using the DNA coding for the entire 53 KDa antigenic polypeptide of *Chlamydia pneumoniae*.

EXAMPLE 5

Preparation of DNA Coding for 73K Antigenic Polypeptide of *Chlamydia pneumoniae*

A hybridoma 70 was acquired by the same method as used for the acquisition of a hybridoma AY6E2E8. The murine ascites was acquired by using the hybridoma 70. The supernatant of the ascites was analyzed for the quality of the monoclonal antibody contained therein. The results of this analysis indicate that this monoclonal antibody was specific to the antigen polypeptide of 73 KDa of *Chlamydia pneumoniae*.

A clone 70-2S λ phage was obtained by following the procedure of Example 1 while using a monoclonal antibody 70 in the place of the monoclonal antibody SCP53 or AY6E2E8. From the phage, a sequence of SEQ ID No: 13 was obtained.

The results of the analysis of the sequence of SEQ ID No: 13 clearly indicate that about 90% of the amino acid sequence of the 73K antigenic protein of *Chlamydia pneumoniae* from the N terminal toward the C terminal thereof was clarified.

The search for homology of both the base sequence and the amino acid sequence of SEQ ID No: 13 was effected in accordance with the GenBank data base. The results of the search clearly show that these sequences exhibited high homology with the gene base sequence isolated from *Chlamydia trachomatis* [L. M. Sardinia et al: J. Bacteriol., Vol. 17., 335–341 (1989)].

EXAMPLE 6

Production of anti-*Chlamydia pneumoniae* Antibody Using Antigenic Polypeptide of *Chlamydia pneumoniae* as Antigen The anti-*Chlamydia pneumoniae* antibody can be produced by using the antigen polypeptide of *Chlamydia pneumoniae* as follows.

(A) Culture and Passage of Myeloma Cell Strain

As a myeloma cell strain, P3X63Ag8.653 (ATCC CRL-1580) is cultured and passed in a RPMI1640 culture medium containing 10% (v/v) bovine fetal serum. Two weeks before the strain is subjected to cellular fusion, this strain is cultured for one week in the RPMI1640 culture medium containing 0.13 mM of 8-azaguanine, 0.5 µg/ml of a mycoplasma removing agent (produced by Dainippon Pharmaceutical Co., Ltd. and marketed under product code of "MC-210"), and 10% (v/v) bovine fetal serum. The subsequent one week is spent for culture in an ordinary culture medium.

(B) Immunization of Mouse

The amount 200 µl of a solution of the antigenic polypeptide mentioned above and having a protein concentration of 270 µg/ml is emulsified by addition of 200 µl of a Freund's complete adjuvant. The produced emulsion is hypodermically injected in an amount of 150 µl into the back of a mouse (the date of this injection reckoned as 0th day). On the 14th day, 34th day, and 49th day, 100 µl of a suspension of the antigenic polypeptide having a protein concentration of 270 µg/ml is intraabdominally injected into the mouse. Further, 50 µl of a suspension of the same antigenic polypeptide having a protein concentration of 800 µg/ml is intraabdominally injected into the mouse on the 69th day and 100 µl of the same suspension injected intraabdominally to the mouse on the 92nd day. On the 95th day, the mouse is sacrificed to extract the spleen. This spleen is utilized for cellular fusion.

(C) Cellular Fusion

In a round-bottom glass tube, $10^8$ splenic cells obtained from the spleen mentioned above and $10^7$ myeloma cells are thoroughly mixed. The resultant mixture is centrifuged at 1,400 rpm for five minutes and, with the consequently formed supernatant removed therefrom, further mixed thoroughly. The produced mixture is added to 0.4 ml of a RPMI1640 culture medium containing 30% (w/v) polyethylene glycol and kept warmed in advance at 37° C. and left standing therein for 30 seconds. The culture medium now containing the mixture is centrifuged at 700 rpm for six minutes. The glass tube, after adding 10 ml of the RPMI1640 culture medium, is gently rotated so as to permit thorough mixture of the polyethylene glycol. The mixture is then centrifuged at 1,400 rpm for five minutes. The supernatant consequently formed is thoroughly removed. The sediment and 6 ml of the HAT culture medium added thereto are left standing for five minutes. The resultant mixture and 10 to 20 ml of the HAT culture medium added thereto are left standing for 30 minutes. The HAT culture medium is further added thereto in such an amount as to set a myeloma cell concentration at $3.3 \times 10^5$/ml to obtain a suspension of cells. The suspension is dispensed at a rate of two drops to each of the 96-well plastic culture vessel by the use of a Pasteur pipet. The suspension is-cultured under an ambience of 5% (v/v) carbon dioxide gas at 36° C. Then, one or two drops of the HAT culture medium are added to each of the wells after the elapse of one day, seven days, and 14 days.

(D) Screening of Antibody-Producing Cells

The antigenic polypeptide mentioned above is suspended in a 0.05M sodium bicarbonate suspension (pH 9.6) containing 0.02% (w/v) sodium azide so as to set the protein concentration in the range of from 1 to 10 µg/ml. The resultant suspension is dialyzed against a 0.5M sodium bicarbonate buffer (pH 9.6) containing 0.02% of sodium azide. The dialyzate is diluted so as to set the protein concentration in the range of from 1 to 10 µg/ml. The diluted dialyzate is dispensed at a rate of 50 µl to each of the wells of a 96-well plate for EIA made of vinylchloride and left standing therein at 4° C. overnight to effect adsorption of the antigen. The supernatant consequently formed is removed from the wells. To each of the wells, 150 µl of PBS containing 0.02% (w/v) Tween 20 is added, left standing therein for three minutes, then removed, and washed. The washing is repeated once more. To the well, 100 µl of PBS containing 1% (v/v) bovine serum albumin is added and left standing at 4° C. overnight to effect blocking. The PBS containing the bovine serum albumin is removed and then washed twice more with the PBS containing 0.02% (w/v) Tween 20 in the same manner as described above. Then, 50 µg 1 of the culture supernatant of fused cells is added to the well and left standing therein at room temperature for two hours. The well is washed three times with the PBS containing 0.02% (w/v) Tween 20 in the same manner as described above. In the well, 50 µl of a goat anti-mouse IgG antibody labelled with peroxidase (25 ng/ml) is placed and left standing at room temperature. The well is washed three times with the PBS containing 0.02% (w/v) Tween 20 in the same manner as described above. In the well, 50 µl of an ABTS solution (produced by KPL Corp.) is placed and left standing at room temperature for 15 minutes to one hour to effect a reaction of coloration. The culture solution in the well is tested for absorbance at 405 nm with the photometer for 96-well EIA plate. The cells in the positive wells are severally recovered with the Pasteur pipet, transferred into a 24-well plastic culture vessel and, after adding 1 to 2 ml of the HAT culture medium, cultured in the same manner as described above.

(E) Cloning by Limiting Dilution Method

The fused cells of two strains propagated in a 24-well plastic culture vessel are tested for cell concentration and severally diluted with a HT culture medium until the number of cells decreased to 20/ml. Separately, the thymocytes of four– to six-weeks old mice suspended in the HT culture medium are dispensed at a rate of 1 to $2 \times 10^5$/well to a 96-well plastic culture vessel and the fused cells mentioned above (cell concentration 20/ml) are dispensed at a rate of 50 g µl/well to the same culture vessel and cultured under an ambience of 5% (v/v) carbon dioxide gas at 36° C. One day, seven days, and 14 days thereafter, the HT culture medium is added thereto at a rate of one to two drops per well. From each of the wells in which the growth of cells is observed, the culture supernatant is recovered in a fixed amount of 50 µl. This supernatant is analyzed in the same manner as in (D) titled "Screening of antibody-producing cells" to confirm the production of an antibody therein.

The cells which allowed the occurrence of a single cellular colony in a well, produced an antibody capable of reacting with an elementary body, and achieved quick proliferation are recovered from the relevant wells and are subsequently proliferated in a 24-well plastic culture vessel. Further, a hybridoma producing an anti-*Chlamydia pneumoniae* antibody is obtained by repeating the same cloning process as described above. This hybridoma is cultured and the anti-*Chlamydia pneumoniae* antibody is produced from the resultant culture supernatant.

EXAMPLE 7

Detection and Determination of anti-*Chlamydia pneumoniae* Antibody Using an Antigenic Polypeptide as an Antigen The anti-*Chlamydia pneumoniae* antibody can be detected and measured by using the antigen polypeptide of this invention as an antigen as follows.

The polypeptide formed of the amino acid sequence of SEQ ID No: 1 is used as an antigenic polypeptide. It is fixed on a microtiter plate, made to add a PBS containing bovine serum albumin, and left standing overnight at 4° C. to effect blocking. The PBS containing the bovine serum albumin was removed and the well is washed twice with the PBS containing 0.02% (w/v) Tween 20. The blood serum from a patient is added to the well thereto and is left standing at room temperature for two hours. The resultant solution is removed and the well is washed three times with the PBS containing 0.02% (w/v) Tween 20 in the same manner as described above. In each of the wells, a peroxidase-labelled mouse anti-human IgG antibody is placed and left standing at room temperature for two hours. The solution in the well is removed and the well is washed three times with the PBS containing 0.02% (w/v) Tween 20 in the same manner as described above. In the well, an ABTS solution (produced by KPL Corp.) is placed and left standing at room temperature for 15 minutes to one hour to effect a reaction of coloration. The solution is then tested for absorbance at 405 nm by the use of a photometer for 96-well EIA plate.

EXAMPLE 8

Production of Recombinant Vector Carrying DNA Coding for Fused Protein of Peptide Containing DHFR and Part of Antigenic Polypeptide of *Chlamydia pneumoniae* and Production of Transformant Containing the Recombinant Vector A plasmid pBBK10MM was severed with restriction enzymes of BamHI and XhoI and subjected to 1.2% low melting temperature solution agarose gel electrophoresis to excise about 4.6 Kbp of DNA fragment. This fragment was purified.

Separately, a 53-3S λ phage DNA was severed with a restriction enzyme EcoRI to obtain about 1.0 Kbp of DNA fragment similarly in a purified form. This DNA segment was further severed with a restriction enzyme AvaII to obtain about 0.8 Kbp of a DNA segment similarly in a purified form. The amount 100 ng of about 4.6 Kbp of DNA segment, 100 ng of about 0.8 Kbp of DNA segment mentioned above, and 1 ng of each of the synthetic DNA's of SEQ ID Nos: 21 through 24 added thereto were subjected to DNA ligation by the use of the DNA ligation kit (produced by Takara Shuzo Co., Ltd.). The reaction product was placed in an *Escherichia coli* HB101 strain competent cell (produced by Takara Shuzo Co., Ltd.) to produce a transformant.

This transformant was spread on a LB agar culture medium containing 50 mg/L of ampicillin and cultured thereon at 37° C. for 24 hours. The *Escherichia coli* colony consequently obtained was inoculated to 3 ml of the LB culture medium containing 50 mg/L of ampicillin and then shaken cultured overnight at 37° C. The plasmid vector was separated from the culture medium by the alkali lysis method, severed with a restriction enzyme NruI, and analyzed by 0.8% agarose gel electrophoresis to select an *Escherichia coli* possessing a recombinant plasmid vector which had produced DNA segments of 616 bp and 4822 bp. The recombinant plasmid vector thus obtained was designated as pCPN533T. This plasmid vector was a DNA of a length of about 5.4 kbp possessing a base sequence of SEQ ID No: 25. It was capable of expressing a fused protein having a polypeptide containing part of the 53 KDa antigenic polypeptide of *Chlamydia pneumoniae* ligated to the C terminal of DHFR. The base sequence of the DNA coding for this fused protein was shown by SEQ ID No: 18. The amino acid sequence deduced from this base sequence was shown by SEQ ID No: 16.

EXAMPLE 9

Recognition of Fused Protein of Polypeptide Containing DHFR and Part of 53 KDa Antigenic Polypeptide of *Chlamydia pneumoniae*

One platinum loop full of the HB101 strain of *Escherichia coli* retaining plasmid pCPN533T was inoculated to 3 ml of the LB culture medium containing 50 mg/l of ampicillin and shaken cultured overnight at 37° C. The amount 10 μl of the culture medium containing the *Escherichia coli* and 10 μl of loading buffer (a 0.156M tris-hydrochloride buffer containing 0.01% of bromophenol blue, 10% of mercapto ethanol, 20% of glycerol, and 5% of SDS and having pH 6.8) added thereto were heated at 80° C. for five minutes. The resultant reaction solution was subjected to 5–20% polyacrylamide gradient gel electrophoresis. On the anode plate of a semi-dry blotting device, one filter paper wetted with a 0.3M tris aqueous solution containing 10% of methanol and 0.05% sodium dodecyl sulfate, one filter paper wetted with a 25 mM tris aqueous solution containing 10% of methanol and 0.05% of sodium dodecyl sulfate, one filter paper wetted with a 25 mM tris aqueous solution containing 10% of methanol and 0.05% of sodium dodecyl sulfate, one nitrocellulose membrane wetted with a 25 mM tris aqueous solution containing 10% of methanol, 0.05% of sodium dodecyl sulfate, and 40 mM aminocaproic acid, the polyacryl amide gel completely undergone the aforementioned electrophoresis and two filter papers wetted with a 25 mM tris aqueous solution containing 40 mM aminocaproic acid were superposed sequentially in the order mentioned. A cathode plate was set as opposed to the anode plate across the superposed filters and an electric current was passed through the filters at a current density of 2.5 mA/cm$^2$ for one hour to effect transfer of the protein in the polyacrylamide gel to the nitrocellulose membrane. The nitrocellulose membrane was placed in a TBS buffer containing 0.1% of bovine serum albumin and left standing therein at room temperature for not less than one hour to effect blocking. The nitrocellulose membrane was washed twice with the TTBS buffer and then shaken in a monoclonal antibody solution produced by the hybridoma SCP53 (in the 5 to 10 μg/ml TTBS buffer) at 37° C. for one hour. The nitrocellulose membrane was washed three times with the TTBS buffer and then shaken in an aqueous solution of an anti-mouse IgG antibody labelled with peroxidase (in the 50 ng/ml TTBS buffer) at 37° C. for one hour. The nitrocellulose membrane was washed three times with the TTBS buffer and then placed in a coloring ground substance solution (obtained by mixing 100 ml of the TBS buffer with 60 μl of an aqueous 30% hydrogen peroxide solution, and 20 ml of a methanolic solution of 4-chloro-1-naphthol) and left reacting at room temperature for 30 minutes. The nitrocellulose membrane was extracted, washed with purified water, and then air-dried. As a result, colored bands were observed at positions corresponding to sizes of fused protein. This fact indicates that the *Escherichia coli* possessing the plasmid pCPN533T expressed the fusion protein containing 53 KDa antigen capable of reacting with the monoclonal antibody specifically reacting *Chlamydia pneumoniae*.

EXAMPLE 10

Acquisition of DNA Coding for Entire 53 KDa Antigenic Polypeptide of *Chlamydia pneumoniae*

The DNA encoding the whole 53 kDa antigen polypeptide of *Chlamydia pneumoniae* was already acquired in Example 3. However, it was separately obtained the DNA as follows.

A DNA coding for the entire 53 KDa antigenic polypeptide of *Chlamydia pneumoniae* was also obtained by effecting a genome walking by the use of the plasmid pCPN533T and the DNA library of λgt11. When these DNAs were analyzed for base sequence, it was found to possess the 484th through 1947th base sequences of SEQ ID No: 17 and code for the 162nd through 649th amino sequences of SEQ ID No: 15.

EXAMPLE 11

Production of Recombinant Vector Carrying DNA Coding for Fused protein of DHFR and Entire 53 KDa Antigenic Polypeptide of *Chlamydia pneumoniae* and Production of Transformant Containing the Recombinant Vector The recombinant vector containing the DNA encoding the fused protein of DHFR and the whole 53 kDa antigen polypeptide of *Chlamydia pneumoniae* and the transformant containing the recombinant vector can be produced as follows.

A recombinant vector containing a DNA coding for the fused protein of the DHFR and the entire 53 KDa antigenic polypeptide of *Chlamydia pneumoniae* is produced by following the procedure of Example 8 while using a DNA coding for the plasmid PBBK10MM and the entire 53 KDa antigenic polypeptide of *Chlamydia pneumoniae* mentioned above and the transformant containing the recombinant vector was produced. The base sequence of the DNA coding for the fused protein is shown by SEQ ID No: 17 and the amino acid sequence deduced from this base sequence is shown by SEQ ID No: 15.

EXAMPLE 12

Production of anti-*Chlamydia pneumoniae* Antibody by Use of Fused Protein as an Antigen The anti-*Chlamydia pneumoniae* antibody can be produced by using the fused protein of this invention as an antigen as follows.

A hybridoma producing an anti-*Chlamydia pneumoniae* antibody is obtained by following the procedure of Example 6 while using the fused protein mentioned above as an antigen for immunization. This hybridoma is cultured and the anti-*Chlamydia pneumoniae* antibody is produced from the culture supernatant consequently formed.

EXAMPLE 13

Detection and Determination of anti-*Chlamydia pneumoniae* Antibody by Using Fused Protein as Antigen The anti-*Chlamydia pneumoniae* can be detected and measured by using the fused protein of this invention as an antigen as follows.

The polypeptide formed of the amino acid sequence of SEQ ID No: 15 is used as a fused protein. It is fixed on a microtiter plate, made to add a PBS containing bovine serum albumin, and left standing overnight at 4° C. to effect blocking. The PBS containing the bovine serum albumin is removed and the plate is washed twice with the PBS containing 0.02% (w/v) Tween 20. The blood serum from a patient is added to the wells and is left standing at room temperature for two hours. The well is washed three times with the PBS containing 0.02% (w/v) Tween 20 in the same manner as described above. In each of the wells, a peroxidase-labelled mouse anti-human IgG antibody is placed and left standing at room temperature for two hours. The culture solution in the well is washed three times with the PBS containing 0.02% (w/v) Tween 20 in the same manner as described above. In the well, an ABTS solution (produced by KPL Corp.) is placed and left standing at room temperature for 15 minutes to one hour to effect a reaction of coloration. The culture solution is then tested for absorbance at 405 nm by the use of a photometer for 96-well EIA plate.

EXAMPLE 14

Detection of *Chlamydia pneumoniae* Gene by PCR Method

A DNA formed of a base sequence of SEQ ID No: 19 and a DNA formed of a base sequence of SEQ ID No: 20 were chemically synthesized with a DNA synthesizing device produced by Applied Biosystems Corp and were designated respectively as Primer 53F2 and Primer 53R2.

The cells infected with the YK41 strain of *Chlamydia pneumoniae* or the L2 strain of *Chlamydia trachomatis* or the Bugd. 17-SL strain of *Chlamydia psittaci* were recovered by centrifugation. The cells plus 0.1 ml of a 50 mM tris-hydrochloride buffer (pH 8.3) containing 50 mM of KCl, 2.5 mM of $MgCl_2$, 0.1 mg/ml of gelatin, 0.45% of Nonidet P40, 0.45% of Tween 20, and 0.1 mg/ml of proteinase K were kept warmed at 56° C. for one hour and then heated at 95° C. for 10 minutes to inactivate the proteinase K and obtain a sample containing the gene of relevant chlamydia.

One (1)$\mu$l of the sample was combined with 78.5 $\mu$l of purified water, 8 $\mu$l of an aqueous 2.5 mM dNTP solution, 10 $\mu$l of a 100 mM tris-hydrochloride buffer (pH 8.3) containing 500 mM of KCl and 15 mM of $MgCl_2$, 1 $\mu$l each of the aqueous solutions of 30 $\mu$M Primer 53F2 and Primer 53R2 mentioned above, and 0.5 $\mu$l of 5 U/$\mu$l of Taq polymerase. The resultant mixture was superposed by 50 $\mu$l of mineral oil and subjected to 30 cycles of a procedure which consisted of heating at 94° C. for 30 seconds, at 60° C. for 30 seconds, and at 72° C. for 60 seconds, cooling, and warming.

After the reaction was completed, 2 $\mu$l of the reaction solution was subjected to agarose gel electrophoresis, with the gel immersed in 0.5 $\mu$/ml of ethidium bromide to make a band of DNA visible by irradiation of an ultraviolet light.

As a result, the sample obtained from the YK41 strain of *Chlamydia pneumoniae* was found to form a visible band of DNA of a size of 360 bp corresponding to a region interposed between the base sequence of Primer 53F2 and a base sequence complementary to the base sequence of Primer 53R2 in all the base sequences of SEQ ID No: 3. The samples obtained from the other strains were not found to form any visible band of DNA.

INDUSTRIAL APPLICABILITY

The antigenic polypeptide of this invention formed of a polypeptide A containing at least five continuous amino acid sequences in the polypeptides of SEQ ID No: 1 can be utilized as for the examination of an antibody of *Chlamydia pneumoniae*.

The antigenic polypeptide of this invention the polypeptide A of which is a polypeptide arising from the loss of 1 to 250 amino acids from the polypeptides of SEQ ID No: 1 has an amino acid sequence of a small length and, therefore, is enabled to increase the number of antigenic peptides which can be fixed as on a carrier. Thus, it can be utilized for the production of a diagnostic agent of high sensitivity.

The antigenic polypeptide of this invention the polypeptide A of which is a polypeptide resulting from the substitution of 1 to 100 amino acids in the polypeptides of SEQ ID No: 1 by other amino acids is capable of forming a structure only sparingly susceptible of the decomposition by a protease and, therefore, is excellent in stability as an antigen.

The antigenic polypeptide of this invention the polypeptide A of which is a polypeptide having an amino acid or 2 to 1000 amino acid sequences ligated to at least five continuous amino acid sequences in the polypeptides of SEQ ID No: 1 can be fixed as to a carrier by making use of the amino acid or 2 to 1000 amino acid sequences and, therefore, does not easily yield to decline or loss of the antigenecity by fixation.

The antigenic polypeptide of this invention the polypeptide A of which is a polypeptide formed of amino acid sequences of SEQ ID No: 1 possesses the whole of antigenic polypeptides specific to *Chlamydia pneumoniae* and, therefore, is highly suitable for the examination of antigens and for accurate diagnosis of infections involving *Chlamydia pneumoniae*.

The antigenic polypeptide of this invention the polypeptide A of which is a polypeptide formed of amino acid sequences of SEQ ID No: 2 or ID No: 5 possesses an antigenic part specific to *Chlamydia pneumoniae* and, therefore, is highly suitable for the examination of antigens and for accurate diagnosis of infections involving *Chlamydia pneumoniae*.

The DNA of this invention which is a DNA coding for any of the antigenic polypeptides mentioned above or a DNA complementary thereto can be utilized for the production of an antigenic polypeptide suitable for the examination of antigens of *Chlamydia pneumonia*, the diagnosis of infections involving *Chlamydia pneumoniae*, and the like.

The DNA of this invention the base sequence of which is a base sequence of SEQ ID No: 3 codes for the whole of the antigenic polypeptide specific to *Chlamydia pneumoniae* can be utilized for the production of an antigenic polypeptide suitable for the examination of antibodies specific to *Chlamydia pneumoniae*.

The DNA of this invention the base sequence of which is a base sequence of SEQ ID No: 4 or ID No: 7 codes for the antigenic part specific to *Chlamydia pneumoniae* can be utilized for the production of an antigenic polypeptide suitable for the examination of antigens specific to *Chlamydia pneumoniae*.

The recombinant vector of this invention containing any of the DNA's mentioned above can be utilized for the production of an antigenic polypeptide suitable for the examination of an antibody of *Chlamydia pneumoniae* and the diagnosis of infections involving *Chlamydia pneumoniae*.

The recombinant vector of this invention which is a pCPN533a plasmid possessing a base sequence of SEQ ID No: 10 is capable of expressing a polypeptide possessing an antigenic part specific to *Chlamydia pneumoniae* and, therefore, can be utilized for the production of an antigenic polypeptide highly suitable as for the examination of antibodies specific to *Chlamydia pneumoniae*.

The transformant of this invention which contains any of the recombinant vectors mentioned above can be utilized for the production of an antigenic polypeptide suitable as for the examination of antibody specific to *Chlamydia pneumoniae*.

The method of this invention for the production of an anti-*Chlamydia pneumoniae* antibody which is characterized by using any of the antigenic polypeptides mentioned above as an antigen can be utilized for the production of a diagnostic agent for infections involving *Chlamydia pneumoniae*.

The method of this invention for the detection and determination of an anti-*Chlamydia pneumoniae* antibody which is characterized by using any of the antigenic polypeptides mentioned above as an antigen can be utilized for the examination of antibodies of *Chlamydia pneumoniae* and the diagnosis of infections involving *Chlamydia pneumoniae*.

Particularly when an antigenic polypeptide having an amino acid sequence of a small length is utilized, it manifests high sensitivity because it allows an increase in the number of antigenic polypeptides to be fixed as on a carrier.

When an antigenic polypeptide having amino acids inherent therein substituted by other amino acids is utilized for the detection and determination mentioned above, the results of the detection and determination are highly reliable because the antigenic polypeptide is capable of forming a structure only sparingly susceptible to decomposition by a protease and, consequently, excellent in stability.

When an antigenic polypeptide adding other amino acid sequences is utilized for the diagnosis of infections involving *Chlamydia pneumoniae*, it fulfills the role ideally because it enables a polypeptide being used as an antigen to be fixed as on a carrier by making use of amino acids or 2 to 1000 amino acid sequences and only sparingly incurs decline or loss of the antigenicity due to the fixation.

When an antigenic polypeptide formed of amino acid sequences of SEQ ID No: 1 is utilized for the examination of antibodies or the diagnosis of infections involving *Chlamydia pneumoniae*, it fulfills the examination or the diagnosis with perfect accuracy because a polypeptide being used as an antigen possesses the whole antigenic polypeptide specific to *Chlamydia pneumoniae*.

When an antigenic polypeptide formed of amino acid sequences of SEQ ID No: 2 or ID No: 5 is utilized for the examination of antibodies or the diagnosis of infections involving *Chlamydia pneumoniae*, it fulfills the examination or the diagnosis with perfect accuracy because a polypeptide being used as an antigen possesses an antigenic part specific to *Chlamydia pneumoniae*.

The reagent of this invention for the detection and determination of an anti-*Chlamydia pneumoniae* antibody which contains any of the antigenic polypeptides mentioned above as an antigen ideally fits the examination of antibodies of *Chlamydia pneumoniae* and the diagnosis of infections involving *Chlamydia pneumoniae*.

Particularly, when an antigenic polypeptide having an amino acid sequence of a small length is utilized for the reagent, the reagent enjoys high sensitivity because it allows an increase in the number of antigenic polypeptides to be fixed as on a carrier.

When an antigenic polypeptide having amino acids inherent therein substituted by other amino acids is utilized for the detection and determination mentioned above, the results of the examination and determination are highly reliable because the antigenic polypeptide is capable of forming a structure only sparingly susceptible to decomposition by a protease and, as a result, excellent in stability.

Further, when an antigenic polypeptide adding other amino acid sequences is utilized for the diagnosis of infections involving *Chlamydia pneumoniae*, it fulfills the role ideally because it enables a polypeptide being used as an antigen to be fixed as on a carrier by making use of amino acids or 2 to 1000 amino acid sequences and only sparingly incurs decline or loss of the antigenicity due to the fixation.

Then, when an antigenic polypeptide formed of amino acid sequences of SEQ ID No: 1 is utilized for the examination of antibodies or the diagnosis of infections involving *Chlamydia pneumoniae*, it fulfills the examination or the diagnosis with perfect accuracy because a polypeptide being used as an antigen possesses the whole antigenic polypeptide specific to *Chlamydia pneumoniae*.

When an antigenic polypeptide formed of amino acid sequences of SEQ ID No: 2 or ID No: 5 is utilized for the examination of antibodies or the diagnosis of infections involving *Chlamydia pneumoniae*, it fulfills the examination or the diagnosis with perfect accuracy because a polypeptide being used as an antigen possesses an antigenic part specific to *Chlamydia pneumoniae*.

The diagnostic agent of this invention which has any of the antigenic polypeptides mentioned above as an active component ideally fits the diagnosis of infections involving *Chlamydia pneumoniae*.

Particularly, when an antigenic polypeptide having an amino acid sequence of a short length is adopted for the agent, the agent enjoys high sensitivity because it allows an increase in the number of antigenic polypeptides to be fixed as on a carrier.

When an antigenic polypeptide having amino acids inherent therein substituted by other amino acids is utilized for the detection and determination mentioned above, the results of the examination and determination are highly reliable because the antigenic polypeptide is capable of forming a structure only sparingly susceptible to decomposition by a protease and, as a result, excellent in stability.

Further, when an antigenic polypeptide adding other amino acid sequences is utilized for the diagnosis of infections involving *Chlamydia pneumoniae*, it fulfills the role ideally because it enables a polypeptide being used as an antigen to be fixed as on a carrier by making use of amino acids or 2 to 1000 amino acid sequences and only sparingly incurs decline or loss of the antigenicity due to the fixation.

Then, when an antigenic polypeptide formed of amino acid sequences of SEQ ID No: 1 is utilized for the examination of antibodies or the diagnosis of infections involving *Chlamydia pneumoniae*, it fulfills the examination or the diagnosis with perfect accuracy because a polypeptide being used as an antigen possesses the whole antigenic polypeptide specific to *Chlamydia pneumoniae*.

When an antigenic polypeptide formed of amino acid sequences of SEQ ID No: 2 or ID No: 5 is utilized for the examination of antibodies or the diagnosis of infections involving *Chlamydia pneumoniae*, it fulfills the examination or the diagnosis with perfect accuracy because a polypeptide being used as an antigen possesses an antigenic part specific to *Chlamydia pneumoniae*.

The fused protein of this invention which has ligated to a polypeptide of SEQ ID No: 14 either directly or through the medium of an amino acid sequence a polypeptide A containing at least five continuous amino acid sequences in the polypeptides of SEQ ID No: 1 can be utilized as for the examination of antibodies of *Chlamydia pneumoniae*.

The fused protein of this invention the polypeptide A of which is a polypeptide arising from the loss of 1 to 250 amino acids from the polypeptides of SEQ ID No: 1 has an amino acid sequence of a small length and, therefore, is enabled to increase the number of antigenic peptides which can be fixed as on a carrier. Thus, it can be utilized for the production of a diagnostic agent of high sensitivity.

The fused protein of this invention the polypeptide A of which is a polypeptide resulting from the substitution of 1 to 100 amino acids in the polypeptides of SEQ ID No: 1 by other amino acids is capable of forming a structure only sparingly susceptible of the decomposition by a protease and, therefore, is excellent in stability as an antigen.

The fused protein of this invention which is a polypeptide formed of amino acid sequences of SEQ ID No: 15 is highly suitable for the examination of antibodies and the diagnosis of infections involving *Chlamydia pneumoniae* because it possesses the whole of antigenic polypeptides specific to *Chlamydia pneumoniae*.

The fused protein of this invention which is a polypeptide formed of amino acid sequences of SEQ ID No: 16 is highly suitable for the examination of antibodies and the diagnosis of infections involving *Chlamydia pneumoniae* because it possesses an antigenic part specific to *Chlamydia pneumoniae*.

The DNA of th is invention which is a DNA coding for any of the fused proteins mentioned above or a DNA complementary thereto can be utilized for the production of a fused protein suitable for the examination of antibodies of *Chlamtdia pneumoniae*, the diagnosis of infections involving *Chlamydia pneumoniae*, and the like.

The DNA of this invention the base sequences of which are base sequences of SEQ ID No: 17 can be utilized for the production of a fused protein suitable as for the examination of antibodies specific to *Chlamydia pneumoniae* because the fused protein coded for by this DNA possesses the whole of antigenic polypeptides specific to *Chlamydia pneumoniae*.

The DNA of this invention the base sequences of which are base sequences of SEQ ID No: 18 can be utilized for the production of a fused protein suitable as for the examination of antibodies specific to *Chlamydia pneumoniae* because the fused protein coded for by this DNA possesses an antigenic part specific to *Chlamydia pneumoniae*.

The recombinant vector of this invention which carries any of the DNA's mentioned above can be utilized for the production of a fused protein suitable for the examination of antibodies of *Chlamydia pneumoniae* and the diagnosis of infections involving *Chlamydia pneumoniae*.

The recombinant vector of this invention which is a pCPN533T plasmid can be utilized for the production of a fused protein highly suitable as for the examination of antibodies specific to *Chlamydia pneumoniae* because it is capable of expressing a fused protein possessing an antigenic part specific to *Chlamydia pneumoniae*.

The transformant of this invention which contains any of the recombinant vectors mentioned above can be utilized for the production of a fused protein suitable as for the examination of antibodies specific to *Chlamydia pneumoniae*.

The method of this invention for the production of an anti-*Chlamydia pneumoniae* antibody which is characterized by using any of the fused proteins mentioned above as an antigen can be utilized for the production of a diagnostic agent for infections involving *Chlamydia pneumoniae*.

The method of this invention for the detection and determination of an anti-*Chlamydia pneumoniae* antibody which is characterized by using any of the fused proteins mentioned above as an antigen is suitable for the examination of antibodies of *Chlamydia pneumoniae* and the diagnosis of infections involving *Chlamydia pneumoniae*.

Particularly, when a fused protein having an amino acid sequence of a short length is adopted for the method, the method enjoys high sensitivity because this fused protein allows an increase in the number of antigenic polypeptides to be fixed as on a carrier.

When a fused protein having amino acids inherent therein substituted by other amino acids is utilized for the detection and determination mentioned above, the results of the examination and determination are highly reliable because the fused protein is capable of forming a structure only sparingly susceptible to decomposition by a protease and, as a result, excellent in stability.

A fused protein which is formed of amino acid sequences of SEQ ID No: 15 is highly suitable for the examination of antibodies and the diagnosis of infections involving *Chlamydia pneumoniae* because a fused protein being used as an antigen possesses the whole of antigenic polypeptides specific to *Chlamydia pneumoniae*.

A fused protein which is formed of amino acid sequences of SEQ ID No: 16 is highly suitable for the examination of antibodies and the diagnosis of infections involving Chlamydia pneumoniae because a fused protein being used as an antigen possesses an antigenic part specific to Chlamydia pneumoniae.

The reagent of this invention which contains any of the fused proteins mentioned above as an antigen is suitable for the examination of antibodies of Chlamydia pneumoniae and the diagnosis of infections involving Chlamydia pneumoniae.

Particularly, when a fused protein having an amino acid sequence of a small length is utilized for the reagent, the reagent enjoys high sensitivity because it allows an increase in the number of antigenic polypeptides to be fixed as on a carrier.

When a fused protein having amino acids inherent therein substituted by other amino acids is utilized for the detection and determination mentioned above, the results of the examination and determination are highly reliable because the fused protein is capable of forming a structure only sparingly susceptible to decomposition by a protease and, as a result, excellent in stability.

A fused protein which is formed of amino acid sequences of SEQ ID No: 15 is highly suitable for the examination of antibodies and the diagnosis of infections involving Chlamydia pneumoniae because a fused protein being used as an antigen possesses the whole of antigenic polypeptides specific to Chlamydia pneumoniae.

A fused protein which is formed of amino acid sequences of SEQ ID No: 16 is highly suitable for the examination of antibodies and the diagnosis of infections involving Chlamydia pneumoniae because a fused protein being used as an antigen possesses an antigenic part specific to Chlamydia pneumoniae.

The diagnostic medicine of this invention having any of the fused proteins mentioned above as an active component thereof is suitable for the examination of antibodies of Chlamydia pneumoniae and the diagnosis of infections involving Chlamydia pneumoniae.

Particularly, when a fused protein having an amino acid sequence of a small length is utilized for the agent, the agent enjoys high sensitivity because it allows an increase in the number of antigenic polypeptides to be fixed as on a carrier.

When a fused protein having amino acids inherent therein substituted by other amino acids is utilized for the detection and determination mentioned above, the results of the examination and determination are highly reliable because the fused protein is capable of forming a structure only sparingly susceptible to decomposition by a protease and, as a result, excellent in stability.

A fused protein which is formed of amino acid sequences of SEQ ID No: 15 is highly suitable for the examination of antibodies and the diagnosis of infections involving Chlamydia pneumoniae because a fused protein being used as an antigen possesses the whole of antigenic polypeptides specific to Chlamydia pneumoniae.

A fused protein which is formed of amino acid sequences of SEQ ID No: 16 is highly suitable for the examination of antibodies and the diagnosis of infections involving Chlamydia pneumoniae because a fused protein being used as an antigen possesses an antigenic part specific to Chlamydia pneumoniae.

The probe and the primer of this invention are suitable for the detection and determination of a Chlamydia pneumoniae gene and the diagnosis of infections involving Chlamydia pneumoniae.

Particularly, a probe and a primer which possesses base sequences of SEQ ID No: 19 or ID No: 20 can be utilized for accurate diagnosis of infections involving Chlamydia pneumoniae because they possess base sequences specific to Chlamydia pneumoniae.

The method of this invention for the detection and determination of a Chlamydia pneumoniae gene by the use of any of the probes or primers mentioned above is suitable for the diagnosis of infections involving Chlamydia pneumoniae.

The reagent of this invention for the detection and determination of a Chlamydia pneumoniae which contains any of the probes or the primers mentioned above is ideally suitable for the diagnosis of infections involving Chlamydia pneumoniae.

The diagnostic agent of this invention which has any of the probes or the primers mentioned above as an active component is ideally suitable for the diagnosis of infections involving Chlamydia pneumoniae.

What is claimed is:

1. A method for detecting anti-*Chlamydia pneumoniae* antibody in a biological sample, comprising the steps of:
   incubating said biological sample with a *Chlamydia pneumoniae* antigenic polypeptide comprising a polypeptide A which comprises a sequence of at least 5 consecutive amino acids in the polypeptide of SEQ ID NO: 1 and is capable of binding to said antibody that recognizes the polypeptide consisting of SEQ ID NO:1, and detecting an antigen-antibody complex as formed with said biological sample and said antigen.

2. The method of claim 1, wherein at least one amino acid and at most 250 amino acids of SEQ ID NO: 1 is/are deleted from polypeptide A, and wherein a sequence of at least 5 consecutive amino acids in the polypeptide of SEQ ID NO: 1 remains after the deletion.

3. The method of claim 1, wherein (1) at least one amino acid and at most 100 amino acids of SEQ ID NO: 1 is/are replaced in polypeptide A, and wherein a sequence of at least 5 consecutive amino acids in the polypeptide of SEQ ID NO: 1 remains after the replacement, or (2) at least one amino acid of SEQ ID NO: 1 and at most 100 amino acids is/are added or deleted in polypeptide A, and wherein a sequence of at least 5 consecutive amino acids in the polypeptide of SEQ ID NO: 1 remains after the addition and deletion.

4. A method according to claim 1, wherein said antigenic polypeptide is a chimera comprising said polypeptide A fused to a different polypeptide sequence.

5. A method according to claim 1, further comprising a step of measuring an amount of said antigen-antibody complex.

6. A method according to claim 1, wherein said antigen-antibody complex is detected by ELISA.

7. A method according to claim 1, wherein said antigen-antibody complex is detected by Western blot.

8. A method according to claim 1, wherein said antigen-antibody complex is detected by flow cytometry.

9. A method for detecting anti-*Chlamydia pneumoniae antibody in a biological sample, comprising the steps of:* incubating said biological sample with a *Chlamydia pneumoniae* antigenic polypeptide comprising the amino acid sequence of SEQ ID NO: 1, and detecting an antigen-antibody complex as formed with said biological sample and said antigen.

10. A method for detecting anti-*Chlamydia pneumoniae* antibody in a biological sample, comprising the steps of:

incubating said biological sample with a *Chlamydia pneumoniae* antigenic polypeptide comprising the amino acid sequence of SEQ ID NO: 2, and detecting an antigen-antibody complex as formed with said biological sample and said antigen.

11. A method for detecting anti-*Chlamydia pneumoniae* antibody in a biological sample, comprising the steps of:

incubating said biological sample with a *Chlamydia pneumoniae* antigenic polypeptide comprising the amino acid sequence of SEQ ID NO: 5, and detecting an antigen-antibody complex as formed with said biological sample and said antigen.

12. A method according to claim 9, 10, or 11 wherein said antigen-antibody complex is detected by a method which is selected from the group consisting of ELISA, Western Blot, and Flow Cytometry.

13. The method according to 1, wherein said polypeptide A comprises a sequence of at least 20 consecutive amino acids in the polypeptide of SEQ ID NO: 1.

14. The method according to 1, wherein said polypeptide A comprises a sequence of at least 100 consecutive amino acids in the polypeptide of SEQ ID NO: 1.

15. The method according to claim 1, wherein said polypeptide A comprises a sequence of at least 250 consecutive amino acids in the polypeptide of SEQ ID NO: 1.

16. A method for detecting anti-*Chlamydia pneumoniae* antibody in a biological sample, comprising the steps of:

incubating said biological sample with an antigen comprising a fused protein of a *Chlamydia pneumoniae* antigenic polypeptide B with dihydrofolate reductase, wherein said *Chlamydia pneumoniae* antigenic polypeptide is capable of binding to said antibody that recognizes the polypeptide consisting of SEQ ID NO:1, which comprises at least 5 consecutive amino acids in polypeptide of SEQ ID NO: 1 and is bound to the polypeptide of SEQ ID NO: 14 either directly or via an intervening amino acid or amino acid sequence, and detecting an antigen-antibody complex as formed with said biological sample and said antigen.

17. The method of claim 16, wherein at least one amino acid and at most 250 amino acids of SEQ ID NO: 1 is/are deleted from polypeptide B, and wherein a sequence of at least 5 consecutive amino acids in the polypetide of SEQ ID NO: 1 remains after the deletion.

18. The method of claim 16, wherein (1) at least one amino acid and at most 100 amino acids of SEQ ID NO: 1 is/are replaced in polypeptide B, and wherein a sequence of at least 5 consective amino acids in the polypeptide of SEQ ID NO: 1 remains after the replacement, or (2) at least one amino acid of SEQ ID NO: 1 and at most 100 amino acids is/are added or deleted in polypeptide B, and wherein a sequence of at least 5 consecutive amino acids in the polypeptide of SEQ ID NO: 1 remains after the addition or deletion.

19. A method for detecting anti-*Chlamydia pneumoniae* antibody in a biological sample, comprising the steps of:

incubating said biological sample with an antigen comprising a fused protein of a *Chlamydia pneumoniae* antigenic polypeptide with dihydrofolate reductase, wherein said *Chlamydia pneumoniae* antigenic polypeptide comprises the amino acid sequence of SEQ ID NO: 15 and is bound to the polypeptide of SEQ ID NO: 14 either directly or via an intervening amino acid or amino acid sequence, and detecting an antigen-antibody complex as formed with said biological sample and said antigen.

20. A method for detecting anti-*Chlamydia pneumoniae* antibody in a biological sample, comprising the steps of:

incubating said biological sample with an antigen comprising a fused protein of a *Chlamydia pneumoniae* antigenic polypeptide with dihydrofolate reductase, wherein said *Chlamydia pneumoniae* antigenic polypeptide comprises the amino acid sequence of SEQ ID NO: 16 and is bound to the polypeptide of SEQ ID NO: 14 either directly or via an intervening amino acid or amino acid sequence, and detecting an antigen-antibody complex as formed with said biological sample and said antigen.

21. The method according to 16, wherein said polypeptide B comprises a sequence of at least 20 consecutive amino acids in the polypeptide of SEQ ID NO: 1.

22. The method according to 16, wherein said polypeptide B comprises a sequence of at least 100 consecutive amino acids in the polypeptide of SEQ ID NO: 1.

23. The method according to 16, wherein said polypeptide B comprises a sequence of at least 250 consecutive amino acids in the polypeptide of SEQ ID NO: 1.

24. The method according to claim 3 or claim 18, wherein said polypeptide A comprises a polypeptide sequence of SEQ ID NO: 1 in which at least five amino acid and at most 100 amino acids are replaced with other amino acid.

* * * * *

UNITED STATES PATENT AND TRADEMARK OFFICE
CERTIFICATE OF CORRECTION

PATENT NO. : 6,489,122 B1  Page 1 of 1
DATED : December 3, 2002
INVENTOR(S) : Izutsu et al.

It is certified that error appears in the above-identified patent and that said Letters Patent is hereby corrected as shown below:

Title page,
Item [62], Related U.S. Application Data, should read -- [62] Division of application No. 08/809,326, filed as application No. PCT/JP95/01896 on Sep. 19, 1997, now Pat. No. 6,165,478. --.

Signed and Sealed this

Third Day of February, 2004

JON W. DUDAS
*Acting Director of the United States Patent and Trademark Office*

SEQUENCE LISTING

```
<160> NUMBER OF SEQ ID NOS: 33

<210> SEQ ID NO 1
<211> LENGTH: 488
<212> TYPE: PRT
<213> ORGANISM: Chlamydophila pneumoniae

<400> SEQUENCE: 1

Met Ser Ile Ser Ser Ser Ser Gly Pro Asp Asn Gln Lys Asn Ile Met
1               5                   10                  15

Ser Gln Val Leu Thr Ser Thr Pro Gln Gly Val Pro Gln Gln Asp Lys
            20                  25                  30

Leu Ser Gly Asn Glu Thr Lys Gln Ile Gln Gln Thr Arg Gln Gly Lys
        35                  40                  45

Asn Thr Glu Met Glu Ser Asp Ala Thr Ile Ala Gly Ala Ser Gly Lys
    50                  55                  60

Asp Lys Thr Ser Ser Thr Thr Lys Thr Glu Thr Ala Pro Gln Gln Gly
```

```
              65                  70                  75                  80
Val Ala Ala Gly Lys Glu Ser Ser Glu Ser Gln Lys Ala Gly Ala Asp
                    85                  90                  95

Thr Gly Val Ser Gly Ala Ala Thr Thr Ala Ser Asn Thr Ala Thr
                100                 105                 110

Lys Ile Ala Met Gln Thr Ser Ile Glu Glu Ala Ser Lys Ser Met Glu
            115                 120                 125

Ser Thr Leu Glu Ser Leu Gln Ser Leu Ser Ala Gln Met Lys Glu
        130                 135                 140

Val Glu Ala Val Val Ala Ala Leu Ser Gly Lys Ser Ser Gly Ser
145                 150                 155                 160

Ala Lys Leu Glu Thr Pro Glu Leu Pro Lys Pro Gly Val Thr Pro Arg
                165                 170                 175

Ser Glu Val Ile Glu Ile Gly Leu Ala Leu Ala Lys Ala Ile Gln Thr
                180                 185                 190

Leu Gly Glu Ala Thr Lys Ser Ala Leu Ser Asn Tyr Ala Ser Thr Gln
        195                 200                 205

Ala Gln Ala Asp Gln Thr Asn Lys Leu Gly Leu Glu Lys Gln Ala Ile
        210                 215                 220

Lys Ile Asp Lys Glu Arg Glu Glu Tyr Gln Glu Met Lys Ala Ala Glu
225                 230                 235                 240

Gln Lys Ser Lys Asp Leu Glu Gly Thr Met Asp Thr Val Asn Thr Val
                245                 250                 255

Met Ile Ala Val Ser Val Ala Ile Thr Val Ile Ser Ile Val Ala Ala
            260                 265                 270

Ile Phe Thr Cys Gly Ala Gly Leu Ala Gly Leu Ala Ala Gly Ala Ala
        275                 280                 285

Val Gly Ala Ala Ala Gly Gly Ala Gly Ala Ala Ala Thr
290                 295                 300

Thr Val Ala Thr Gln Ile Thr Val Gln Ala Val Val Gln Ala Val Lys
305                 310                 315                 320

Gln Ala Val Ile Thr Ala Val Arg Gln Ala Ile Thr Ala Ala Ile Lys
                325                 330                 335

Ala Ala Val Lys Ser Gly Ile Lys Ala Phe Ile Lys Thr Leu Val Lys
            340                 345                 350

Ala Ile Ala Lys Ala Ile Ser Lys Gly Ile Ser Lys Val Phe Ala Lys
        355                 360                 365

Gly Thr Gln Met Ile Ala Lys Asn Phe Pro Lys Leu Ser Lys Val Ile
    370                 375                 380

Ser Ser Leu Thr Ser Lys Trp Val Thr Val Gly Val Gly Val Val
385                 390                 395                 400

Ala Ala Pro Ala Leu Gly Lys Gly Ile Met Gln Met Gln Leu Ser Glu
                405                 410                 415

Met Gln Gln Asn Val Ala Gln Phe Gln Lys Glu Val Gly Lys Leu Gln
            420                 425                 430

Ala Ala Ala Asp Met Ile Ser Met Phe Thr Gln Phe Trp Gln Gln Ala
        435                 440                 445

Ser Lys Ile Ala Ser Lys Gln Thr Gly Glu Ser Asn Glu Met Thr Gln
        450                 455                 460

Lys Ala Thr Lys Leu Gly Ala Gln Ile Leu Lys Ala Tyr Ala Ala Ile
465                 470                 475                 480

Ser Gly Ala Ile Ala Gly Ala Ala
                485
```

-continued

<210> SEQ ID NO 2
<211> LENGTH: 271
<212> TYPE: PRT
<213> ORGANISM: Artificial Sequence
<220> FEATURE:
<223> OTHER INFORMATION: fusion peptide

<400> SEQUENCE: 2

```
Met Ser Ile Ser Ser Ser Ser Gly Pro Asp Asn Gln Lys Asn Ile Met
1               5                   10                  15

Ser Gln Val Leu Thr Ser Thr Pro Gln Gly Val Pro Gln Gln Asp Lys
            20                  25                  30

Leu Ser Gly Asn Glu Thr Lys Gln Ile Gln Gln Thr Arg Gln Gly Lys
        35                  40                  45

Asn Thr Glu Met Glu Ser Asp Ala Thr Ile Ala Gly Ala Ser Gly Lys
    50                  55                  60

Asp Lys Thr Ser Ser Thr Thr Lys Thr Glu Thr Ala Pro Gln Gln Gly
65                  70                  75                  80

Val Ala Ala Gly Lys Glu Ser Ser Glu Ser Gln Lys Ala Gly Ala Asp
                85                  90                  95

Thr Gly Val Ser Gly Ala Ala Ala Thr Thr Ala Ser Asn Thr Ala Thr
            100                 105                 110

Lys Ile Ala Met Gln Thr Ser Ile Glu Glu Ala Ser Lys Ser Met Glu
        115                 120                 125

Ser Thr Leu Glu Ser Leu Gln Ser Leu Ser Ala Ala Gln Met Lys Glu
    130                 135                 140

Val Glu Ala Val Val Val Ala Ala Leu Ser Gly Lys Ser Ser Gly Ser
145                 150                 155                 160

Ala Lys Leu Glu Thr Pro Glu Leu Pro Lys Pro Gly Val Thr Pro Arg
                165                 170                 175

Ser Glu Val Ile Glu Ile Gly Leu Ala Leu Ala Lys Ala Ile Gln Thr
            180                 185                 190

Leu Gly Glu Ala Thr Lys Ser Ala Leu Ser Asn Tyr Ala Ser Thr Gln
        195                 200                 205

Ala Gln Ala Asp Gln Thr Asn Lys Leu Gly Leu Glu Lys Gln Ala Ile
    210                 215                 220

Lys Ile Asp Lys Glu Arg Glu Glu Tyr Gln Glu Met Lys Ala Ala Glu
225                 230                 235                 240

Gln Lys Ser Lys Asp Leu Glu Gly Thr Met Asp Thr Val Asn Thr Val
                245                 250                 255

Met Ile Ala Lys Gly Phe Glu Leu Pro Trp Gly Pro Leu Ile Asn
            260                 265                 270
```

<210> SEQ ID NO 3
<211> LENGTH: 1464
<212> TYPE: DNA
<213> ORGANISM: Artificial Sequence
<220> FEATURE:
<223> OTHER INFORMATION: Synthetic DNA derived from Chlamydophila pneumoniae
<220> FEATURE:
<221> NAME/KEY: CDS
<222> LOCATION: (1)..(1464)
<223> OTHER INFORMATION:

<400> SEQUENCE: 3

```
atg tct att tca tct tct tca gga cct gac aat caa aaa aat atc atg       48
Met Ser Ile Ser Ser Ser Ser Gly Pro Asp Asn Gln Lys Asn Ile Met
```

```
                                               -continued
1              5              10             15 tct caa gtt ctg aca tcg aca ccc cag ggc gtg ccc caa caa gat aag    96
Ser Gln Val Leu Thr Ser Thr Pro Gln Gly Val Pro Gln Gln Asp Lys
                20              25              30 ctg tct ggc aac gaa acg aag caa ata cag caa aca cgt cag ggt aaa   144
Leu Ser Gly Asn Glu Thr Lys Gln Ile Gln Gln Thr Arg Gln Gly Lys
        35              40              45 aac act gag atg gaa agc gat gcc act att gct ggt gct tct gga aaa   192
Asn Thr Glu Met Glu Ser Asp Ala Thr Ile Ala Gly Ala Ser Gly Lys
    50              55              60 gac aaa act tcc tcg act aca aaa aca gaa aca gct cca caa cag gga   240
Asp Lys Thr Ser Ser Thr Thr Lys Thr Glu Thr Ala Pro Gln Gln Gly
65              70              75              80 gtt gct gct ggg aaa gaa tcc tca gaa agt caa aag gca ggt gct gat   288
Val Ala Ala Gly Lys Glu Ser Ser Glu Ser Gln Lys Ala Gly Ala Asp
                85              90              95 act gga gta tca gga gcg gct gct act aca gca tca aat act gca aca   336
Thr Gly Val Ser Gly Ala Ala Ala Thr Thr Ala Ser Asn Thr Ala Thr
        100             105             110 aaa att gct atg cag acc tct att gaa gag gcg agc aaa agt atg gag   384
Lys Ile Ala Met Gln Thr Ser Ile Glu Glu Ala Ser Lys Ser Met Glu
    115             120             125 tct acc tta gag tca ctt caa agc ctc agt gcc gcg caa atg aaa gaa   432
Ser Thr Leu Glu Ser Leu Gln Ser Leu Ser Ala Ala Gln Met Lys Glu
130             135             140 gtc gaa gcg gtt gtt gtt gct gcc ctc tca ggg aaa agt tcg ggt tcc   480
Val Glu Ala Val Val Val Ala Ala Leu Ser Gly Lys Ser Ser Gly Ser
145             150             155             160 gca aaa ttg gaa aca cct gag ctc ccc aag ccc ggg gtg aca cca aga   528
Ala Lys Leu Glu Thr Pro Glu Leu Pro Lys Pro Gly Val Thr Pro Arg
                165             170             175 tca gag gtt atc gaa atc gga ctc gcg ctt gct aaa gca att cag aca   576
Ser Glu Val Ile Glu Ile Gly Leu Ala Leu Ala Lys Ala Ile Gln Thr
        180             185             190 ttg gga gaa gcc aca aaa tct gcc tta tct aac tat gca agt aca caa   624
Leu Gly Glu Ala Thr Lys Ser Ala Leu Ser Asn Tyr Ala Ser Thr Gln
    195             200             205 gca caa gca gac caa aca aat aaa cta ggt cta gaa aag caa gcg ata   672
Ala Gln Ala Asp Gln Thr Asn Lys Leu Gly Leu Glu Lys Gln Ala Ile
210             215             220 aaa atc gat aaa gaa cga gaa gaa tac caa gag atg aag gct gcc gaa   720
Lys Ile Asp Lys Glu Arg Glu Glu Tyr Gln Glu Met Lys Ala Ala Glu
225             230             235             240 cag aag tct aaa gat ctc gaa gga aca atg gat act gtc aat act gtg   768
Gln Lys Ser Lys Asp Leu Glu Gly Thr Met Asp Thr Val Asn Thr Val
                245             250             255 atg atc gcg gtt tct gtt gcc att aca gtt att tct att gtt gct gct   816
Met Ile Ala Val Ser Val Ala Ile Thr Val Ile Ser Ile Val Ala Ala
        260             265             270 att ttt aca tgc gga gct gga ctc gct gga ctc gct gcg gga gct gct   864
Ile Phe Thr Cys Gly Ala Gly Leu Ala Gly Leu Ala Ala Gly Ala Ala
    275             280             285 gta ggt gca gcg gca gct gga ggt gca gca gga gct gct gcc gca acc   912
Val Gly Ala Ala Ala Ala Gly Gly Ala Ala Gly Ala Ala Ala Ala Thr
290             295             300 acg gta gca aca caa att aca gtt caa gct gtt gtc caa gcg gtg aaa   960
Thr Val Ala Thr Gln Ile Thr Val Gln Ala Val Val Gln Ala Val Lys
                305             310             315             320 caa gct gtt atc aca gct gtc aga caa gcg atc acc gcg gct ata aaa  1008
```

```
Gln Ala Val Ile Thr Ala Val Arg Gln Ala Ile Thr Ala Ala Ile Lys
            325                 330                 335 gcg gct gtc aaa tct gga ata aaa gca ttt atc aaa act tta gtc aaa      1056
Ala Ala Val Lys Ser Gly Ile Lys Ala Phe Ile Lys Thr Leu Val Lys
            340                 345                 350 gcg att gcc aaa gcc att tct aaa gga atc tct aag gtt ttc gct aag      1104
Ala Ile Ala Lys Ala Ile Ser Lys Gly Ile Ser Lys Val Phe Ala Lys
            355                 360                 365 gga act caa atg att gcg aag aac ttc ccc aag ctc tcg aaa gtc atc      1152
Gly Thr Gln Met Ile Ala Lys Asn Phe Pro Lys Leu Ser Lys Val Ile
        370                 375                 380 tcg tct ctt acc agt aaa tgg gtc acg gtt ggg gtt ggg gtt gta gtt      1200
Ser Ser Leu Thr Ser Lys Trp Val Thr Val Gly Val Gly Val Val Val
385                 390                 395                 400 gcg gcg cct gct ctc ggt aaa ggg att atg caa atg cag ctc tcg gag      1248
Ala Ala Pro Ala Leu Gly Lys Gly Ile Met Gln Met Gln Leu Ser Glu
                405                 410                 415 atg caa caa aac gtc gct caa ttt cag aaa gaa gtc gga aaa ctg cag      1296
Met Gln Gln Asn Val Ala Gln Phe Gln Lys Glu Val Gly Lys Leu Gln
            420                 425                 430 gct gcg gct gat atg att tct atg ttc act caa ttt tgg caa cag gca      1344
Ala Ala Ala Asp Met Ile Ser Met Phe Thr Gln Phe Trp Gln Gln Ala
        435                 440                 445 agt aaa att gcc tca aaa caa aca ggc gag tct aat gaa atg act caa      1392
Ser Lys Ile Ala Ser Lys Gln Thr Gly Glu Ser Asn Glu Met Thr Gln
450                 455                 460 aaa gct acc aag ctg ggc gct caa atc ctt aaa gcg tat gcc gca atc      1440
Lys Ala Thr Lys Leu Gly Ala Gln Ile Leu Lys Ala Tyr Ala Ala Ile
465                 470                 475                 480 agc gga gcc atc gct ggc gca gca                                      1464
Ser Gly Ala Ile Ala Gly Ala Ala
                485

<210> SEQ ID NO 4
<211> LENGTH: 813
<212> TYPE: DNA
<213> ORGANISM: Artificial Sequence
<220> FEATURE:
<223> OTHER INFORMATION: fusion peptide
<220> FEATURE:
<221> NAME/KEY: CDS
<222> LOCATION: (1)..(813)
<223> OTHER INFORMATION:

<400> SEQUENCE: 4 atg tct att tca tct tct tca gga cct gac aat caa aaa aat atc atg       48
Met Ser Ile Ser Ser Ser Ser Gly Pro Asp Asn Gln Lys Asn Ile Met
1               5                   10                  15 tct caa gtt ctg aca tcg aca ccc cag ggc gtg ccc caa caa gat aag       96
Ser Gln Val Leu Thr Ser Thr Pro Gln Gly Val Pro Gln Gln Asp Lys
            20                  25                  30 ctg tct ggc aac gaa acg aag caa ata cag caa aca cgt cag ggt aaa      144
Leu Ser Gly Asn Glu Thr Lys Gln Ile Gln Gln Thr Arg Gln Gly Lys
        35                  40                  45 aac act gag atg gaa agc gat gcc act att gct ggt gct tct gga aaa      192
Asn Thr Glu Met Glu Ser Asp Ala Thr Ile Ala Gly Ala Ser Gly Lys
    50                  55                  60 gac aaa act tcc tcg act aca aaa aca gaa aca gct cca caa cag gga      240
Asp Lys Thr Ser Ser Thr Thr Lys Thr Glu Thr Ala Pro Gln Gln Gly
65                  70                  75                  80 gtt gct gct ggg aaa gaa tcc tca gaa agt caa aag gca ggt gct gat      288
Val Ala Ala Gly Lys Glu Ser Ser Glu Ser Gln Lys Ala Gly Ala Asp
```

-continued

| | | |
|---|---|---|
| act gga gta tca gga gcg gct gct act aca gca tca aat act gca aca<br>Thr Gly Val Ser Gly Ala Ala Ala Thr Thr Ala Ser Asn Thr Ala Thr<br>          100                    105                 110 | | 336 |
| aaa att gct atg cag acc tct att gaa gag gcg agc aaa agt atg gag<br>Lys Ile Ala Met Gln Thr Ser Ile Glu Glu Ala Ser Lys Ser Met Glu<br>       115                   120               125 | | 384 |
| tct acc tta gag tca ctt caa agc ctc agt gcc gcg caa atg aaa gaa<br>Ser Thr Leu Glu Ser Leu Gln Ser Leu Ser Ala Ala Gln Met Lys Glu<br>130                   135               140 | | 432 |
| gtc gaa gcg gtt gtt gtt gct gcc ctc tca ggg aaa agt tcg ggt tcc<br>Val Glu Ala Val Val Val Ala Ala Leu Ser Gly Lys Ser Ser Gly Ser<br>145                   150               155               160 | | 480 |
| gca aaa ttg gaa aca cct gag ctc ccc aag ccc ggg gtg aca cca aga<br>Ala Lys Leu Glu Thr Pro Glu Leu Pro Lys Pro Gly Val Thr Pro Arg<br>                 165               170               175 | | 528 |
| tca gag gtt atc gaa atc gga ctc gcg ctt gct aaa gca att cag aca<br>Ser Glu Val Ile Glu Ile Gly Leu Ala Leu Ala Lys Ala Ile Gln Thr<br>             180               185               190 | | 576 |
| ttg gga gaa gcc aca aaa tct gcc tta tct aac tat gca agt aca caa<br>Leu Gly Glu Ala Thr Lys Ser Ala Leu Ser Asn Tyr Ala Ser Thr Gln<br>       195                   200               205 | | 624 |
| gca caa gca gac caa aca aat aaa cta ggt cta gaa aag caa gcg ata<br>Ala Gln Ala Asp Gln Thr Asn Lys Leu Gly Leu Glu Lys Gln Ala Ile<br>210                   215               220 | | 672 |
| aaa atc gat aaa gaa cga gaa gaa tac caa gag atg aag gct gcc gaa<br>Lys Ile Asp Lys Glu Arg Glu Glu Tyr Gln Glu Met Lys Ala Ala Glu<br>225                   230               235               240 | | 720 |
| cag aag tct aaa gat ctc gaa gga aca atg gat act gtc aat act gtg<br>Gln Lys Ser Lys Asp Leu Glu Gly Thr Met Asp Thr Val Asn Thr Val<br>                 245               250               255 | | 768 |
| atg atc gcg aag ggg ttc gaa ttg cca tgg ggg ccc tta att aat<br>Met Ile Ala Lys Gly Phe Glu Leu Pro Trp Gly Pro Leu Ile Asn<br>       260                   265               270 | | 813 |

<210> SEQ ID NO 5
<211> LENGTH: 259
<212> TYPE: PRT
<213> ORGANISM: Chlamydophila pneumoniae

<400> SEQUENCE: 5

Met Ser Ile Ser Ser Ser Gly Pro Asp Asn Gln Lys Asn Ile Met
1               5                   10                  15

Ser Gln Val Leu Thr Ser Thr Pro Gln Gly Val Pro Gln Gln Asp Lys
                20                  25                  30

Leu Ser Gly Asn Glu Thr Lys Gln Ile Gln Gln Thr Arg Gln Gly Lys
            35                  40                  45

Asn Thr Glu Met Glu Ser Asp Ala Thr Ile Ala Gly Ala Ser Gly Lys
        50                  55                  60

Asp Lys Thr Ser Ser Thr Thr Lys Thr Glu Thr Ala Pro Gln Gln Gly
65                  70                  75                  80

Val Ala Ala Gly Lys Glu Ser Glu Ser Gln Lys Ala Gly Ala Asp
                85                  90                  95

Thr Gly Val Ser Gly Ala Ala Ala Thr Thr Ala Ser Asn Thr Ala Thr
                100                 105                 110

Lys Ile Ala Met Gln Thr Ser Ile Glu Glu Ala Ser Lys Ser Met Glu
            115                 120                 125

Ser Thr Leu Glu Ser Leu Gln Ser Leu Ser Ala Ala Gln Met Lys Glu

```
                130             135             140
Val Glu Ala Val Val Ala Ala Leu Ser Gly Lys Ser Ser Gly Ser
145                 150                 155                 160

Ala Lys Leu Glu Thr Pro Glu Leu Pro Lys Pro Gly Val Thr Pro Arg
                165                 170                 175

Ser Glu Val Ile Glu Ile Gly Leu Ala Leu Ala Lys Ala Ile Gln Thr
                180                 185                 190

Leu Gly Glu Ala Thr Lys Ser Ala Leu Ser Asn Tyr Ala Ser Thr Gln
            195                 200                 205

Ala Gln Ala Asp Gln Thr Asn Lys Leu Gly Leu Glu Lys Gln Ala Ile
            210                 215                 220

Lys Ile Asp Lys Glu Arg Glu Glu Tyr Gln Glu Met Lys Ala Ala Glu
225                 230                 235                 240

Gln Lys Ser Lys Asp Leu Glu Gly Thr Met Asp Thr Val Asn Thr Val
                245                 250                 255

Met Ile Ala

<210> SEQ ID NO 6
<211> LENGTH: 571
<212> TYPE: PRT
<213> ORGANISM: Chlamydophila pneumoniae

<400> SEQUENCE: 6

Met Pro Lys Gln Ala Glu Tyr Thr Trp Gly Ser Lys Lys Ile Leu Asp
1               5                   10                  15

Asn Ile Glu Cys Leu Thr Glu Asp Val Ala Glu Phe Lys Asp Leu Leu
                20                  25                  30

Tyr Thr Ala His Arg Ile Thr Ser Glu Glu Ser Asp Asn Glu
            35                  40                  45

Ile Gln Pro Gly Ala Ile Leu Lys Gly Thr Val Val Asp Ile Asn Lys
        50                  55                  60

Asp Phe Val Val Asp Val Gly Leu Lys Ser Glu Gly Val Ile Pro
65                  70                  75                  80

Met Ser Glu Phe Ile Asp Ser Ser Glu Gly Leu Val Leu Gly Ala Glu
                85                  90                  95

Val Glu Val Tyr Leu Asp Gln Ala Glu Asp Glu Gly Lys Val Val
                100                 105                 110

Leu Ser Arg Glu Lys Ala Thr Arg Gln Arg Gln Trp Glu Tyr Ile Leu
            115                 120                 125

Ala His Cys Glu Glu Gly Ser Ile Val Lys Gly Gln Ile Thr Arg Lys
        130                 135                 140

Val Lys Gly Gly Leu Ile Val Asp Ile Gly Met Glu Ala Phe Leu Pro
145                 150                 155                 160

Gly Ser Gln Ile Asp Asn Lys Lys Ile Lys Asn Leu Asp Asp Tyr Val
                165                 170                 175

Gly Lys Val Cys Glu Phe Lys Ile Leu Lys Ile Asn Val Glu Arg Arg
                180                 185                 190

Asn Ile Val Val Ser Arg Arg Glu Leu Leu Glu Ala Glu Arg Ile Ser
            195                 200                 205

Lys Lys Ala Glu Leu Ile Glu Gln Ile Ser Ile Gly Glu Tyr Arg Lys
        210                 215                 220

Gly Val Val Lys Asn Ile Thr Asp Phe Gly Val Phe Leu Asp Leu Asp
225                 230                 235                 240

Gly Ile Asp Gly Leu Leu His Ile Thr Asp Met Thr Trp Lys Arg Ile
```

```
                245                 250                 255
Arg His Pro Ser Glu Met Val Glu Leu Asn Gln Glu Leu Glu Val Ile
                260                 265                 270

Ile Leu Ser Val Asp Lys Glu Lys Gly Arg Val Ala Leu Gly Leu Lys
            275                 280                 285

Gln Lys Glu His Asn Pro Trp Glu Asp Ile Glu Lys Lys Tyr Pro Pro
        290                 295                 300

Gly Lys Arg Val Leu Gly Lys Ile Val Lys Leu Leu Pro Tyr Gly Ala
305                 310                 315                 320

Phe Ile Glu Ile Glu Glu Gly Ile Glu Gly Leu Ile His Ile Ser Glu
                325                 330                 335

Met Ser Trp Val Lys Asn Ile Val Asp Pro Ser Glu Val Val Asn Lys
            340                 345                 350

Gly Asp Glu Val Glu Ala Ile Val Leu Ser Ile Gln Lys Asp Glu Gly
        355                 360                 365

Lys Ile Ser Leu Gly Leu Lys Gln Thr Glu Arg Asn Pro Trp Asp Asn
    370                 375                 380

Ile Glu Glu Lys Tyr Pro Ile Gly Leu His Val Asn Ala Glu Ile Lys
385                 390                 395                 400

Asn Leu Thr Asn Tyr Gly Ala Phe Val Glu Leu Glu Pro Gly Ile Glu
                405                 410                 415

Gly Leu Ile His Ile Ser Asp Met Ser Trp Ile Lys Lys Val Ser His
            420                 425                 430

Pro Ser Glu Leu Phe Lys Lys Gly Asn Ser Val Glu Ala Val Ile Leu
        435                 440                 445

Ser Val Asp Lys Glu Ser Lys Lys Ile Thr Leu Gly Val Lys Gln Leu
    450                 455                 460

Ser Ser Asn Pro Trp Asn Glu Ile Glu Ala Met Phe Pro Ala Gly Thr
465                 470                 475                 480

Val Ile Ser Gly Val Val Thr Lys Ile Thr Ala Phe Gly Ala Phe Val
                485                 490                 495

Glu Leu Gln Asn Gly Ile Glu Gly Leu Ile His Val Ser Glu Leu Ser
            500                 505                 510

Asp Lys Pro Phe Ala Lys Ile Glu Asp Ile Ile Ser Ile Gly Glu Asn
        515                 520                 525

Val Ser Ala Lys Val Ile Lys Leu Asp Pro Asp His Lys Lys Val Ser
    530                 535                 540

Leu Ser Val Lys Glu Tyr Leu Ala Asp Asn Ala Tyr Asp Gln Asp Ser
545                 550                 555                 560

Arg Thr Glu Leu Asp Phe Lys Asp Ser Gln Gly
                565                 570
```

<210> SEQ ID NO 7
<211> LENGTH: 777
<212> TYPE: DNA
<213> ORGANISM: Chlamydophila pneumoniae

<400> SEQUENCE: 7

```
atgtctattt catcttcttc aggacctgac aatcaaaaaa atatcatgtc tcaagttctg      60
acatcgacac cccagggcgt gccccaacaa gataagctgt ctggcaacga aacgaagcaa     120
atacagcaaa cacgtcaggg taaaaacact gagatggaaa gcgatgccac tattgctggt     180
gcttctggaa aagacaaaac ttcctcgact acaaaaacag aaacagctcc acaacaggga     240
gttgctgctg ggaaagaatc ctcagaaagt caaaaggcag gtgctgatac tggagtatca     300
```

```
ggagcggctg ctactacagc atcaaatact gcaacaaaaa ttgctatgca gacctctatt      360
gaagaggcga gcaaaagtat ggagtctacc ttagagtcac ttcaaagcct cagtgccgcg      420
caaatgaaag aagtcgaagc ggttgttgtt gctgccctct cagggaaaag ttcgggttcc      480
gcaaaattgg aaacacctga gctccccaag cccggggtga caccaagatc agaggttatc      540
gaaatcggac tcgcgcttgc taaagcaatt cagacattgg gagaagccac aaaatctgcc      600
ttatctaact atgcaagtac acaagcacaa gcagaccaaa caataaaact aggtctagaa      660
aagcaagcga taaaaatcga taaagaacga gaagaatacc aagagatgaa ggctgccgaa      720
cagaagtcta agatctcga aggaacaatg gatactgtca atactgtgat gatcgcg         777
```

<210> SEQ ID NO 8
<211> LENGTH: 1712
<212> TYPE: DNA
<213> ORGANISM: Chlamydophila pneumoniae

<400> SEQUENCE: 8

```
atgccaaaac aagctgaata tacttgggga tctaaaaaaa ttctggacaa tatagaatgc       60
ctcacagaag acgttgccga atttaaagat ttgctttata cggcacacag aattacttcg      120
agcgaagaag aatctgataa cgaaatacag cctggcgcca tcctaaaagg taccgtagtt      180
gatattaata aagactttgt cgtagttgat gttggtctga agtctgaggg agtgatccct      240
atgtcagagt tcatagactc ttcagaaggt ttagtgcttg agctgaagt agaagtctat       300 ctcgaccaag ccgaagacga agagggcaaa gttgtccttt ctagagaaaa agccacacga      360
caacgtcaat gggaatacat cttagctcat tgtgaagaag ttctattgt taaaggtcaa       420 attacacgta aagtcaaagg cggccttatt gtagatattg aatggaagc cttcctacct       480 ggatcacaaa ttgacaacaa gaaaatcaaa aatttagatg attatgtcgg aaaagttttgt     540 gaattcaaaa ttttaaaaat taacgttgaa cgtcgcaata ttgttgtctc aagaagagaa      600
ctcttagaag ctgagagaat ctctaagaaa gccgaactta ttgaacaaat ttctatcgga      660
gaataccgca aggagttgt taaaaacatt actgactttg gtgtattctt agatctcgat       720
ggtattgacg tcttctcca cattaccgat atgacctgga agcgcatacg acatccttcc       780
gaaatggtcg aattgaatca agagttggaa gtaattattt taagcgtaga taaagaaaaa      840
ggacgagttg ctctaggtct caaacaaaaa gagcataatc cttgggaaga tattgagaag      900 aaatacccttc ctggaaaacg agttcttggt aaaattgtga agcttctccc ctacggagct    960
ttcattgaaa ttgaagaggg cattgaaggt ctaattcaca tttctgaaat gtcttgggtg     1020
aaaaatattg tagatcctag tgaagtcgta ataaaggcg atgaagttga agccattgtt      1080
ctatctattc agaaggacga aggaaaaaatt tctctaggat aaagcaaac agaacgtaat    1140 ccttgggaca atatcgaaga aaaatatcct ataggtctcc atgtcaatgc tgaaatcaag    1200
aacttaacca attacggtgc tttcgttgaa ttagaaccag gaattgaggg tctgattcat    1260
atttctgaca tgagttggat taaaaagtc tctcacccttt cagaactatt caaaaaagga    1320
aattctgtag aggctgttat tttatcagta gacaagaaa gtaaaaaaat tactttagga    1380
gttaagcaat taagttctaa tccttggaat gaaattgaag ctatgttccc tgctggcaca     1440
gtaatttcag gagttgtgac taaaatcact gcatttggag ccttttgttga gctacaaaac   1500 gggattgaag gattgattca cgtttcagaa ctttctgaca agccctttgc aaaaattgaa    1560
gatattatct ccattggaga aaatgtttct gcaaaagtaa ttaagctaga tccagatcat    1620
```

-continued

```
aaaaaagttt ctctttctgt aaaagaatac ttagctgaca atgcttatga tcaagactct    1680
aggactgaat tagatttcaa ggattctcaa gg                                  1712

<210> SEQ ID NO 9
<211> LENGTH: 1048
<212> TYPE: DNA
<213> ORGANISM: Artificial Sequence
<220> FEATURE:
<223> OTHER INFORMATION: fusion polynucleotide
<220> FEATURE:
<221> NAME/KEY: CDS
<222> LOCATION: (236)..(1012)
<223> OTHER INFORMATION:
<220> FEATURE:
<221> NAME/KEY: misc_feature
<222> LOCATION: (1)..(1048)
<223> OTHER INFORMATION: Strain = YK-41, Immediate source = clone 53-3s

<400> SEQUENCE: 9
tcagtatcgg cggaattcga accccttcgc ggctctttct ggaactctag aatctttaca    60
tctcgaagag ttaactcaag gattattccc ttctgcccaa gaagatgcca acttcgcaaa   120
ggagttatct tcagtagtac acggattaaa aaacctaacc actgtagtta ataaacaaat   180
ggttaaaggc gctgagtaaa gccctttgca gaatcaaacc ccttaggata caaac atg    238
                                                              Met
                                                               1 tct att tca tct tct tca gga cct gac aat caa aaa aat atc atg tct    286
Ser Ile Ser Ser Ser Ser Gly Pro Asp Asn Gln Lys Asn Ile Met Ser
         5                  10                  15 caa gtt ctg aca tcg aca ccc cag ggc gtg ccc caa caa gat aag ctg    334
Gln Val Leu Thr Ser Thr Pro Gln Gly Val Pro Gln Gln Asp Lys Leu
     20                  25                  30 tct ggc aac gaa acg aag caa ata cag caa aca cgt cag ggt aaa aac    382
Ser Gly Asn Glu Thr Lys Gln Ile Gln Gln Thr Arg Gln Gly Lys Asn
 35                  40                  45 act gag atg gaa agc gat gcc act att gct ggt gct tct gga aaa gac    430
Thr Glu Met Glu Ser Asp Ala Thr Ile Ala Gly Ala Ser Gly Lys Asp
 50                  55                  60                  65 aaa act tcc tcg act aca aaa aca gaa aca gct cca caa cag gga gtt    478
Lys Thr Ser Ser Thr Thr Lys Thr Glu Thr Ala Pro Gln Gln Gly Val
                 70                  75                  80 gct gct ggg aaa gaa tcc tca gaa agt caa aag gca ggt gct gat act    526
Ala Ala Gly Lys Glu Ser Ser Glu Ser Gln Lys Ala Gly Ala Asp Thr
             85                  90                  95 gga gta tca gga gcg gct gct act aca gca tca aat act gca aca aaa    574
Gly Val Ser Gly Ala Ala Ala Thr Thr Ala Ser Asn Thr Ala Thr Lys
         100                 105                 110 att gct atg cag acc tct att gaa gag gcg agc aaa agt atg gag tct    622
Ile Ala Met Gln Thr Ser Ile Glu Glu Ala Ser Lys Ser Met Glu Ser
     115                 120                 125 acc tta gag tca ctt caa agc ctc agt gcc gcg caa atg aaa gaa gtc    670
Thr Leu Glu Ser Leu Gln Ser Leu Ser Ala Ala Gln Met Lys Glu Val
130                 135                 140                 145 gaa gcg gtt gtt gtt gct gcc ctc tca ggg aaa agt tcg ggt tcc gca    718
Glu Ala Val Val Val Ala Ala Leu Ser Gly Lys Ser Ser Gly Ser Ala
                 150                 155                 160 aaa ttg gaa aca cct gag ctc ccc aag ccc ggg gtg aca cca aga tca    766
Lys Leu Glu Thr Pro Glu Leu Pro Lys Pro Gly Val Thr Pro Arg Ser
             165                 170                 175 gag gtt atc gaa atc gga ctc gcg ctt gct aaa gca att cag aca ttg    814
Glu Val Ile Glu Ile Gly Leu Ala Leu Ala Lys Ala Ile Gln Thr Leu
         180                 185                 190
```

```
gga gaa gcc aca aaa tct gcc tta tct aac tat gca agt aca caa gca        862
Gly Glu Ala Thr Lys Ser Ala Leu Ser Asn Tyr Ala Ser Thr Gln Ala
        195                 200                 205 caa gca gac caa aca aat aaa cta ggt cta gaa aag caa gcg ata aaa        910
Gln Ala Asp Gln Thr Asn Lys Leu Gly Leu Glu Lys Gln Ala Ile Lys
210                 215                 220                 225 atc gat aaa gaa cga gaa gaa tac caa gag atg aag gct gcc gaa cag        958
Ile Asp Lys Glu Arg Glu Glu Tyr Gln Glu Met Lys Ala Ala Glu Gln
                230                 235                 240 aag tct aaa gat ctc gaa gga aca atg gat act gtc aat act gtg atg       1006
Lys Ser Lys Asp Leu Glu Gly Thr Met Asp Thr Val Asn Thr Val Met
            245                 250                 255 atc gcg aaggggttcg aattccagct gagcgccggt cgctac                       1048
Ile Ala
```

<210> SEQ ID NO 10
<211> LENGTH: 5658
<212> TYPE: DNA
<213> ORGANISM: Artificial Sequence
<220> FEATURE:
<223> OTHER INFORMATION: fusion polynucleotide

<400> SEQUENCE: 10

```
atcgatgtta acagatctaa gcttaactaa ctaactccgg aaaaggagga acttccatga      60
tcagtctgat tgcggcgtta gcggtagatc gcgttatcgg catggaaaac gccatgccgt     120
ggaacctgcc tgccgatctc gcctggttta acgcaacac cttaaataaa cccgtgatta      180
tgggccgcca tacctgggaa tcaatcggtc gtccgttgcc aggacgcaaa aatattatcc     240
tcagcagtca accgggtacg gacgatcgcg taacgtgggt gaagtcggtg gatgaagcca     300
tcgcggcgtg tggtgacgta ccagaaatca tggtgattgg cggcggtcgc gtttatgaac     360
agttcttgcc aaaagcgcaa aaactgtatc tgacgcatat cgacgcagaa gtggaaggcg     420
acacccattt cccggattac gagccggatg actgggaatc ggtattcagc gaattccacg     480
atgctgatgc gcagaactct cacagctatg agttcgaaat tctggagcgg cggatccaat     540
tcgaaccct tcgcggctct ttctggaact ctagaatctt tacatctcga agagttaact      600
caaggattat tcccttctgc caagaagat gccaacttcg caaggagtt atcttcagta       660
gtacacggat taaaaaacct aaccactgta gttaataaac aaatggttaa aggcgctgag     720
taaagccctt tgcagaatca aaccccttag gatacaaaca tgtctatttc atcttcttca     780
ggacctgaca atcaaaaaaa tatcatgtct caagttctga catcgacacc ccagggcgtg     840
ccccaacaag ataagctgtc tggcaacgaa acgaagcaaa tacagcaaac acgtcagggt     900
aaaaacactg agatggaaag cgatgccact attgctggtg cttctggaaa agacaaaact     960
tcctcgacta caaaaacaga aacagctcca caacagggag ttgctgctgg gaaagaatcc    1020
tcagaaagtc aaaaggcagg tgctgatact ggagtatcag gagcggctgc tactacagca    1080
tcaaatactg caacaaaaat tgctatgcag acctctattg aagaggcgag caaaagtatg    1140
gagtctacct tagagtcact tcaaaagcctc agtgccgcgc aaatgaaaga agtcgaagcg    1200
gttgttgttg ctgccctctc agggaaaagt tcgggttccg caaaattgga aacacctgag    1260
ctccccaagc ccggggtgac accaagatca gaggttatcg aaatcggact cgcgcttgct    1320
aaagcaattc agacattggg agaagccaca aaatctgcct tatctaacta tgcaagtaca    1380
caagcacaag cagaccaaac aaataaaacta ggtctagaaa agcaagcgat aaaaatcgat    1440
aaagaacgag aagaatacca agagatgaag gctgccgaac agaagtctaa agatctcgaa    1500
```

```
ggaacaatgg atactgtcaa tactgtgatg atcgcgaagg ggttcgaatt gccatggggg    1560
cccttaatta attaactcga gagatccaga tctaatcgat gatcctctac gccggacgca    1620
tcgtggccgg catcaccggc gccacaggtg cggttgctgg cgcctatatc gccgacatca    1680
ccgatgggga agatcgggct cgccacttcg ggctcatgag cgcttgtttc ggcgtgggta    1740
tggtggcagg cccgtggccg ggggactgtt gggcgccatc tccttgcatg caccattcct    1800
tgcggcggcg gtgctcaacg gcctcaacct actactgggc tgcttcctaa tgcaggagtc    1860
gcataaggga gagcgtcgac cgatgccctt gagagccttc aacccagtca gctccttccg    1920
gtgggcgcgg ggcatgacta tcgtcgccgc acttatgact gtcttcttta tcatgcaact    1980
cgtaggacag gtgccggcag cgctctgggt cattttcggc gaggaccgct ttcgctggag    2040
cgcgacgatg atcggcctgt cgcttgcggt attcggaatc ttgcacgccc tcgctcaagc    2100
cttcgtcact ggtcccgcca ccaaacgttt cggcgagaag caggccatta tcgccggcat    2160
ggcggccgac gcgctgggct acgtcttgct ggcgttcgcg acgcgaggct ggatggcctt    2220
ccccattatg attcttctcg cttccggcgg catcgggatg cccgcgttgc aggccatgct    2280
gtccaggcag gtagatgacg accatcaggg acagcttcaa ggatcgctcg cggctcttac    2340
cagcctaact tcgatcactg gaccgctgat cgtcacggcg atttatgccg cctcggcgag    2400
cacatggaac gggttggcat ggattgtagg cgccgcccta taccttgtct gcctccccgc    2460
gttgcgtcgc ggtgcatgga gccgggccac ctcgacctga atggaagccg gcggcacctc    2520
gctaacggat tcaccactcc aagaattgga gccaatcaat tcttgcggag aactgtgaat    2580
gcgcaaacca acccttggca gaacatatcc atcgcgtccg ccatctccag cagccgcacg    2640
cggcgcatct cgggcagcgt tgggtcctgg ccacgggtgc gcatgatcgt gctcctgtcg    2700
ttgaggaccc ggctaggctg gcggggttgc cttactggtt agcagaatga atcaccgata    2760
cgcgagcgaa cgtgaagcga ctgctgctgc aaaacgtctg cgacctgagc aacaacatga    2820
atggtcttcg gtttccgtgt ttcgtaaagt ctggaaacgc ggaagtcagc gccctgcacc    2880
attatgttcc ggatctgcat cgcaggatgc tgctggctac cctgtggaac acctacatct    2940
gtattaacga agcgctggca ttgaccctga gtgatttttc tctggtcccg ccgcatccat    3000
accgccagtt gtttaccctc acaacgttcc agtaaccggg catgttcatc atcagtaacc    3060
cgtatcgtga gcatcctctc tcgtttcatc ggtatcatta cccccatgaa cagaaattcc    3120
cccttacacg gaggcatcaa gtgaccaaac aggaaaaaac cgcccttaac atggcccgct    3180
ttatcagaag ccagacatta acgcttctgg agaaactcaa cgagctggac gcggatgaac    3240
aggcagacat ctgtgaatcg cttcacgacc acgctgatga gctttaccgc agctgcctcg    3300
cgcgtttcgg tgatgacggt gaaaacctct gacacatgca gctcccggag acggtcacag    3360
cttgtctgta agcggatgcc gggagcagac aagcccgtca gggcgcgtca gcgggtgttg    3420
gcgggtgtcg ggcgcagcc atgacccagt cacgtagcga tagcggagtg tatactggct    3480
taactatgcg gcatcagagc agattgtact gagagtgcac catatgcggt gtgaaatacc    3540
gcacagatgc gtaaggagaa ataccgcat caggcgctct ccgcttcct cgctcactga    3600 ctcgctgcgc tcggtcgttc ggctgcggcg agcggtatca gctcactcaa aggcggtaat    3660
acggttatcc acagaatcag gggataacgc aggaaagaac atgtgagcaa aaggccagca    3720
aaaggccagg aaccgtaaaa aggccgcgtt gctggcgttt ttccataggc tccgcccccc    3780
tgacgagcat cacaaaaatc gacgctcaag tcagaggtgg cgaaacccga caggactata    3840
```

-continued

```
aagataccag gcgtttcccc ctggaagctc cctcgtgcgc tctcctgttc cgaccctgcc    3900
gcttaccgga tacctgtccg cctttctccc ttcgggaagc gtggcgcttt ctcaatgctc    3960
acgctgtagg tatctcagtt cggtgtaggt cgttcgctcc aagctgggct gtgtgcacga    4020
accccccgtt cagcccgacc gctgcgcctt atccggtaac tatcgtcttg agtccaaccc    4080
ggtaagacac gacttatcgc cactggcagc agccactggt aacaggatta gcagagcgag    4140
gtatgtaggc ggtgctacag agttcttgaa gtggtggcct aactacggct acactagaag    4200
gacagtattt ggtatctgcg ctctgctgaa gccagttacc ttcggaaaaa gagttggtag    4260
ctcttgatcc ggcaaacaaa ccaccgctgg tagcggtggt ttttttgttt gcaagcagca    4320
gattacgcgc agaaaaaaag gatctcaaga agatcctttg atcttttcta cggggtctga    4380
cgctcagtgg aacgaaaact cacgttaagg gattttggtc atgagattat caaaaaggat    4440
cttcacctag atcctttta attaaaaatg aagttttaaa tcaatctaaa gtatatatga    4500
gtaaacttgg tctgacagtt accaatgctt aatcagtgag gcacctatct cagcgatctg    4560
tctatttcgt tcatccatag ttgcctgact ccccgtcgtg tagataacta cgatacggga    4620
gggcttacca tctggcccca gtgctgcaat gataccgcga gacccacgct caccggctcc    4680
agatttatca gcaataaacc agccagccgg aagggccgag cgcagaagtg gtcctgcaac    4740
tttatccgcc tccatccagt ctattaattg ttgccgggaa gctagagtaa gtagttcgcc    4800
agttaatagt ttgcgcaacg ttgttgccat tgctgcaggc atcgtggtgt cacgctcgtc    4860
gtttggtatg gcttcattca gctccggttc ccaacgatca aggcgagtta catgatcccc    4920
catgttgtgc aaaaaagcgg ttagctcctt cggtcctccg atcgttgtca gaagtaagtt    4980
ggccgcagtg ttatcactca tggttatggc agcactgcat aattctctta ctgtcatgcc    5040
atccgtaaga tgcttttctg tgactggtga gtactcaacc aagtcattct gagaatagtg    5100
tatgcggcga ccgagttgct cttgcccggc gtcaacacgg gataataccg cgccacatag    5160
cagaacttta aaagtgctca tcattggaaa acgttcttcg gggcgaaaac tctcaaggat    5220
cttaccgctg ttgagatcca gttcgatgta acccactcgt gcacccaact gatcttcagc    5280
atcttttact ttcaccagcg tttctgggtg agcaaaaaca ggaaggcaaa atgccgcaaa    5340
aaagggaata agggcgacac ggaaatgttg aatactcata ctcttccttt ttcaatatta    5400
ttgaagcatt tatcagggtt attgtctcat gagcggatac atatttgaat gtatttagaa    5460
aaataaacaa ataggggttc cgcgcacatt tccccgaaaa gtgccacctg acgtctaaga    5520
aaccattatt atcatgacat taacctataa aaataggcgt atcacgaggc cctttcgtct    5580
tcaagaatta attgttatcc gctcacaatt aattcttgac aattagttaa ctatttgtta    5640
taatgtattc ataagctt                                                  5658
```

<210> SEQ ID NO 11
<211> LENGTH: 35
<212> TYPE: DNA
<213> ORGANISM: Artificial Sequence
<220> FEATURE:
<223> OTHER INFORMATION: Synthetic DNA

<400> SEQUENCE: 11
gatccaattg ccatgggggc ccttaattaa ttaac     35

<210> SEQ ID NO 12
<211> LENGTH: 35
<212> TYPE: DNA
<213> ORGANISM: Artificial Sequence

```
<220> FEATURE:
<223> OTHER INFORMATION: Synthetic DNA

<400> SEQUENCE: 12
tcgagttaat taattaaggg cccccatggc aattg                                35

<210> SEQ ID NO 13
<211> LENGTH: 1927
<212> TYPE: DNA
<213> ORGANISM: Artificial Sequence
<220> FEATURE:
<223> OTHER INFORMATION: fusion polynucleotide
<220> FEATURE:
<221> NAME/KEY: -35_signal
<222> LOCATION: (146)..(151)
<223> OTHER INFORMATION: Identification by similarity with known
      sequence or to an established consensus sequence.
<220> FEATURE:
<221> NAME/KEY: -10_signal
<222> LOCATION: (169)..(174)
<223> OTHER INFORMATION: Identification by similarity with known
      sequence or to an established consensus sequence.
<220> FEATURE:
<221> NAME/KEY: RBS
<222> LOCATION: (199)..(205)
<223> OTHER INFORMATION: Identification by similarity with known
      sequence or to an established consensus sequence.
<220> FEATURE:
<221> NAME/KEY: CDS
<222> LOCATION: (188)..(1927)
<223> OTHER INFORMATION:

<400> SEQUENCE: 13
gcgaccggcg ctcagctgga attcgaaccc cttcgcctta tacatctcta gaacggaagt      60
ataggatttt acgattaatt cgattatata gaactaatcg tctcctgcaa gggaggtctt     120
gcctttttta aggtttatat ttacactgtc tttttgact ttgtagtttt taggagaata     180 acaataa atg cca aaa caa gct gaa tat act tgg gga tct aaa aaa att      229
        Met Pro Lys Gln Ala Glu Tyr Thr Trp Gly Ser Lys Lys Ile
        1               5                   10 ctg gac aat ata gaa tgc ctc aca gaa gac gtt gcc gaa ttt aaa gat      277
Leu Asp Asn Ile Glu Cys Leu Thr Glu Asp Val Ala Glu Phe Lys Asp
15                  20                  25                  30 ttg ctt tat acg gca cac aga att act tcg agc gaa gaa gaa tct gat      325
Leu Leu Tyr Thr Ala His Arg Ile Thr Ser Ser Glu Glu Glu Ser Asp
                35                  40                  45 aac gaa ata cag cct ggc gcc atc cta aaa ggt acc gta gtt gat att      373
Asn Glu Ile Gln Pro Gly Ala Ile Leu Lys Gly Thr Val Val Asp Ile
            50                  55                  60 aat aaa gac ttt gtc gta gtt gat gtt ggt ctg aag tct gag gga gtg      421
Asn Lys Asp Phe Val Val Val Asp Val Gly Leu Lys Ser Glu Gly Val
65                  70                  75 atc cct atg tca gag ttc ata gac tct tca gaa ggt tta gtg ctt gga      469
Ile Pro Met Ser Glu Phe Ile Asp Ser Ser Glu Gly Leu Val Leu Gly
            80                  85                  90 gct gaa gta gaa gtc tat ctc gac caa gcc gaa gac gaa gag ggc aaa      517
Ala Glu Val Glu Val Tyr Leu Asp Gln Ala Glu Asp Glu Glu Gly Lys
        95                  100                 105             110 gtt gtc ctt tct aga gaa aaa gcc aca cga caa cgt caa tgg gaa tac      565
Val Val Leu Ser Arg Glu Lys Ala Thr Arg Gln Arg Gln Trp Glu Tyr
                115                 120                 125 atc tta gct cat tgt gaa gaa ggt tct att gtt aaa ggt caa att aca      613
Ile Leu Ala His Cys Glu Glu Gly Ser Ile Val Lys Gly Gln Ile Thr
            130                 135                 140 cgt aaa gtc aaa ggc ggc ctt att gta gat att gga atg gaa gcc ttc      661
```

```
                    Arg Lys Val Lys Gly Gly Leu Ile Val Asp Ile Gly Met Glu Ala Phe
                                    145                 150                 155 cta cct gga tca caa att gac aac aag atc aaa aat tta gat gat tat            709
Leu Pro Gly Ser Gln Ile Asp Asn Lys Ile Lys Asn Leu Asp Asp Tyr
    160                 165                 170 gtc gga aaa gtt tgt gaa ttc aaa aaa att tta aaa att aac gtt gaa            757
Val Gly Lys Val Cys Glu Phe Lys Lys Ile Leu Lys Ile Asn Val Glu
175                 180                 185                 190 cgt cgc aat att gtt gtc tca aga aga gaa ctc tta gaa gct gag aga            805
Arg Arg Asn Ile Val Val Ser Arg Arg Glu Leu Leu Glu Ala Glu Arg
                195                 200                 205 atc tct aag aaa gcc gaa ctt att gaa caa att tct atc gga gaa tac            853
Ile Ser Lys Lys Ala Glu Leu Ile Glu Gln Ile Ser Ile Gly Glu Tyr
        210                 215                 220 cgc aaa gga gtt gtt aaa aac att act gac ttt ggt gta ttc tta gat            901
Arg Lys Gly Val Val Lys Asn Ile Thr Asp Phe Gly Val Phe Leu Asp
            225                 230                 235 ctc gat ggt att gac ggt ctt ctc cac att acc gat atg acc tgg aag            949
Leu Asp Gly Ile Asp Gly Leu Leu His Ile Thr Asp Met Thr Trp Lys
    240                 245                 250 cgc ata cga cat cct tcc gaa atg gtc gaa ttg aat caa gag ttg gaa            997
Arg Ile Arg His Pro Ser Glu Met Val Glu Leu Asn Gln Glu Leu Glu
255                 260                 265                 270 gta att att tta agc gta gat aaa gaa aaa gga cga gtt gct cta ggt           1045
Val Ile Ile Leu Ser Val Asp Lys Glu Lys Gly Arg Val Ala Leu Gly
                275                 280                 285 ctc aaa caa aaa gag cat aat cct tgg gaa gat att gag aag aaa tac           1093
Leu Lys Gln Lys Glu His Asn Pro Trp Glu Asp Ile Glu Lys Lys Tyr
        290                 295                 300 cct cct gga aaa cga gtt ctt ggt aaa att gtg aag ctt ctc ccc tac           1141
Pro Pro Gly Lys Arg Val Leu Gly Lys Ile Val Lys Leu Leu Pro Tyr
            305                 310                 315 gga gct ttc att gaa att gaa gag ggc att gaa ggt cta att cac att           1189
Gly Ala Phe Ile Glu Ile Glu Glu Gly Ile Glu Gly Leu Ile His Ile
    320                 325                 330 tct gaa atg tct tgg gtg aaa aat att gta gat cct agt gaa gtc gta           1237
Ser Glu Met Ser Trp Val Lys Asn Ile Val Asp Pro Ser Glu Val Val
335                 340                 345                 350 aat aaa ggc gat gaa gtt gaa gcc att gtt cta tct att cag aag gac           1285
Asn Lys Gly Asp Glu Val Glu Ala Ile Val Leu Ser Ile Gln Lys Asp
                355                 360                 365 gaa gga aaa att tct cta gga tta aag caa aca gaa cgt aat cct tgg           1333
Glu Gly Lys Ile Ser Leu Gly Leu Lys Gln Thr Glu Arg Asn Pro Trp
        370                 375                 380 gac aat atc gaa gaa aaa tat cct ata ggt ctc cat gtc aat gct gaa           1381
Asp Asn Ile Glu Glu Lys Tyr Pro Ile Gly Leu His Val Asn Ala Glu
            385                 390                 395 atc aag aac tta acc aat tac ggt gct ttc gtt gaa tta gaa cca gga           1429
Ile Lys Asn Leu Thr Asn Tyr Gly Ala Phe Val Glu Leu Glu Pro Gly
    400                 405                 410 att gag ggt ctg att cat att tct gac atg agt tgg att aaa aaa gtc           1477
Ile Glu Gly Leu Ile His Ile Ser Asp Met Ser Trp Ile Lys Lys Val
415                 420                 425                 430 tct cac cct tca gaa cta ttc aaa aaa gga aat tct gta gag gct gtt           1525
Ser His Pro Ser Glu Leu Phe Lys Lys Gly Asn Ser Val Glu Ala Val
                435                 440                 445 att tta tca gta gac aaa gaa agt aaa aaa att act tta gga gtt aag           1573
Ile Leu Ser Val Asp Lys Glu Ser Lys Lys Ile Thr Leu Gly Val Lys
        450                 455                 460
```

```
caa tta agt tct aat cct tgg aat gaa att gaa gct atg ttc cct gct    1621
Gln Leu Ser Ser Asn Pro Trp Asn Glu Ile Glu Ala Met Phe Pro Ala
        465                 470                 475 ggc aca gta att tca gga gtt gtg act aaa atc act gca ttt gga gcc    1669
Gly Thr Val Ile Ser Gly Val Val Thr Lys Ile Thr Ala Phe Gly Ala
    480                 485                 490 ttt gtt gag cta caa aac ggg att gaa gga ttg att cac gtt tca gaa    1717
Phe Val Glu Leu Gln Asn Gly Ile Glu Gly Leu Ile His Val Ser Glu
495                 500                 505                 510 ctt tct gac aag ccc ttt gca aaa att gaa gat att atc tcc att gga    1765
Leu Ser Asp Lys Pro Phe Ala Lys Ile Glu Asp Ile Ile Ser Ile Gly
                515                 520                 525 gaa aat gtt tct gca aaa gta att aag cta gat cca gat cat aaa aaa    1813
Glu Asn Val Ser Ala Lys Val Ile Lys Leu Asp Pro Asp His Lys Lys
            530                 535                 540 gtt tct ctt tct gta aaa gaa tac tta gct gac aat gct tat gat caa    1861
Val Ser Leu Ser Val Lys Glu Tyr Leu Ala Asp Asn Ala Tyr Asp Gln
        545                 550                 555 gac tct agg act gaa tta gat ttc aag gat tct caa ggc gaa ggg gtt    1909
Asp Ser Arg Thr Glu Leu Asp Phe Lys Asp Ser Gln Gly Glu Gly Val
    560                 565                 570 cga att ccg ccg ata ctg                                            1927
Arg Ile Pro Pro Ile Leu
575             580
```

<210> SEQ ID NO 14
<211> LENGTH: 160
<212> TYPE: PRT
<213> ORGANISM: Artificial Sequence
<220> FEATURE:
<223> OTHER INFORMATION: fusion peptide

<400> SEQUENCE: 14

```
Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Glu Phe Glu Ile Leu Glu Arg Arg Ile
145                 150                 155                 160
```

<210> SEQ ID NO 15
<211> LENGTH: 649
<212> TYPE: PRT
<213> ORGANISM: Artificial Sequence
<220> FEATURE:
<223> OTHER INFORMATION: fusion peptide -continued

<400> SEQUENCE: 15

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Glu Phe Glu Ile Leu Glu Arg Arg Ile
145                 150                 155                 160

Leu Met Ser Ile Ser Ser Ser Gly Pro Asp Asn Gln Lys Asn Ile
                165                 170                 175

Met Ser Gln Val Leu Thr Ser Thr Pro Gln Gly Val Pro Gln Gln Asp
            180                 185                 190

Lys Leu Ser Gly Asn Glu Thr Lys Gln Ile Gln Gln Thr Arg Gln Gly
        195                 200                 205

Lys Asn Thr Glu Met Glu Ser Asp Ala Thr Ile Ala Gly Ala Ser Gly
    210                 215                 220

Lys Asp Lys Thr Ser Ser Thr Thr Lys Thr Glu Thr Ala Pro Gln Gln
225                 230                 235                 240

Gly Val Ala Ala Gly Lys Glu Ser Ser Glu Ser Gln Lys Ala Gly Ala
                245                 250                 255

Asp Thr Gly Val Ser Gly Ala Ala Thr Thr Ala Ser Asn Thr Ala
            260                 265                 270

Thr Lys Ile Ala Met Gln Thr Ser Ile Glu Glu Ala Ser Lys Ser Met
        275                 280                 285

Glu Ser Thr Leu Glu Ser Leu Gln Ser Leu Ser Ala Ala Gln Met Lys
    290                 295                 300

Glu Val Glu Ala Val Val Ala Ala Leu Ser Gly Lys Ser Ser Gly
305                 310                 315                 320

Ser Ala Lys Leu Glu Thr Pro Glu Leu Pro Lys Pro Gly Val Thr Pro
                325                 330                 335

Arg Ser Glu Val Ile Glu Ile Gly Leu Ala Leu Ala Lys Ala Ile Gln
            340                 345                 350

Thr Leu Gly Glu Ala Thr Lys Ser Ala Leu Ser Asn Tyr Ala Ser Thr
        355                 360                 365

Gln Ala Gln Ala Asp Gln Thr Asn Lys Leu Gly Leu Glu Lys Gln Ala
    370                 375                 380

Ile Lys Ile Asp Lys Glu Arg Glu Glu Tyr Gln Glu Met Lys Ala Ala
385                 390                 395                 400

Glu Gln Lys Ser Lys Asp Leu Glu Gly Thr Met Asp Thr Val Asn Thr

```
                        405                 410                 415
Val Met Ile Ala Val Ser Val Ala Ile Thr Val Ile Ser Ile Val Ala
                420                 425                 430

Ala Ile Phe Thr Cys Gly Ala Gly Leu Ala Gly Leu Ala Ala Gly Ala
            435                 440                 445

Ala Val Gly Ala Ala Ala Gly Gly Ala Ala Gly Ala Ala Ala Ala
        450                 455                 460

Thr Thr Val Ala Thr Gln Ile Thr Val Gln Ala Val Gln Ala Val
465                 470                 475                 480

Lys Gln Ala Val Ile Thr Ala Val Arg Gln Ala Ile Thr Ala Ala Ile
                485                 490                 495

Lys Ala Ala Val Lys Ser Gly Ile Lys Ala Phe Ile Lys Thr Leu Val
            500                 505                 510

Lys Ala Ile Ala Lys Ala Ile Ser Lys Gly Ile Ser Lys Val Phe Ala
            515                 520                 525

Lys Gly Thr Gln Met Ile Ala Lys Asn Phe Pro Lys Leu Ser Lys Val
        530                 535                 540

Ile Ser Ser Leu Thr Ser Lys Trp Val Thr Val Gly Val Gly Val Val
545                 550                 555                 560

Val Ala Ala Pro Ala Leu Gly Lys Gly Ile Met Gln Met Gln Leu Ser
                565                 570                 575

Glu Met Gln Gln Asn Val Ala Gln Phe Gln Lys Glu Val Gly Lys Leu
            580                 585                 590

Gln Ala Ala Ala Asp Met Ile Ser Met Phe Thr Gln Phe Trp Gln Gln
        595                 600                 605

Ala Ser Lys Ile Ala Ser Lys Gln Thr Gly Glu Ser Asn Glu Met Thr
            610                 615                 620

Gln Lys Ala Thr Lys Leu Gly Ala Gln Ile Leu Lys Ala Tyr Ala Ala
625                 630                 635                 640

Ile Ser Gly Ala Ile Ala Gly Ala Ala
                645

<210> SEQ ID NO 16
<211> LENGTH: 432
<212> TYPE: PRT
<213> ORGANISM: Artificial Sequence
<220> FEATURE:
<223> OTHER INFORMATION: fusion peptide

<400> SEQUENCE: 16

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
                20                  25                  30

Arg Asn Thr Leu Asn Lys Pro Val Ile Met Gly Arg His Thr Trp Glu
            35                  40                  45

Ser Ile Gly Arg Pro Leu Pro Gly Arg Lys Asn Ile Ile Leu Ser Ser
        50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
```

```
                115                 120                 125
Glu Pro Asp Asp Trp Glu Ser Val Phe Ser Glu Phe His Asp Ala Asp
        130                 135                 140

Ala Gln Asn Ser His Ser Tyr Glu Phe Glu Ile Leu Glu Arg Arg Ile
145                 150                 155                 160

Leu Met Ser Ile Ser Ser Ser Gly Pro Asp Asn Gln Lys Asn Ile
                165                 170                 175

Met Ser Gln Val Leu Thr Ser Thr Pro Gln Gly Val Pro Gln Gln Asp
            180                 185                 190

Lys Leu Ser Gly Asn Glu Thr Lys Gln Ile Gln Gln Thr Arg Gln Gly
        195                 200                 205

Lys Asn Thr Glu Met Glu Ser Asp Ala Thr Ile Ala Gly Ala Ser Gly
    210                 215                 220

Lys Asp Lys Thr Ser Ser Thr Thr Lys Thr Glu Thr Ala Pro Gln Gln
225                 230                 235                 240

Gly Val Ala Ala Gly Lys Glu Ser Ser Glu Ser Gln Lys Ala Gly Ala
                245                 250                 255

Asp Thr Gly Val Ser Gly Ala Ala Thr Thr Ala Ser Asn Thr Ala
            260                 265                 270

Thr Lys Ile Ala Met Gln Thr Ser Ile Glu Glu Ala Ser Lys Ser Met
        275                 280                 285

Glu Ser Thr Leu Glu Ser Leu Gln Ser Leu Ser Ala Ala Gln Met Lys
    290                 295                 300

Glu Val Glu Ala Val Val Ala Ala Leu Ser Gly Lys Ser Ser Gly
305                 310                 315                 320

Ser Ala Lys Leu Glu Thr Pro Glu Leu Pro Lys Pro Gly Val Thr Pro
                325                 330                 335

Arg Ser Glu Val Ile Glu Ile Gly Leu Ala Leu Ala Lys Ala Ile Gln
            340                 345                 350

Thr Leu Gly Glu Ala Thr Lys Ser Ala Leu Ser Asn Tyr Ala Ser Thr
        355                 360                 365

Gln Ala Gln Ala Asp Gln Thr Asn Lys Leu Gly Leu Glu Lys Gln Ala
    370                 375                 380

Ile Lys Ile Asp Lys Glu Arg Glu Glu Tyr Gln Glu Met Lys Ala Ala
385                 390                 395                 400

Glu Gln Lys Ser Lys Asp Leu Glu Gly Thr Met Asp Thr Val Asn Thr
                405                 410                 415

Val Met Ile Ala Lys Gly Phe Glu Leu Pro Trp Gly Pro Leu Ile Asn
            420                 425                 430

<210> SEQ ID NO 17
<211> LENGTH: 1947
<212> TYPE: DNA
<213> ORGANISM: Artificial Sequence
<220> FEATURE:
<223> OTHER INFORMATION: fusion polynucleotide
<220> FEATURE:
<221> NAME/KEY: CDS
<222> LOCATION: (1)..(1947)
<223> OTHER INFORMATION:

<400> SEQUENCE: 17 atg atc agt ctg att gcg gcg tta gcg gta gat cgc gtt atc ggc atg        48
Met Ile Ser Leu Ile Ala Ala Leu Ala Val Asp Arg Val Ile Gly Met
1               5                   10                  15 gaa aac gcc atg ccg tgg aac ctg cct gcc gat ctc gcc tgg ttt aaa        96
Glu Asn Ala Met Pro Trp Asn Leu Pro Ala Asp Leu Ala Trp Phe Lys
```

```
                 20                    25                    30
cgc aac acc tta aat aaa ccc gtg att atg ggc cgc cat acc tgg gaa      144
Arg Asn Thr Leu Asn Lys Pro Val Ile Met Gly Arg His Thr Trp Glu
             35                    40                    45 tca atc ggt cgt ccg ttg cca gga cgc aaa aat att atc ctc agc agt      192
Ser Ile Gly Arg Pro Leu Pro Gly Arg Lys Asn Ile Ile Leu Ser Ser
 50                    55                    60 caa ccg ggt acg gac gat cgc gta acg tgg gtg aag tcg gtg gat gaa      240
Gln Pro Gly Thr Asp Asp Arg Val Thr Trp Val Lys Ser Val Asp Glu
 65                    70                    75                    80 gcc atc gcg gcg tgt ggt gac gta cca gaa atc atg gtg att ggc ggc      288
Ala Ile Ala Ala Cys Gly Asp Val Pro Glu Ile Met Val Ile Gly Gly
                 85                    90                    95 ggt cgc gtt tat gaa cag ttc ttg cca aaa gcg caa aaa ctg tat ctg      336
Gly Arg Val Tyr Glu Gln Phe Leu Pro Lys Ala Gln Lys Leu Tyr Leu
             100                   105                   110 acg cat atc gac gca gaa gtg gaa ggc gac acc cat ttc ccg gat tac      384
Thr His Ile Asp Ala Glu Val Glu Gly Asp Thr His Phe Pro Asp Tyr
             115                   120                   125 gag ccg gat gac tgg gaa tcg gta ttc agc gaa ttc cac gat gct gat      432
Glu Pro Asp Asp Trp Glu Ser Val Phe Ser Glu Phe His Asp Ala Asp
             130                   135                   140 gcg cag aac tct cac agc tat gag ttc gaa att ctg gag cgg cgg atc      480
Ala Gln Asn Ser His Ser Tyr Glu Phe Glu Ile Leu Glu Arg Arg Ile
145                   150                   155                   160 ctg atg tct att tca tct tct tca gga cct gac aat caa aaa aat atc      528
Leu Met Ser Ile Ser Ser Ser Ser Gly Pro Asp Asn Gln Lys Asn Ile
                 165                   170                   175 atg tct caa gtt ctg aca tcg aca ccc cag ggc gtg ccc caa caa gat      576
Met Ser Gln Val Leu Thr Ser Thr Pro Gln Gly Val Pro Gln Gln Asp
             180                   185                   190 aag ctg tct ggc aac gaa acg aag caa ata cag caa aca cgt cag ggt      624
Lys Leu Ser Gly Asn Glu Thr Lys Gln Ile Gln Gln Thr Arg Gln Gly
             195                   200                   205 aaa aac act gag atg gaa agc gat gcc act att gct ggt gct tct gga      672
Lys Asn Thr Glu Met Glu Ser Asp Ala Thr Ile Ala Gly Ala Ser Gly
             210                   215                   220 aaa gac aaa act tcc tcg act aca aaa aca gaa aca gct cca caa cag      720
Lys Asp Lys Thr Ser Ser Thr Thr Lys Thr Glu Thr Ala Pro Gln Gln
225                   230                   235                   240 gga gtt gct gct ggg aaa gaa tcc tca gaa agt caa aag gca ggt gct      768
Gly Val Ala Ala Gly Lys Glu Ser Ser Glu Ser Gln Lys Ala Gly Ala
                 245                   250                   255 gat act gga gta tca gga gcg gct gct act aca gca tca aat act gca      816
Asp Thr Gly Val Ser Gly Ala Ala Ala Thr Thr Ala Ser Asn Thr Ala
             260                   265                   270 aca aaa att gct atg cag acc tct att gaa gag gcg agc aaa agt atg      864
Thr Lys Ile Ala Met Gln Thr Ser Ile Glu Glu Ala Ser Lys Ser Met
             275                   280                   285 gag tct acc tta gag tca ctt caa agc ctc agt gcc gcg caa atg aaa      912
Glu Ser Thr Leu Glu Ser Leu Gln Ser Leu Ser Ala Ala Gln Met Lys
             290                   295                   300 gaa gtc gaa gcg gtt gtt gtt gct gcc ctc tca ggg aaa agt tcg ggt      960
Glu Val Glu Ala Val Val Val Ala Ala Leu Ser Gly Lys Ser Ser Gly
305                   310                   315                   320 tcc gca aaa ttg gaa aca cct gag ctc ccc aag ccc ggg gtg aca cca     1008
Ser Ala Lys Leu Glu Thr Pro Glu Leu Pro Lys Pro Gly Val Thr Pro
                 325                   330                   335 aga tca gag gtt atc gaa atc gga ctc gcg ctt gct aaa gca att cag     1056
```

-continued

```
Arg Ser Glu Val Ile Glu Ile Gly Leu Ala Leu Ala Lys Ala Ile Gln
            340                 345                 350 aca ttg gga gaa gcc aca aaa tct gcc tta tct aac tat gca agt aca      1104
Thr Leu Gly Glu Ala Thr Lys Ser Ala Leu Ser Asn Tyr Ala Ser Thr
            355                 360                 365 caa gca caa gca gac caa aca aat aaa cta ggt cta gaa aag caa gcg      1152
Gln Ala Gln Ala Asp Gln Thr Asn Lys Leu Gly Leu Glu Lys Gln Ala
370                 375                 380 ata aaa atc gat aaa gaa cga gaa gaa tac caa gag atg aag gct gcc      1200
Ile Lys Ile Asp Lys Glu Arg Glu Glu Tyr Gln Glu Met Lys Ala Ala
385                 390                 395                 400 gaa cag aag tct aaa gat ctc gaa gga aca atg gat act gtc aat act      1248
Glu Gln Lys Ser Lys Asp Leu Glu Gly Thr Met Asp Thr Val Asn Thr
                405                 410                 415 gtg atg atc gcg gtt tct gtt gcc att aca gtt att tct att gtt gct      1296
Val Met Ile Ala Val Ser Val Ala Ile Thr Val Ile Ser Ile Val Ala
            420                 425                 430 gct att ttt aca tgc gga gct gga ctc gct gga ctc gct gcg gga gct      1344
Ala Ile Phe Thr Cys Gly Ala Gly Leu Ala Gly Leu Ala Ala Gly Ala
            435                 440                 445 gct gta ggt gca gcg gca gct gga ggt gca gca gga gct gct gcc gca      1392
Ala Val Gly Ala Ala Ala Gly Gly Ala Ala Gly Ala Ala Ala Ala
450                 455                 460 acc acg gta gca aca caa att aca gtt caa gct gtt gtc caa gcg gtg      1440
Thr Thr Val Ala Thr Gln Ile Thr Val Gln Ala Val Val Gln Ala Val
465                 470                 475                 480 aaa caa gct gtt atc aca gct gtc aga caa gcg atc acc gcg gct ata      1488
Lys Gln Ala Val Ile Thr Ala Val Arg Gln Ala Ile Thr Ala Ala Ile
                485                 490                 495 aaa gcg gct gtc aaa tct gga ata aaa gca ttt atc aaa act tta gtc      1536
Lys Ala Ala Val Lys Ser Gly Ile Lys Ala Phe Ile Lys Thr Leu Val
            500                 505                 510 aaa gcg att gcc aaa gcc att tct aaa gga atc tct aag gtt ttc gct      1584
Lys Ala Ile Ala Lys Ala Ile Ser Lys Gly Ile Ser Lys Val Phe Ala
            515                 520                 525 aag gga act caa atg att gcg aag aac ttc ccc aag ctc tcg aaa gtc      1632
Lys Gly Thr Gln Met Ile Ala Lys Asn Phe Pro Lys Leu Ser Lys Val
530                 535                 540 atc tcg tct ctt acc agt aaa tgg gtc acg gtt ggg gtt ggg gtt gta      1680
Ile Ser Ser Leu Thr Ser Lys Trp Val Thr Val Gly Val Gly Val Val
545                 550                 555                 560 gtt gcg gcg cct gct ctc ggt aaa ggg att atg caa atg cag ctc tcg      1728
Val Ala Ala Pro Ala Leu Gly Lys Gly Ile Met Gln Met Gln Leu Ser
                565                 570                 575 gag atg caa caa aac gtc gct caa ttt cag aaa gaa gtc gga aaa ctg      1776
Glu Met Gln Gln Asn Val Ala Gln Phe Gln Lys Glu Val Gly Lys Leu
            580                 585                 590 cag gct gcg gct gat atg att tct atg ttc act caa ttt tgg caa cag      1824
Gln Ala Ala Ala Asp Met Ile Ser Met Phe Thr Gln Phe Trp Gln Gln
            595                 600                 605 gca agt aaa att gcc tca aaa caa aca ggc gag tct aat gaa atg act      1872
Ala Ser Lys Ile Ala Ser Lys Gln Thr Gly Glu Ser Asn Glu Met Thr
            610                 615                 620 caa aaa gct acc aag ctg ggc gct caa atc ctt aaa gcg tat gcc gca      1920
Gln Lys Ala Thr Lys Leu Gly Ala Gln Ile Leu Lys Ala Tyr Ala Ala
625                 630                 635                 640 atc agc gga gcc atc gct ggc gca gca                                  1947
Ile Ser Gly Ala Ile Ala Gly Ala Ala
            645
```

```
<210> SEQ ID NO 18
<211> LENGTH: 1296
<212> TYPE: DNA
<213> ORGANISM: Artificial Sequence
<220> FEATURE:
<223> OTHER INFORMATION: fusion polynucleotide
<220> FEATURE:
<221> NAME/KEY: CDS
<222> LOCATION: (1)..(1296)
<223> OTHER INFORMATION:

<400> SEQUENCE: 18
```

| | | | | | | | | | | | | | | | | |
|---|---|---|---|---|---|---|---|---|---|---|---|---|---|---|---|---|
| atg | atc | agt | ctg | att | gcg | gcg | tta | gcg | gta | gat | cgc | gtt | atc | ggc | atg | 48 |
| Met | Ile | Ser | Leu | Ile | Ala | Ala | Leu | Ala | Val | Asp | Arg | Val | Ile | Gly | Met | |
| 1 | | | | 5 | | | | | 10 | | | | | 15 | | |
| gaa | aac | gcc | atg | ccg | tgg | aac | ctg | cct | gcc | gat | ctc | gcc | tgg | ttt | aaa | 96 |
| Glu | Asn | Ala | Met | Pro | Trp | Asn | Leu | Pro | Ala | Asp | Leu | Ala | Trp | Phe | Lys | |
| | | | 20 | | | | | 25 | | | | | 30 | | | |
| cgc | aac | acc | tta | aat | aaa | ccc | gtg | att | atg | ggc | cgc | cat | acc | tgg | gaa | 144 |
| Arg | Asn | Thr | Leu | Asn | Lys | Pro | Val | Ile | Met | Gly | Arg | His | Thr | Trp | Glu | |
| | | 35 | | | | | 40 | | | | | 45 | | | | |
| tca | atc | ggt | cgt | ccg | ttg | cca | gga | cgc | aaa | aat | att | atc | ctc | agc | agt | 192 |
| Ser | Ile | Gly | Arg | Pro | Leu | Pro | Gly | Arg | Lys | Asn | Ile | Ile | Leu | Ser | Ser | |
| | 50 | | | | | 55 | | | | | 60 | | | | | |
| caa | ccg | ggt | acg | gac | gat | cgc | gta | acg | tgg | gtg | aag | tcg | gtg | gat | gaa | 240 |
| Gln | Pro | Gly | Thr | Asp | Asp | Arg | Val | Thr | Trp | Val | Lys | Ser | Val | Asp | Glu | |
| 65 | | | | | 70 | | | | | 75 | | | | | 80 | |
| gcc | atc | gcg | gcg | tgt | ggt | gac | gta | cca | gaa | atc | atg | gtg | att | ggc | ggc | 288 |
| Ala | Ile | Ala | Ala | Cys | Gly | Asp | Val | Pro | Glu | Ile | Met | Val | Ile | Gly | Gly | |
| | | | | 85 | | | | | 90 | | | | | 95 | | |
| ggt | cgc | gtt | tat | gaa | cag | ttc | ttg | cca | aaa | gcg | caa | aaa | ctg | tat | ctg | 336 |
| Gly | Arg | Val | Tyr | Glu | Gln | Phe | Leu | Pro | Lys | Ala | Gln | Lys | Leu | Tyr | Leu | |
| | | | 100 | | | | | 105 | | | | | 110 | | | |
| acg | cat | atc | gac | gca | gaa | gtg | gaa | ggc | gac | acc | cat | ttc | ccg | gat | tac | 384 |
| Thr | His | Ile | Asp | Ala | Glu | Val | Glu | Gly | Asp | Thr | His | Phe | Pro | Asp | Tyr | |
| | | 115 | | | | | 120 | | | | | 125 | | | | |
| gag | ccg | gat | gac | tgg | gaa | tcg | gta | ttc | agc | gaa | ttc | cac | gat | gct | gat | 432 |
| Glu | Pro | Asp | Asp | Trp | Glu | Ser | Val | Phe | Ser | Glu | Phe | His | Asp | Ala | Asp | |
| | | 130 | | | | | 135 | | | | | 140 | | | | |
| gcg | cag | aac | tct | cac | agc | tat | gag | ttc | gaa | att | ctg | gag | cgg | cgg | atc | 480 |
| Ala | Gln | Asn | Ser | His | Ser | Tyr | Glu | Phe | Glu | Ile | Leu | Glu | Arg | Arg | Ile | |
| 145 | | | | | 150 | | | | | 155 | | | | | 160 | |
| ctg | atg | tct | att | tca | tct | tct | tca | gga | cct | gac | aat | caa | aaa | aat | atc | 528 |
| Leu | Met | Ser | Ile | Ser | Ser | Ser | Ser | Gly | Pro | Asp | Asn | Gln | Lys | Asn | Ile | |
| | | | | 165 | | | | | 170 | | | | | 175 | | |
| atg | tct | caa | gtt | ctg | aca | tcg | aca | ccc | cag | ggc | gtg | ccc | caa | caa | gat | 576 |
| Met | Ser | Gln | Val | Leu | Thr | Ser | Thr | Pro | Gln | Gly | Val | Pro | Gln | Gln | Asp | |
| | | | 180 | | | | | 185 | | | | | 190 | | | |
| aag | ctg | tct | ggc | aac | gaa | acg | aag | caa | ata | cag | caa | aca | cgt | cag | ggt | 624 |
| Lys | Leu | Ser | Gly | Asn | Glu | Thr | Lys | Gln | Ile | Gln | Gln | Thr | Arg | Gln | Gly | |
| | | 195 | | | | | 200 | | | | | 205 | | | | |
| aaa | aac | act | gag | atg | gaa | agc | gat | gcc | act | att | gct | ggt | gct | tct | gga | 672 |
| Lys | Asn | Thr | Glu | Met | Glu | Ser | Asp | Ala | Thr | Ile | Ala | Gly | Ala | Ser | Gly | |
| | | 210 | | | | | 215 | | | | | 220 | | | | |
| aaa | gac | aaa | act | tcc | tcg | act | aca | aaa | aca | gaa | aca | gct | cca | caa | cag | 720 |
| Lys | Asp | Lys | Thr | Ser | Ser | Thr | Thr | Lys | Thr | Glu | Thr | Ala | Pro | Gln | Gln | |
| 225 | | | | | 230 | | | | | 235 | | | | | 240 | |
| gga | gtt | gct | gct | ggg | aaa | gaa | tcc | tca | gaa | agt | caa | aag | gca | ggt | gct | 768 |
| Gly | Val | Ala | Ala | Gly | Lys | Glu | Ser | Ser | Glu | Ser | Gln | Lys | Ala | Gly | Ala | |
| | | | | 245 | | | | | 250 | | | | | 255 | | |
| gat | act | gga | gta | tca | gga | gcg | gct | gct | act | aca | gca | tca | aat | act | gca | 816 |

-continued

```
Asp Thr Gly Val Ser Gly Ala Ala Ala Thr Thr Ala Ser Asn Thr Ala
            260                 265                 270 aca aaa att gct atg cag acc tct att gaa gag gcg agc aaa agt atg      864
Thr Lys Ile Ala Met Gln Thr Ser Ile Glu Glu Ala Ser Lys Ser Met
        275                 280                 285 gag tct acc tta gag tca ctt caa agc ctc agt gcc gcg caa atg aaa      912
Glu Ser Thr Leu Glu Ser Leu Gln Ser Leu Ser Ala Ala Gln Met Lys
    290                 295                 300 gaa gtc gaa gcg gtt gtt gtt gct gcc ctc tca ggg aaa agt tcg ggt      960
Glu Val Glu Ala Val Val Val Ala Ala Leu Ser Gly Lys Ser Ser Gly
305                 310                 315                 320 tcc gca aaa ttg gaa aca cct gag ctc ccc aag ccc ggg gtg aca cca     1008
Ser Ala Lys Leu Glu Thr Pro Glu Leu Pro Lys Pro Gly Val Thr Pro
                325                 330                 335 aga tca gag gtt atc gaa atc gga ctc gcg ctt gct aaa gca att cag     1056
Arg Ser Glu Val Ile Glu Ile Gly Leu Ala Leu Ala Lys Ala Ile Gln
            340                 345                 350 aca ttg gga gaa gcc aca aaa tct gcc tta tct aac tat gca agt aca     1104
Thr Leu Gly Glu Ala Thr Lys Ser Ala Leu Ser Asn Tyr Ala Ser Thr
        355                 360                 365 caa gca caa gca gac caa aca aat aaa cta ggt cta gaa aag caa gcg     1152
Gln Ala Gln Ala Asp Gln Thr Asn Lys Leu Gly Leu Glu Lys Gln Ala
    370                 375                 380 ata aaa atc gat aaa gaa cga gaa gaa tac caa gag atg aag gct gcc     1200
Ile Lys Ile Asp Lys Glu Arg Glu Glu Tyr Gln Glu Met Lys Ala Ala
385                 390                 395                 400 gaa cag aag tct aaa gat ctc gaa gga aca atg gat act gtc aat act     1248
Glu Gln Lys Ser Lys Asp Leu Glu Gly Thr Met Asp Thr Val Asn Thr
                405                 410                 415 gtg atg atc gcg aag ggg ttc gaa ttg cca tgg ggg ccc tta att aat     1296
Val Met Ile Ala Lys Gly Phe Glu Leu Pro Trp Gly Pro Leu Ile Asn
            420                 425                 430

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA derived from Chlamydophila
      pneumoniae

<400> SEQUENCE: 19
agctgtctgg caacgaaacg                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA derived from Chlamydophila
      pneumoniae

<400> SEQUENCE: 20
gcagcaacaa caaccgcttc                                                 20

<210> SEQ ID NO 21
<211> LENGTH: 29
<212> TYPE: DNA
<213> ORGANISM: Artificial Sequence
<220> FEATURE:
<223> OTHER INFORMATION: Synthetic DNA

<400> SEQUENCE: 21
```

```
gatcctgatg tctatttcat cttcttcag                                      29

<210> SEQ ID NO 22
<211> LENGTH: 28
<212> TYPE: DNA
<213> ORGANISM: Artificial Sequence
<220> FEATURE:
<223> OTHER INFORMATION: Synthetic DNA

<400> SEQUENCE: 22
gtcctgaaga agatgaaata gacatcag                                       28

<210> SEQ ID NO 23
<211> LENGTH: 30
<212> TYPE: DNA
<213> ORGANISM: Artificial Sequence
<220> FEATURE:
<223> OTHER INFORMATION: Synthetic DNA

<400> SEQUENCE: 23
aattgccatg ggggccctta attaattaac                                     30

<210> SEQ ID NO 24
<211> LENGTH: 30
<212> TYPE: DNA
<213> ORGANISM: Artificial Sequence
<220> FEATURE:
<223> OTHER INFORMATION: Synthetic DNA

<400> SEQUENCE: 24
tcgagttaat taattaaggg cccccatggc                                     30

<210> SEQ ID NO 25
<211> LENGTH: 5438
<212> TYPE: DNA
<213> ORGANISM: Artificial Sequence
<220> FEATURE:
<223> OTHER INFORMATION: fusion polynucleotide

<400> SEQUENCE: 25
atcgatgtta acagatctaa gcttaactaa ctaactccgg aaaaggagga acttccatga    60
tcagtctgat tgcggcgtta gcggtagatc gcgttatcgg catggaaaac gccatgccgt   120
ggaacctgcc tgccgatctc gcctggttta acgcaacac cttaaataaa cccgtgatta    180
tgggccgcca tacctgggaa tcaatcggtc gtccgttgcc aggacgcaaa atattatcc    240 tcagcagtca accgggtacg gacgatcgcg taacgtgggt gaagtcggtg gatgaagcca   300
tcgcggcgtg tggtgacgta ccagaaatca tggtgattgg cggcggtcgc gtttatgaac   360
agttcttgcc aaaagcgcaa aaactgtatc tgacgcatat cgacgcagaa gtggaaggcg   420
acacccattt cccggattac gagccggatg actgggaatc ggtattcagc gaattccacg   480
atgctgatgc gcagaactct cacagctatg agttcgaaat tctggagcgg cggatcctga   540
tgtctatttc atcttcttca ggacctgaca atcaaaaaaa tatcatgtct caagttctga   600
catcgacacc ccagggcgtg ccccaacaag ataagctgtc tggcaacgaa acgaagcaaa   660
tacagcaaac acgtcagggt aaaaacactg agatggaaag cgatgccact attgctggtg   720
cttctggaaa agacaaaaact tcctcgacta caaaaacaga aacagctcca acagggag    780 ttgctgctgg gaaagaatcc tcagaaagtc aaaaggcagg tgctgatact ggagtatcag   840
gagcggctgc tactacagca tcaaatactg caacaaaaat tgctatgcag acctctattg   900
aagaggcgag caaaagtatg gagtctacct tagagtcact tcaaagcctc agtgccgcgc   960
```

```
aaatgaaaga agtcgaagcg gttgttgttg ctgccctctc agggaaaagt tcgggttccg    1020
caaaattgga acacctgag ctccccaagc ccggggtgac accaagatca gaggttatcg     1080
aaatcggact cgcgcttgct aaagcaattc agacattggg agaagccaca aaatctgcct    1140
tatctaacta tgcaagtaca caagcacaag cagaccaaac aaataaacta ggtctagaaa    1200
agcaagcgat aaaaatcgat aaagaacgag aagaatacca agagatgaag gctgccgaac    1260
agaagtctaa agatctcgaa ggaacaatgg atactgtcaa tactgtgatg atcgcgaagg    1320
ggttcgaatt gccatggggg cccttaatta attaactcga gagatccaga tctaatcgat    1380
gatcctctac gccggacgca tcgtggccgg catcaccggc ccacaggtg cggttgctgg     1440 cgcctatatc gccgacatca ccgatgggga agatcgggct cgccacttcg ggctcatgag    1500
cgcttgtttc ggcgtgggta tggtggcagg cccgtggccg ggggactgtt gggcgccatc    1560
tccttgcatg caccattcct tgcggcggcg gtgctcaacg gcctcaacct actactgggc    1620
tgcttcctaa tgcaggagtc gcataaggga gagcgtcgac cgatgccctt gagagccttc    1680
aacccagtca gctccttccg gtgggcgcgg ggcatgacta tcgtcgccgc acttatgact    1740
gtcttcttta tcatgcaact cgtaggacag gtgccggcag cgctctgggt cattttcggc    1800
gaggaccgct ttcgctggag cgcgacgatg atcggcctgt cgcttgcggt attcggaatc    1860
ttgcacgccc tcgctcaagc cttcgtcact ggtcccgcca ccaaacgttt cggcgagaag    1920
caggccatta tcgccggcat ggcggccgac gcgctgggct acgtcttgct ggcgttcgcg    1980
acgcgaggct ggatggcctt ccccattatg attcttctcg cttccggcgg catcgggatg    2040
cccgcgttgc aggccatgct gtccaggcag gtagatgacg accatcaggg acagcttcaa    2100
ggatcgctcg cggctcttac cagcctaact tcgatcactg gaccgctgat cgtcacggcg    2160
atttatgccg cctcggcgag cacatggaac ggggttggcat ggattgtagg cgccgccta    2220 taccttgtct gcctccccgc gttgcgtcgc ggtgcatgga gccgggccac ctcgacctga    2280
atggaagccg gcggcacctc gctaacggat tcaccactcc aagaattgga gccaatcaat    2340
tcttgcggag aactgtgaat gcgcaaacca acccttggca gaacatatcc atcgcgtccg    2400
ccatctccag cagccgcacg cggcgcatct cgggcagcgt tgggtcctgg ccacgggtgc    2460
gcatgatcgt gctcctgtcg ttgaggaccc ggctaggctg cgggggttgc cttactggtt    2520
agcagaatga atcaccgata cgcgagcgaa cgtgaagcga ctgctgctgc aaaacgtctg    2580
cgacctgagc aacaacatga atggtcttcg gtttccgtgt ttcgtaaagt ctggaaacgc    2640
ggaagtcagc gccctgcacc attatgttcc ggatctgcat cgcaggatgc tgctggctac    2700
cctgtggaac acctacatct gtattaacga agcgctggca ttgaccctga gtgattttc    2760 tctggtcccg ccgcatccat accgccagtt gtttaccctc acaacgttcc agtaaccggg    2820
catgttcatc atcagtaacc cgtatcgtga gcatcctctc tcgtttcatc ggtatcatta    2880
cccccatgaa cagaaattcc cccttacacg gaggcatcaa gtgaccaaac aggaaaaaac    2940
cgcccttaac atgccccgct ttatcagaag ccagacatta acgcttctgg agaaactcaa    3000
cgagctggac gcggatgaac aggcagacat ctgtgaatcg cttcacgacc acgctgatga    3060
gctttaccgc agctgcctcg cgcgtttcgg tgatgacggt gaaaacctct gacacatgca    3120
gctcccggag acggtcacag cttgtctgta agcggatgcc gggagcagac aagcccgtca    3180
gggcgcgtca gcgggtgttg gcgggtgtcg ggcgcagcc atgacccagt cacgtagcga    3240
tagcggagtg tatactggct taactatgcg gcatcagagc agattgtact gagagtgcac    3300
```

-continued

```
catatgcggt gtgaaatacc gcacagatgc gtaaggagaa ataccgcat caggcgctct    3360 tccgcttcct cgctcactga ctcgctgcgc tcggtcgttc ggctgcggcg agcggtatca    3420
gctcactcaa aggcggtaat acggttatcc acagaatcag gggataacgc aggaaagaac    3480
atgtgagcaa aaggccagca aaaggccagg aaccgtaaaa aggccgcgtt gctggcgttt    3540
ttccataggc tccgccccc tgacgagcat cacaaaaatc gacgctcaag tcagaggtgg    3600
cgaaacccga caggactata agataccag gcgtttcccc ctggaagctc cctcgtgcgc    3660
tctcctgttc cgaccctgcc gcttaccgga tacctgtccg cctttctccc ttcgggaagc    3720
gtggcgcttt ctcaatgctc acgctgtagg tatctcagtt cggtgtaggt cgttcgctcc    3780
aagctgggct gtgtgcacga accccccgtt cagcccgacc gctgcgcctt atccggtaac    3840
tatcgtcttg agtccaaccc ggtaagacac gacttatcgc cactggcagc agccactggt    3900
aacaggatta gcagagcgag gtatgtaggc ggtgctacag agttcttgaa gtggtggcct    3960
aactacggct acactagaag gacagtattt ggtatctgcg ctctgctgaa gccagttacc    4020
ttcggaaaaa gagttggtag ctcttgatcc ggcaaacaaa ccaccgctgg tagcggtggt    4080
ttttttgttt gcaagcagca gattacgcgc agaaaaaaag gatctcaaga agatcctttg    4140
atcttttcta cggggtctga cgctcagtgg aacgaaaact cacgttaagg gattttggtc    4200
atgagattat caaaaaggat cttcacctag atcctttta attaaaaatg aagttttaaa    4260
tcaatctaaa gtatatatga gtaaacttgg tctgacagtt accaatgctt aatcagtgag    4320
gcacctatct cagcgatctg tctatttcgt tcatccatag ttgcctgact ccccgtcgtg    4380
tagataacta cgatacggga gggcttacca tctggcccca gtgctgcaat gataccgcga    4440
gacccacgct caccggctcc agatttatca gcaataaacc agccagccgg aagggccgag    4500
cgcagaagtg gtcctgcaac tttatccgcc tccatccagt ctattaattg ttgccgggaa    4560
gctagagtaa gtagttcgcc agttaatagt ttgcgcaacg ttgttgccat tgctgcaggc    4620
atcgtggtgt cacgctcgtc gtttggtatg gcttcattca gctccggttc ccaacgatca    4680
aggcgagtta catgatcccc catgttgtgc aaaaaagcgg ttagctcctt cggtcctccg    4740
atcgttgtca gaagtaagtt ggccgcagtg ttatcactca tggttatggc agcactgcat    4800
aattctctta ctgtcatgcc atccgtaaga tgcttttctg tgactggtga gtactcaacc    4860
aagtcattct gagaatagtg tatgcggcga ccgagttgct cttgcccggc gtcaacacgg    4920
gataataccg cgccacatag cagaacttta aaagtgctca tcattggaaa acgttcttcg    4980
gggcgaaaac tctcaaggat cttaccgctg ttgagatcca gttcgatgta acccactcgt    5040
gcacccaact gatcttcagc atcttttact ttcaccagcg tttctgggtg agcaaaaaca    5100
ggaaggcaaa atgccgcaaa aaagggaata agggcgacac ggaaatgttg aatactcata    5160
ctcttccttt ttcaatatta ttgaagcatt tatcagggtt attgtctcat gagcggatac    5220
atatttgaat gtatttagaa aaataaacaa ataggggttc cgcgcacatt tccccgaaaa    5280
gtgccacctg acgtctaaga aaccattatt atcatgacat taacctataa aaataggcgt    5340
atcacgaggc cctttcgtct tcaagaatta attgttatcc gctcacaatt aattcttgac    5400
aattagttaa ctatttgtta taatgtattc ataagctt                            5438
```

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA derived from Chlamydophila pneumoniae

<400> SEQUENCE: 26
gctgccgaac agaagtctaa                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic DNA derived from Chlamydophila
      pneumoniae

<400> SEQUENCE: 27
ctcgaaggaa caatggatac                    20

<210> SEQ ID NO 28
<211> LENGTH: 23
<212> TYPE: DNA
<213> ORGANISM: Artificial Sequence
<220> FEATURE:
<223> OTHER INFORMATION: Synthetic DNA

<400> SEQUENCE: 28
gtacatattg tcgttagaac gcg                23

<210> SEQ ID NO 29
<211> LENGTH: 23
<212> TYPE: DNA
<213> ORGANISM: Artificial Sequence
<220> FEATURE:
<223> OTHER INFORMATION: Synthetic DNA

<400> SEQUENCE: 29
taatacgact cactataggg aga                23

<210> SEQ ID NO 30
<211> LENGTH: 28
<212> TYPE: DNA
<213> ORGANISM: Artificial Sequence
<220> FEATURE:
<223> OTHER INFORMATION: Synthetic DNA derived from Chlamydophila
      pneumoniae

<400> SEQUENCE: 30
gcggatcctg atgtctattt catcttct            28

<210> SEQ ID NO 31
<211> LENGTH: 30
<212> TYPE: DNA
<213> ORGANISM: Artificial Sequence
<220> FEATURE:
<223> OTHER INFORMATION: Synthetic DNA derived from Chlamydophila
      pneumoniae

<400> SEQUENCE: 31
atctcgagtt ttatgctgct gcgccagcga          30

<210> SEQ ID NO 32
<211> LENGTH: 16
<212> TYPE: DNA
<213> ORGANISM: Artificial Sequence
<220> FEATURE:
<223> OTHER INFORMATION: Synthetic DNA -continued

```
<400> SEQUENCE: 32
aattcgaacc ccttcg                                                16

<210> SEQ ID NO 33
<211> LENGTH: 12
<212> TYPE: DNA
<213> ORGANISM: Artificial Sequence
<220> FEATURE:
<223> OTHER INFORMATION: Synthetic DNA

<400> SEQUENCE: 33
cgaaggggtt cg                                                    12
```